US012773441B2

(12) United States Patent
Lozano Soto et al.

(10) Patent No.: US 12,773,441 B2
(45) Date of Patent: Oct. 27, 2026

(54) BACTERIAL-BINDING PEPTIDES FOR TREATMENT OF INFECTIOUS DISEASES AND RELATED INFLAMMATORY PROCESSES

(71) Applicant: Sepsia Therapeutics, S.L., L'hospitalet de Llobergat (ES)

(72) Inventors: Francisco Lozano Soto, Barcelona (ES); Mario Martínez Florensa, Barcelona (ES)

(73) Assignee: Sepsia Therapeutics, S.L., L'hospitalet de Llobergat (ES)

( * ) Notice: Subject to any disclaimer, the term of this patent is extended or adjusted under 35 U.S.C. 154(b) by 0 days.

(21) Appl. No.: 18/303,441

(22) Filed: Apr. 19, 2023

(65) Prior Publication Data

US 2023/0381266 A1 Nov. 30, 2023

Related U.S. Application Data

(62) Division of application No. 16/980,275, filed as application No. PCT/EP2019/056315 on Mar. 13, 2019, now Pat. No. 11,660,326.

(30) Foreign Application Priority Data

Mar. 13, 2018 (EP) .................................... 18382164

(51) Int. Cl.

| | |
|---|---|
| ***A61K 38/08*** | (2019.01) |
| ***A61K 31/198*** | (2006.01) |
| ***A61K 31/407*** | (2006.01) |
| ***A61K 47/56*** | (2017.01) |

(52) U.S. Cl.

CPC ............ *A61K 38/08* (2013.01); *A61K 31/198* (2013.01); *A61K 31/407* (2013.01); *A61K 47/56* (2017.08)

(58) Field of Classification Search

CPC .... A61K 38/08; A61K 31/198; A61K 31/407; A61K 47/56; A61K 38/177; A61P 31/00

See application file for complete search history.

(56) References Cited

U.S. PATENT DOCUMENTS

| | | | |
|---|---|---|---|
| 2004/0171123 A1 | 9/2004 | Rosen et al. | |
| 2014/0215644 A1 | 7/2014 | Lozano Soto et al. | |

FOREIGN PATENT DOCUMENTS

| | | |
|---|---|---|
| EP | 2 143 436 A1 | 1/2018 |
| WO | 2018/025052 A1 | 2/2018 |
| WO | 2018/091679 A1 | 5/2018 |

OTHER PUBLICATIONS

National Cancer Institute, Risk Factors Infectious Agents, accessed on Oct. 14, 2024.*

Aibar et al., "Pattern of soluble CD5 and CD6 lymphocyte receptors in critically ill patients with septic syndromes" *Journal of Critical Care* 30:914-919, 2015.

Albericio et al., Supporting information for *J. Org. Chem.* 55(12):3730-3743, 1990.

Barlos et al., "Darstellung Geschützter Peptid-Fragmente unter Einsatz Substituierter Triphenylmethyl-Harze," *Tetrahedron Lett.* 30(30):3943-3946, 1989. (with English abstract).

Barlos et al., "Veresterung Von Partiell Geschützten Peptid-Fragmenten Mit Harzen. Einsatz Von 2-Chlortritylchlorid Zur Synthese Von Leu$^{15}$-Gastrin I," *Tetrahedron Lett.* 30(30):3947-3950, 1989.

Bessa Pereira et al., "The Scavenger Receptor SSc5D Physically Interacts with Bacteria through the SRCR-Containing N-Terminal Domain," *Front. Immunol.* 7(416):1-9, 2016.

Bikker et al., "Bacteria Binding by DMBTI/SAG/gp-340 Is Confined to the VEVLXXXXW Motif in Its Scavenger Receptor Cysteine-rich Domains," *Journal of Biological Chemistry* 279(46):47699-47703, 2004.

Bikker et al., "Identification of the Bacteria-binding Peptide Domain on Salivary Agglutinin (gp-340/DMBT1), a Member of the Scavenger Receptor Cysteine-rich Superfamily," *J. Biol. Chem.* 277(35):32109-32115, 2002.

Bikker et al., "Salivary Agglutinin: Structure and function," *Academisch Proefschrift*, Vrije Universiteit, Optima grafische communicatie, pp. 1-136, 2004.

Brännström et al., "Arginine Residues in Domain V Have a Central Role for Bacteria-Binding Activity of Macrophage Scavenger Receptor Marco," *Biochem. Biophys. Res. Commun.* 290:1462-1469, 2002.

Daga Ruiz et al., "Plasmapheresis and other extracorporeal filtration techniques in critical patients," *Med. Intensiva.* 41(3):174-187, 2017.

Delano et al., "Sepsis-induced immune dysfunction: can immune therapies reduce mortality?" *J. Clin. Invest.* 126(1):23-31, 2016.

Dziarski et al., "Binding of Bacterial Peptidoglycan to CD14," *J. Biol. Chem.* 273(15):8680-8690, 1998.

Esteban et al., "Immunomodulation in Sepsis: The Role of Endotoxin Removal by Polymyxin B-Immobilized Cartridge," *Mediators Inflamm.* 2013(507539):1-12, 2013.

(Continued)

*Primary Examiner* — Erinne R Dabkowski

(74) *Attorney, Agent, or Firm* — Seed Intellectual Property Law Group LLP

(57) ABSTRACT

The present invention relates to the field of medicine and provides pharmaceutical compositions comprising one or more of the following isolated amino acid sequences comprising or, alternatively, consisting of, SEQ ID No.: 3, and/or SEQ ID No.: 1, and/or SEQ ID No.: 2, kits and conjugates comprising one or more of the above mentioned amino acid sequences. In addition, the present invention relates to the use of the pharmaceutical compositions, kits and conjugates of the present invention as a medicament, in particular in the treatment of an infectious disease, or of an inflammatory condition related to an infectious disease, or of an inflammatory disease related to the presence of a product derived from an infectious agent. The present invention also provides a device for selective binding and separation of at least one component from an aqueous solution wherein the device comprises one or more of the above mentioned amino acid sequences.

9 Claims, 13 Drawing Sheets

Specification includes a Sequence Listing.

(56) References Cited

OTHER PUBLICATIONS

Fabriek et al., "The macrophage scavenger receptor CD163 functions as an innate immune sensor for bacteria," *Blood* 113(4):887-892, 2009.
García-Verdugo et al., "Effect of Hydroxylation and $N^{187}$-Linked Glycosylation on Molecular and Functional Properties of Recombinant Human Surfactant Protein A," *Biochemistry* 42:9532-9542, 2003.
Gimferrer et al., "Relevance of CD6-Mediated Interactions in T Cell Activation and Proliferation," *J. Immunol.* 173:2262-2270, 2004.
Janeway, Jr. et al., "Innate Immune Recognition," *Annu. Rev. Immunol.* 20:197-216, 2002.
Jiang et al., "Identification and Characterization of Murine SCARA5, a Novel Class A Scavenger Receptor That Is Expressed by Populations of Epithelial Cells," *J. Biol. Chem.* 281(17):11834-11845, 2006.
Kullmann, "Proteases as Catalysts for Enzymic Syntheses of Opioid Peptides," *J. Biol. Chem.* 255(17):8234-8238, 1980.
Lecomte et al., "Molecular linkage of the mouse CD5 and CD6 genes," *Immunogenetics* 44:385-390, 1996.
Ligtenberg et al., "Deleted in Malignant Brain Tumors-1 Protein (DMBT1): A Pattern Recognition Receptor with Multiple Binding Sites," *Int. J. Mol. Sci.* 11:5212-5233, 2010.
Madsen et al., "Gp-340/DMBTI in mucosal innate immunity," *Innate Immun.* 16(3):160-167, 2010.
Martin, "Sepsis, severe sepsis and septic shock: changes in incidence, pathogens and outcomes," *Expert Rev. Anti. Infect. Ther.* 10(6):701-706, 2012.
Martínez et al., "The Conserved Scavenger Receptor Cysteine-Rich Superfamily in Therapy and Diagnosis," *Pharmacol. Rev.* 63(4):967-1000, 2011.
Martínez-Florensa et al., "Conserved Bacterial-Binding Peptides of the Scavenger-Like Human Lymphocyte Receptor CD6 Protect From Mouse Experimental Sepsis," *Frontiers in Immunology* 9(627):1-11, 2018.
Martínez-Florensa et al., "Protective Effects of Human and Mouse Soluble Scavenger-Like CD6 Lymphocyte Receptor in a Lethal Model of Polymicrobial Sepsis," *Antimicrob. Agents Chemother.* 61(1):e01391-16, 2017. (10 pages).
Martínez-Florensa et al., "Targeting of Key Pathogenic Factors From Gram-Positive Bacteria by the Soluble Ectodomain of the Scavenger-Like Lymphocyte Receptor CD6," *J. Infect. Dis.* 209:1077-1086, 2014.
Matsueda et al., "A p-Methylbenzhydrylamine Resin for Improved Solid-Phase Synthesis of Peptide Amides," *Peptides* 2:45-50, 1981.
McInerney et al., "Quantitation of Polymyxin-Lipopolysaccharide Interactions Using an Image-Based Fluorescent Probe," *J. Pharm. Sci.* 105:1006-1010, 2016.
Miró-Julià et al., "Molecular and Functional Characterization of Mouse S5D-SRCRB: A New Group B Member of the Scavenger Receptor Cysteine-Rich Superfamily," *J. Immunol.* 186(4):2344-2354, 2011.
Nguyen et al., "Severe Sepsis and Septic Shock: Review of the Literature and Emergency Department Management Guidelines," *Ann. Emergency Med.* 48(1):28-54, 2006.
Okeke et al., "In Search of a Cure for Sepsis: Taming the Monster in Critical Care Medicine," *J. Innate Immun.* 8:156-170, 2016.
Palm et al., "Pattern recognition receptors and control of adaptive immunity," *Immunol. Rev.* 227:221-233, 2009.
Peiser et al., "Macrophage Class A Scavenger Receptor-Mediated Phagocytosis of *Escherichia coli*: Role of Cell Heterogeneity, Microbial Strain, and Culture Conditions In Vitro," *Infect. Immun.* 68(4):1953-1963, 2000.
Rimmelé et al., "Clinical review: Blood purification for sepsis," *Critical Care* 15(205):1-10, 2011.
Rink, "Solid-Phase Synthesis of Protected Peptide Fragments Using a Trialkoxy-Diphenyl-Methylester Resin," *Tetrahedron Lett.* 28(33):3787-3790, 1987.
Sáenz et al., "Fluidizing effects of C-reactive protein on lung surfactant membranes: protective role of surfactant protein A," *FASEB J.* 24:3662-3673, 2010.
Santos et al., "Tuning T Cell Activation: The Function of CD6 at the Immunological Synapse and in T Cell Responses," *Curr. Drug Targets* 17:630-639, 2016.
Sarrias et al., "A Role for Human SPα as a Pattern Recognition Receptor," *J. Biol. Chem.* 280(42):35391-35298, 2005.
Sarrias et al., "CD6 binds to pathogen-associated molecular patterns and protects from LPS-induced septic shock," *PNAS* 104(28):11724-11729, Jul. 10, 2007.
Sarrias et al., "The Scavenger Receptor Cysteine-Rich (SRCR) Domain: An Ancient and Highly Conserved Protein Module of the Innate Immune System," *Crit. Rev. Immunol.* 24(1):1-38, 2004.
Shimizu et al., "History and current status of polymyxin B-immobilized fiber column for treatment of severe sepsis and septic shock," *Ann. Gastroenterol. Surg.* 1:105-113, 2017.
Skonier et al., "Mutational analysis of the CD6 ligand binding domain," *Protein Engineering* 10(8):943-947, 1997.
Soldevila et al., "The immunomodulatory properties of the CD5 lymphocyte receptor in health and disease," *Curr. Opin. Immunol.* 23:(3):310-318, 2011.
The On-Line Medical Dictionary, "Derivative," accessed: Jul. 7, 2005 (5 pages).
Tobias et al., "Lipopolysaccharide binding protein-mediated complexation of lipopolysaccharide with soluble CD14," *J. Biol. Chem.* 270(18):10482-10488, 1995.
UniProtKB—P30203 (CD6_Human), "T-cell differentiation antigen CD6," last modified: Sep. 29, 2021 (17 pages).
Velasco-de Andrés et al., "Soluble CD5 and CD6: Lymphocytic Class I Scavenger Receptors as Immunotherapeutic Agents," *Cells* 9(2589):1-17, 2020.
Verwaest, "Meropenem versus imipenem/cilastatin as empirical monotherapy for serious bacterial infections in the intensive care unit," *Clin. Microbiol. Infect.* 6(6):294-302, 2000.
Wang, "p-Alkoxybenzyl Alcohol Resin and p-Alkoxybenzyloxycarbonylhydrazide Resin for Solid Phase Synthesis of Protected Peptide Fragments," *J. Am. Chem. Soc.* 95(4):1328-1333, 1973.
Zimmermann et al., "Endotoxin Adsorbent Based on Immobilized Human Serum Albumin," *Clin. Chem. Lab. Med.* 37(3):373-379, 1999.
Carrasco et al., "A Role for Scavenger-like Lymphocyte Receptor CD6 in HIV-1 Viral Infection," *AIDS Research and Human Retroviruses* 30(Suppl. 1): A49-A50, Oct. 2014. (2 pages).
Enyindah-Asonye et al., "Overexpression of CD6 and PD-1 Identifies Dysfunctional $CD8_+$ T-Cells During Chronic SIV Infection of Rhesus Macaques," *Frontiers in Immunology* 10:3005, Jan. 8, 2020. (13 pages).
Miles et al., "Interactome analysis of CD5 and CD6 ectodomains with tegumental antigens from the helminth parasite *Echinococcus granulosus sensu lato," International Journal of Biological Macromolecules* 164:3718-3728, Sep. 4, 2020. (11 pages).
Mourglia-Ettlin et al., "The ectodomains of the lymphocyte scavenger receptors CD5 and CD6 interact with tegumental antigens from Echinococcus granulosus sensu lato and protect mice against secondary cystic echinococcosis," *PLoS Neglected Tropical Diseases* 12(11):e0006891, Nov. 30, 2018. (24 pages).
Vera et al., "The CD5 ectodomain interacts with conserved fungal cell wall components and protects from zymosan-induced septic shock-like syndrome," *PNAS* 106(5):1506-1511, Feb. 3, 2009. (6 pages).

* cited by examiner

A

| | aa sequence | M.W. kDa | pI | Net charge at pH 7 |
|---|---|---|---|---|
| peptides | | | | |
| SEQ ID NO: 1 | GTVEVRLEASW | 1.24 | 4.15 | -1 |
| SEQ ID NO: 2 | GRVEMLEHGEW | 1.34 | 4.44 | -1.9 |
| SEQ ID NO: 3 | GQVEVHFRGVW | 1.31 | 7.81 | +0.1 |
| SEQ ID NO: 9 | GRVEVLFRGSW | 1.31 | 10.7 | +1 |
| SEQ ID NO: 8 | GRVEVLYRGSW | 1.32 | 9.83 | +1 |
| SEQ ID NO: 6 | GQLEVYLKDGW | 1.30 | 3.93 | -1 |
| SEQ ID NO: 7 | GVVEFYSGSLG | 1.11 | 3.85 | -1 |
| proteins | | | | |
| rshCD6 | $D^{25}$-$R^{397}$ | 39.7 | 4.97 | -15.5 |
| rshCD5 | $R^{25}$-$D^{345}$ | 38.2 | 7.63 | +4.4 |

B

C

| | | | | | | |
|---|---|---|---|---|---|---|
| *H. sapiens* | CSGTVEVRLEASWEPA-C | SEQ ID NO:13 | CAGRVEMLEHGEWGSVC | SEQ ID NO:21 | CEGQVEVHFRGVWNTVC | SEQ ID NO:29 |
| *P. Troglodytes* | CSGTVEVRLEASWEPA-C | SEQ ID NO:13 | CAGRVEMLEHGEWGSVC | SEQ ID NO:21 | CEGQVEVHFRGVWNTVC | SEQ ID NO:29 |
| *N. leucogenys* | CSGTVEVRFEASWEPA-C | SEQ ID NO:40 | CAGRVEMLEHGEWGSVC | SEQ ID NO:21 | CEGQVEVHFRGVWNTVC | SEQ ID NO:29 |
| *M. mulatta* | CSGTVEVRLRASWEPA-C | SEQ ID NO:41 | CAGRVEMLEHGEWGSVC | SEQ ID NO:21 | CEGQVEVHFRGVWNTVC | SEQ ID NO:29 |
| *T. syrichta* | WG--SGLHGGSGMGQP-G | SEQ ID NO:42 | CAGRVEILERGQWGSVC | SEQ ID NO:54 | CEGQVEVHFRGVWSTVC | SEQ ID NO:64 |
| *M. musculus* | CSGSVKVLL-ESWEPV-C | SEQ ID NO:43 | CAGRVEMLEHGEWGTVC | SEQ ID NO:55 | CEGQVEVYFRGVWSTVC | SEQ ID NO:65 |
| *R. norvegicus* | CSGFVQVLL-ESWEPV-C | SEQ ID NO:44 | CAGRVEMLQHGEWGTVC | SEQ ID NO:56 | CEGQVEVYFRGVWSTVC | SEQ ID NO:65 |
| *M. auratus* | CSGSVEVLLGASWEPA-H | SEQ ID NO:45 | CAGRVEMLEHGEWGTVC | SEQ ID NO:55 | CEGQVEVHYQGVWSTVC | SEQ ID NO:66 |
| *O. cuniculus* | CSGTVEVWFGEAWKAA-C | SEQ ID NO:46 | CAGRVEMLEYGRWGSVC | SEQ ID NO:57 | CEGQVEVHFRGVWSTVC | SEQ ID NO:64 |
| *B. taurus* | CEGTVEVWFQQSWQPV-C | SEQ ID NO:47 | CEGRVEMLEHGQWGSVC | SEQ ID NO:58 | CEGQVEVYFRGVWNTVC | SEQ ID NO:67 |
| *S. scrofa* | CNGTVEVRLGLSWKPA-C | SEQ ID NO:48 | CEGRVEMLEHGQWGSVC | SEQ ID NO:58 | CEGQVEVYYRGVWNTVC | SEQ ID NO:68 |
| *C. lupus fam.* | CSGLVEVWFRLSWGPA-C | SEQ ID NO:49 | CAGRVEMLEHRQWGSVC | SEQ ID NO:59 | CEGQVEVHFRGVWSTVC | SEQ ID NO:64 |
| *F. silv. catus* | CSGTVEVWIRQSWEPA-C | SEQ ID NO:50 | CAGRVEMLERGQWGSVC | SEQ ID NO:60 | CEGQVEVHFRGVWSTVC | SEQ ID NO:64 |
| *A. mississipp.* | CKGTVEVHYHGMWVPA-C | SEQ ID NO:51 | CEGRVEVSEADVWGTVC | SEQ ID NO:61 | CAGQVEVYYKGSWNTVC | SEQ ID NO:69 |
| *P. prolifica* | CRWTFRLPGNRSGEAVPL | SEQ ID NO:52 | CAGRVEVWKDGTWGTVC | SEQ ID NO:62 | ----------------- | |
| *S. salar* | CSGVVEVLHRGLWRPV-T | SEQ ID NO:53 | CEGRVELWREEKWGTVC | SEQ ID NO:63 | ----------------- | |

*FIG. 1C*

FIGURE 2

A

| | µg/ml | (C+) pbs1 | CD5 PD2 | CD6 cons | CD6 PD1 | CD6 PD2 | CD6 PD3 |
|---|---|---|---|---|---|---|---|
| *A. baumannii* MDR | 5 | -/+ | - | - | - | - | - |
| | 50 | +++ | - | +++ | -/+ | - | - |
| | 200 | +++ | - | +++ | +++ | - | +++ |
| *Enterococcus* | 5 | ++ | - | - | - | - | - |
| | 50 | +++ | - | +++ | - | - | + |
| | 200 | +++ | - | +++ | +++ | - | +++ |
| *K. pneumoniae* | 5 | - | - | - | - | - | - |
| | 50 | - | - | - | - | - | - |
| | 200 | +++ | - | +++ | + | - | - |
| *L. monocytogenes* | 5 | - | - | - | - | - | - |
| | 50 | +++ | - | +++ | - | - | -/+ |
| | 200 | +++ | - | +++ | +++ | - | +++ |
| *P. aeruginosa* | 5 | -/+ | - | -/+ | - | - | - |
| | 50 | +++ | - | +++ | +++ | - | - |
| | 200 | +++ | NA | +++ | +++ | - | +++ |
| *S. aureus* | 5 | +++ | - | -/+ | - | - | -/+ |
| | 50 | +++ | - | +++ | - | - | + |
| | 200 | +++ | - | +++ | ++ | - | ++ |
| MRSA | 5 | +++ | - | -/+ | - | - | - |
| | 50 | +++ | - | +++ | -/+ | - | +++ |
| | 200 | +++ | - | +++ | +++ | - | +++ |

A

B

| Protein/Peptide | $K_d$ LPS (Gram-) | $K_d$ LTA (Gram+) |
|---|---|---|
| rshCD6 | 630 ± 10 nM | 11 ± 4 nM |
| CD6.PD1 | 3.5 ± 0.3 nM | 0.39 ± 0.06 nM |
| CD6.PD2 | 35 ± 2 nM | 0.31 ± 0.04 nM |
| CD6.PD3 | 3000 ± 30 nM | 36 ± 2 nM |
| CD6.cons | 13 ± 1 nM | 4.4 ± 0.4 nM |
| DMBT-1.pbs1 | 860 ± 50 nM | 260 ± 20 nM |

| Sample | Size (nm) | |
|---|---|---|
| | $\phi_1$ (nm) | $\phi_2$ (nm) |
| CD6.cons | 5493 ± 7 | 1636 ± 6 |
| CD6.PD1 | 321 ± 5 | 1484 ± 8 |
| CD6.PD2 | 379 ± 5 | |
| CD6.PD3 | 5151 ± 7 | 630 ± 3 |
| DMBT-1.psb1 | 617 ± 4 | 169 ± 5 |

BACTERIAL-BINDING PEPTIDES FOR TREATMENT OF INFECTIOUS DISEASES AND RELATED INFLAMMATORY PROCESSES

TECHNICAL FIELD

This invention relates to the field of medicine, and specifically to bacterial-binding peptides of the scavenger-like human CD6 lymphocyte receptor, which are useful in the therapeutic and/or preventive treatment of infectious diseases and of inflammatory conditions related thereto, as well as to devices comprising the peptides.

REFERENCE TO AN ELECTRONIC SEQUENCE LISTING

The contents of the electronic sequence listing (850247_401D1_SEQUENCE_LISTING.xml; Size: 90340 bytes; and Date of Creation: Apr. 19, 2023) is herein incorporated by reference in its entirety.

BACKGROUND ART

Sepsis is a life-threatening condition caused by the host response to an infectious agent, most commonly bacterial but also fungal, viral or parasitic. Sepsis is considered a dysregulated systemic inflammatory response syndrome (SIRS) caused by an infection, leading to an overwhelming and sustained pro-inflammatory state. The inability of the immune system to control such a response can end in multi-organ dysfunction (MOD) and cardiovascular collapse (septic shock) and, if unresolved, to death (Delano M J and Ward P A, 2016, *Sepsis-induced immune dysfunction: can immune therapies reduce mortality? J Clin Invest* 126:23-31). Such a dysfunctional host inflammatory response is triggered by conserved structures present on microbial cell walls named pathogen associated molecular patterns (PAMPs). PAMPs are essential compounds for the microbial physiology, among which there is LPS from Gram-negative (G−) bacteria, lipoteichoic acid (LTA) and peptidoglycan (PGN) from Gram-positive (G+) bacteria, β-glucan and mannan from fungi, or single/double-stranded nucleic acids from virus (Janeway C A and Medzhitov R, 2002, *Innate immune recognition, Annu Rev Immunol* 20:197-216).

Sepsis can result from many causes but is typically triggered by undiagnosed and/or untreated local infections (e.g., pneumonia or peritonitis) induced either spontaneously or as a consequence of trauma, surgery, burns or by debilitating conditions such as cancer or AIDS. Sepsis usually begins with tremor, fever, falling blood pressure (septic shock), rapid breathing, rapid heart rate, and skin lesions. Within hours, sepsis may cause spontaneous clotting in blood vessels, severe hypotension, multiple organ failure, shock, gangrene and eventually death.

Detection of PAMPs is accomplished by germ-line encoded, non-clonally distributed, and non-polymorphic pattern recognition receptors (PRRs) present on immune cells. PRRs belong to different structural and functional protein receptor families (e.g., Toll like receptors, Scavenger receptors or C-type lectins), and contribute not only to pathogen detection but engagement and modulation of innate and adaptive immune responses (Palm N W and Medzhitov R, 2009, *Pattern recognition receptors and control of adaptive immunity, Immunol Rev* 227:221-33).

The Scavenger Receptor Cysteine-Rich superfamily (SRCR-SF) is an ancient and highly conserved group of protein receptors characterized by the presence of one or several repeats of a 90-110 amino acid-long cysteine-rich globular domain (Sarrias M R et al., 2004, *The Scavenger Receptor Cysteine-Rich (SRCR) Domain: An Ancient and Highly Conserved Protein Module of the Innate Immune System, Crit Rev Immunol* 24:1-38). In mammals, SRCR-SF members are expressed by hemopoietic and non-hemopoietic derived cells, where they display multiple functional capabilities. Although there is no unifying role for all SRCR-SF members, some of them function as PRRs. Such a group includes macrophage (SR-Al, MARCO, CD163, and Spa), epithelial (SCARA5, DMBT1, and S5D-SRCRB), or lymphocyte (CD5 and CD6) receptors (Martinez V G et al., 2011, *The conserved scavenger receptor cysteine-rich superfamily in therapy and diagnosis, Pharmacol Rev* 63:967-1000).

Nowadays, sepsis, severe sepsis and septic shock still remains as an unmet clinical need with an increase in occurrence predicted and a huge socioeconomic burden as a result of population aging, increase in invasive medical procedures, emergence of multidrug-resistant (MDR) bacteria, and increased prevalence of chronic diseases (Okeke E B and Uzonna J E, 2016, *In Search of a Cure for Sepsis: Taming the Monster in Critical Care Medicine, J Innate Immun* 8:156-70). Overall mortality of sepsis and septic shock still remains high (35% and 60%, respectively) despite significant advances in supportive care and availability of potent broad-spectrum antibiotics.

Although antibiotics constitute a necessary part of the treatment of sepsis, they are probably not sufficient to substantially reduce the mortality associated with MOD associated to severe sepsis and septic shock, in particular in view of the raise in MDR bacteria. Urgent innovative developments on cost-effective biological-treatments and/or medical devices, alternative or complementary to antibiotics and supportive care are thus needed.

Adjunctive/alternative therapies to antibiotics include host-directed approaches addressed to potentiate the innate defense mechanisms and/or reverse the immune cell dysfunction associated to sepsis mortality (Delano M J and Ward P A, 2016, *Sepsis-induced immune dysfunction: can immune therapies reduce mortality? J Clin Invest* 126:23-31). The neutralization of pathogenic microbial factors with endogenous host immune constituents represents one such approach. In this regard, some members of the scavenger receptor cysteine-rich superfamily (SRCR-SF) interact with PAMPs both from Gram-negative (lipopolysaccharide, LPS) or Gram-positive (lipoteichoic acid, LTA; and peptidoglycan, PGN) bacteria (Martinez V G, et al., 2011, *The conserved scavenger receptor cysteine-rich superfamily in therapy and diagnosis. Pharmacol Rev* 63:967-1000).

The prototypical member of the SRCR-SF displaying bacterial PAMPs binding properties is Deleted in Malignant Brain Tumors-1 (DMBT-1), also known as Salivary Agglutinin (SAG) or gp340 (Ligtenberg A J M, et al., 2010, *Deleted in malignant brain tumors-1 protein (DMBT1): a pattern recognition receptor with multiple binding sites, Int J Mol Sci* 11:5212-33; Madsen J, et al., 2010, *Gp-340/DMBT1 in mucosal innate immunity, Innate Immun* 16:160-7). DMBT-1/SAG is a soluble glycoprotein containing 14 SRCR, one zona pellucida, and two C1r/C1s Uegf Bmp1 domains. The bacterial-binding properties of DMBT-1/SAG have been accurately mapped within its SRCR domains to a 11-mer consensus peptide sequence (DMBT-1/SAG.pbs1, GRVEVLYRGSW) from which a 9-mer motif (VEVLxxxxW) present in 13 out 14 of them was identified (Bikker F J, et al., 2004, *Bacteria binding by DMBT1/SAG/*

*gp*-340 *is confined to the VEVLXXXXW motif in its scavenger receptor cysteine-rich domains. J Biol Chem* 279:47699-703).

Other SRCR-SF members with bacterial-binding properties include Class A macrophage Scavenger Receptor type I (Peiser L, et al., 2000, *Macrophage class A scavenger receptor-mediated phagocytosis of Escherichia coli: role of cell heterogeneity, microbial* strain, and *culture conditions in vitro Infect Immun* 68:1953-63), Macrophage Receptor with Collagenous structure (MARCO) (Brännström A, et al., 2002, *Arginine residues in domain V have a central role for bacteria-binding activity of macrophage scavenger receptor MARCO. Biochem Biophys Res Commun* 290:1462-9), Soluble protein α (Spα) (Sarrias M R, et al., 2005, *A role for human Sp alpha as a pattern recognition receptor, J Biol Chem* 280:35391-8), CD6 (Sarrias M R et al., 2007, *CD6 binds to pathogen-associated molecular patterns and protects from LPS-induced septic shock, Proc Natl Acad Sci USA* 104:11724-9), CD163 (Fabriek B O, et al., 2009, *The macrophage scavenger receptor CD*163 *functions as an innate immune sensor for bacteria, Blood* 113:887-92), Scavenger Receptor Class A Member 5 (Jiang Y, et al., 2006, *Identification and characterization of murine SCARA5, a novel class A scavenger receptor that is expressed by populations of epithelial cells. J Biol Chem* 281:11834-45), and Soluble Scavenger Receptor Cysteine-Rich group B member with 5 domains (Miró-Julià C, et al., 2011, *Molecular and functional characterization of mouse S5D-SRCRB: a new group B member of the scavenger receptor cysteine-rich superfamily, J Immunol* 186(4):2344-54; Bessa Pereira C, et al., 2016, *The Scavenger Receptor SSc5D Physically Interacts with Bacteria through the SRCR-Containing N-Terminal Domain, Front Immunol* 7:416), even if the bacterial-binding regions have only been functionally mapped for MARCO (Brännström A, et al., 2002, *Arginine residues in domain V have a central role for bacteria-binding activity of macrophage scavenger receptor MARCO, Biochem Biophys Res Commun* 290:1462-9), and CD163 (Fabriek B O, et al., 2009, *The macrophage scavenger receptor CD*163 *functions as an innate immune sensor for bacteria, Blood* 113:887-92).

CD6 is a lymphocyte surface receptor highly homologous to CD5, another lymphocytic member of the SRCR-SF. Both receptors are likely derived by duplication from a common ancestral gene (Lecomte O, et al., 1996, *Molecular linkage of the mouse CD5 and CD6 genes, Immunogenetics* 44:385-90) and are mainly expressed by T cells, and the B1a cell subset involved in the production of natural antibodies. CD6 and CD5 share a similar extracellular region composed by three tandem SRCR domains and a cytoplasmic tail suitable for signal transduction. Indeed, CD6 and CD5 are physically associated to the T-cell receptor (TCR) complex (Gimferrer I, et al., 2004, *Relevance of CD6-mediated interactions in T cell activation and proliferation, J Immunol* 173:2262-70), and play relevant roles in regulating T-cell developmental and activation processes (Santos R F, et al., 2016, *Tuning T Cell Activation: The Function of CD6 at the Immunological Synapse and in T Cell Responses, Curr Drug Targets* 17:630-9; Soldevila G, et al., 2011, *The immunomodulatory properties of the CD5 lymphocyte receptor in health and disease, Curr Opin Immunol* 23:310-8). Binding of rshCD6 to bacterial PAMPs such as LPS, LTA or PGN takes place with $K_d$ affinities in the nM range, similar to CD14's binding affinity to the same PAMPs (Dziarski R, et al., 1998, *Binding of bacterial peptidoglycan to CD*14, *J Biol Chem* 273:8680-90; Tobias P S, et al., 1995, *Lipopolysaccharide binding protein-mediated complexation of lipopolysaccharide with soluble CD*14, *J Biol Chem* 270:10482-8). Moreover, rshCD6 down-modulates the pro-inflammatory cytokine (IL-1β, IL-6, TNF-α) release triggered by LPS or LTA/PGN (Martinez-Florensa M, et al., 2014, *Targeting of key pathogenic factors from gram-positive bacteria by the soluble ectodomain of the scavenger-like lymphocyte receptor CD6, J Infect Dis* 209:1077-86).

The prophylactic infusion of a recombinant soluble form of human CD6 (rshCD6) significantly reduces mortality and serum levels of pro-inflammatory cytokines (IL-1β, IL-6 and TNF-α) in mouse models of septic shock induced by G+ and G− bacterial endotoxins (LTA+PGN, and LPS, respectively), whole alive bacteria (*Staphylococcus aureus, Acinetobacter baumannii*) independently of their MDR phenotype (Methicillin-resistant *S. aureus*, Colistin-resistant *A. baumanii*) as well as mono- and poly-microbial models of peritonitis (Martinez-Florensa M, et al., 2017, *Effects of Human and Mouse Soluble Scavenger-Like CD*6 Lymphocyte Receptor in a Lethal Model of Polymicrobial Sepsis, Antimicrob Agents Chemother 61:*e*01391-16; Martinez-Florensa M, et al., 2014. *Targeting of key pathogenic factors from gram-positive bacteria by the soluble ectodomain of the scavenger-like lymphocyte receptor CD6, J Infect Dis* 209:1077-1086; Sarrias M R, et al., 2007, CD6 *binds to pathogen-associated molecular patterns and protects from LPS-induced septic shock, Proc Natl Acad Sci USA* 104:11724-9).

EP 2143436 discloses that intraperitoneal (i.p.) administration of rshCD6 counteracts the lethal effects caused by LPS-induced septic shock in mice, and that CD6 has therapeutic potential for the intervention of septic shock syndrome and of other inflammatory diseases related to infectious diseases.

However, the production of mammalian recombinant proteins is a relatively complex process, which should ideally rend a protein with the correct folding and post-translational modifications, if any. The process usually involves cloning the desired gene in a mammalian expression vector, transferring the recombinant gene in a mammalian cell system (e.g., CHO cells) and purifying the protein by chromatography procedures. This process has certain limitations such as low production efficiencies and high costs. Therefore, it seems desirable to provide effective compounds and compositions for the prevention and treatment of infectious diseases and of inflammatory conditions related to these infectious diseases, such as sepsis, which are easier and thus cheaper to produce.

SUMMARY OF THE INVENTION

The present application discloses an amino acid sequence comprising or, alternatively, consisting of, SEQ ID No.: 3, and/or SEQ ID No.: 1, and/or SEQ ID No.: 2, or a derivative thereof.

The present application further discloses a process for the preparation of the amino acid sequences and/or peptides of the invention. The process is carried out by solid phase peptide synthesis or by peptide synthesis in solution. The solid phase peptide synthesis includes the following steps:

a) solid phase peptide synthesis,
b) cleaving the peptide from the polymer support,
c) optionally, cycling the peptide in solution, and
d) eliminating the protecting groups or alternatively i) solid phase peptide synthesis,
ii) optionally, solid phase peptide cycling, and iii) cleaving the peptide from the polymer support and simultaneously eliminating the protecting groups.

In addition, the present application discloses a composition comprising one or more of the amino acid sequences of the present invention.

In a further embodiment, the present application discloses a pharmaceutical composition comprising the composition of the present invention together with pharmaceutically acceptable carriers, pharmaceutically acceptable salts, adjuvants and/or suitable excipients.

In a further embodiment, the present application discloses a conjugate comprising the amino acid sequences of the invention, preferably a conjugate wherein one or more of the amino acid sequences of the invention are conjugated (preferably covalently linked) to a carrier, preferably an insoluble carrier, more preferably an insoluble polymer.

In a further embodiment, the present application discloses a kit-of-parts comprising one or more of the amino acid sequences of the present invention and an antibiotic, preferably Imipenem.

The present application further provides the one or more of amino acid sequences of the present invention, the composition of the present invention or the kit-of-parts of the present invention for use as a medicament, in particular for use in a therapeutic and/or preventive method of treatment, in a mammal including a human, of an infectious disease, or of an inflammatory condition related to an infectious disease, or of an inflammatory disease related to the presence of a product derived from an infectious agent.

Further provided is a device for selective binding and separation of at least one component from an aqueous solution wherein the device comprises one or more of amino acid sequences of the present invention.

In addition, the present application discloses a method for the removal of at least one component from an aqueous solution, said method comprising:

providing an aqueous solution that potentially contains said at least one component, passing the aqueous solution through the device of the present invention under conditions which effect the binding of said at least one component to the one or more amino acid sequences comprised in the device, thus removing the at least one component from the aqueous solution.

BRIEF DESCRIPTION OF THE FIGURES

FIG. 1A-C. Structural characteristics and amino acid conservation of CD6 peptides. FIG. 1A: Amino acid sequence, molecular weight (M.W.) and isoelectric point (pI) of the CD5, CD6 and DMBT-1 peptides and proteins analyzed (i.e., SEQ ID NOs: 1, 2, 3, 6, 7, 8, and 9). FIG. 1B: Three-dimensional surface representations of the extracellular region of human CD6 displaying the relative position of the CD6 peptides in study (colored dark grey). FIG. 1C: Amino acid sequence alignment of CD6-derived peptides in study from primate (*Homo sapiens, Macaca mulatta, Nomascus Leucogenys, Pan troglodytes, Tarsius syrichta*) rodent (*Mus musculus, Rattus norvegicus, Oryctolagus cuniculus, Mesocricetus auratus*), fish (*Poeciliopsis prolifica, Salmo solar*), bovine (*Bos Taurus*), pig (*Sus scrofa*), and reptile (*Alligator mississippiensis*) species. Amino acid identities are highlighted in grey (i.e., SEQ ID NOs: 1, 2, and 3).

DETAILED DESCRIPTION OF THE INVENTION

Amino Acid Sequences and Peptides

Figures 1A, 1B:
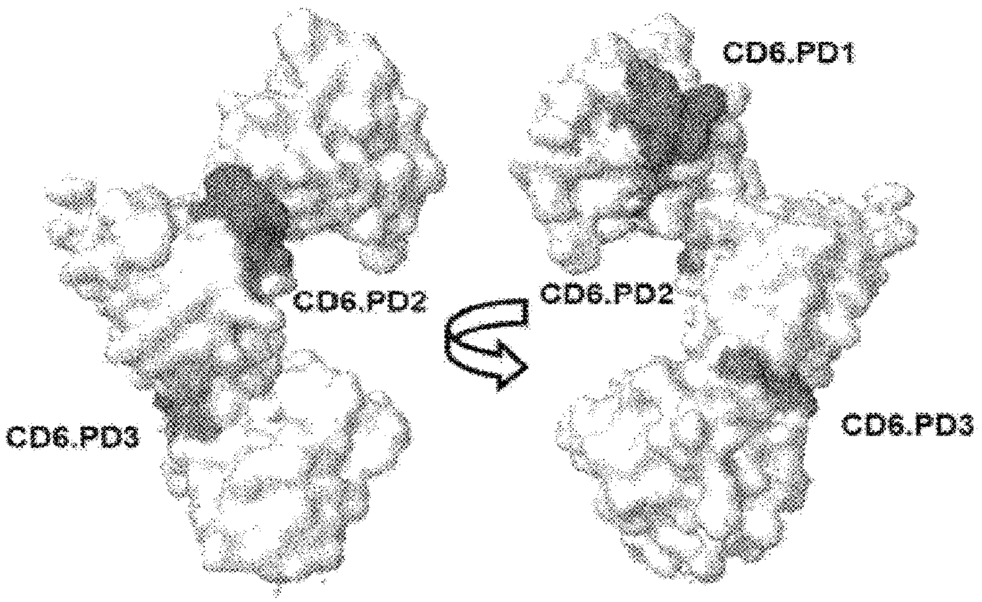

In a first aspect, the present invention provides an amino acidic sequence comprising or, alternatively, consisting of one or more of the following sequences ("the amino acid sequences of the present invention"), or a derivative thereof:

```
                                 (SEQ ID NO.: 1)
CD6.PD1:          GTVEVRLEASW;

                                 (SEQ ID NO.: 2)
CD6.PD2:          GRVEMLEHGEW;
and

                                 (SEQ ID NO.: 3)
CD6.PD3:          GQVEVHFRGVW.
```

Preferably, the present invention provides one or more of the following peptides ("the peptides of the present invention"), or a derivative thereof:

```
                                 (SEQ ID NO.: 1)
CD6.PD1:          GTVEVRLEASW;

                                 (SEQ ID NO.: 2)
CD6.PD2:          GRVEMLEHGEW;
and

                                 (SEQ ID NO.: 3)
CD6.PD3:          GQVEVHFRGVW.
```

In a preferred embodiment, the present invention provides an amino acidic sequence comprising or, alternatively, consisting of GQVEVHFRGVW (SEQ ID NO.: 3, CD6.PD3), or a derivative thereof. In a preferred embodiment, the present invention provides the CD6.PD3 peptide (GQVEVHFRGVW, SEQ ID NO.: 3), or a derivative thereof.

In a further embodiment, the present invention provides an amino acidic sequence comprising or, alternatively, consisting of GTVEVRLEASW (SEQ ID NO.: 1, CD6.PD1), or a derivative thereof. In a preferred embodiment, the present invention provides the CD6.PD1 peptide (GTVEVRLEASW, SEQ ID NO.: 1), or a derivative thereof.

In a further embodiment, the present invention provides an amino acidic sequence comprising or, alternatively, consisting of GRVEMLEHGEW (SEQ ID NO.: 2, CD6.PD2), or a derivative thereof. In a preferred embodiment, the present invention provides the CD6.PD2 peptide (GRVEMLEHGEW, SEQ ID NO.: 2), or a derivative thereof.

These peptides are conserved short 11-mer peptides mapping at extracellular SRCR domains of human CD6. The ectodomain of CD6 is composed of three SRCR domains, the intervening sequences and a stalk region.

The present invention further provides amino acid sequences comprising the peptides CD6.PD1 (SEQ ID NO.: 1), CD6.PD2 (SEQ ID NO.: 2) and/or CD6.PD3 (SEQ ID NO.: 3). The amino acid sequence can be linear or cyclic. Preferably, the amino acid sequence is comprised within the ectodomain of human CD6. In a preferred embodiment, the amino acidic sequence is comprised within SEQ ID NO.: 4. In particular embodiment, the linear or cyclic amino acidic sequence comprises between 12 and 17 adjacent amino acids comprising the peptides CD6.PD1 (SEQ ID NO.: 1), CD6.PD2 (SEQ ID NO.: 2) or CD6.PD3 (SEQ ID NO.: 3) and is preferably comprised within SEQ ID NO.: 4. Examples of preferred amino acidic sequences include, but are not limited to:

(SEQ ID NO.: 13)
CSGTVEVRLEASWEPAC, (SEQ ID NO.: 14)
SGTVEVRLEASWEPA, (SEQ ID NO.: 15)
SGTVEVRLEASWEP, (SEQ ID NO.: 16)
SGTVEVRLEASWE, (SEQ ID NO.: 17)
SGTVEVRLEASW, (SEQ ID NO.: 18)
GTVEVRLEASWEPA, (SEQ ID NO.: 19)
GTVEVRLEASWEP, (SEQ ID NO.: 20)
GTVEVRLEASWE, (SEQ ID NO.: 21)
CAGRVEMLEHGEWGSVC, (SEQ ID NO.: 22)
AGRVEMLEHGEWGSV, (SEQ ID NO.: 23)
AGRVEMLEHGEWGS, (SEQ ID NO.: 24)
AGRVEMLEHGEWG, (SEQ ID NO.: 25)
AGRVEMLEHGEW, (SEQ ID NO.: 26)
GRVEMLEHGEWGSV, (SEQ ID NO.: 27)
GRVEMLEHGEWGS, (SEQ ID NO.: 28)
GRVEMLEHGEWG, (SEQ ID NO.: 29)
CEGQVEVHFRGVWNTVC, (SEQ ID NO.: 30)
EGQVEVHFRGVWNTV, (SEQ ID NO.: 31)
EGQVEVHFRGVWNT, (SEQ ID NO.: 32)
EGQVEVHFRGVWN, (SEQ ID NO.: 33)
EGQVEVHFRGVW, (SEQ ID NO.: 34)
GQVEVHFRGVWNTV, (SEQ ID NO.: 35)
GQVEVHFRGVWNT, (SEQ ID NO.: 36)
GQVEVHFRGVWN.

As used herein, the expression "derivative of an amino acid sequence or peptide of the present invention" includes any derivative of the amino acid sequence or peptide of the present invention able to perform the biological function, e.g., any derivative of the amino acid sequence or peptide of the present invention able to bind PAMPs broadly distributed among Gram-negative (G−) (e.g., LPS) and Gram-positive (G+) (e.g., LTA) bacteria. The amino acid sequences and peptides of the invention may include modifications of the given sequence. Such modifications are well known to those skilled in the art. The shifting of substituents within an amino acid residue, from a C atom to an N atom, to produce peptoids having greater resistance to proteolysis, and other modifications, are known and are included within the scope of this invention. For instance, one or more of the L-amino acids of the amino acid sequences and peptides of the present invention may be replaced by a D-amino acid in order to increase their stability. For instance, N-acylation and/or C-amidation or C-esterification of the peptides and/or amino acid sequences of the present invention may increase their resistance to proteolysis. For instance, cyclization of the one or more of the amino acid sequences and/or peptides of the present invention may increase their stability and permeability. For instance, one or more of the amino acids of the amino acid sequences and/or peptides of the present invention may be N-alkylated (generally N-methylated) in order to improve their stability. For instance, the one or more amino acid sequences and/or peptides of the present invention may be conjugated to one or more macromolecules (e.g., polyethylene glycol (PEG), albumin), in order to improve their stability and/or reduce renal clearance. For instance, the amino acid sequences and peptides of the present invention may comprise the N- or C-terminus capped with Cys residues, for further covalent binding to a solid-phase (e.g., polypropylene beads).

SEQ ID NO: 4 corresponds to a mature (fully processed) soluble isoform of human CD6. The sequence of human CD6 receptor is the one identified with the accession number P30203 (CD6_HUMAN, Last modified Dec. 15, 2009. Version 3 in the UniProtKB/Swiss-Prot database), which corresponds to the receptor in the membrane-bound isoform. It has not yet been fully determined if the soluble isoform of CD6 is also generated by proteolytical cleavage; SEQ ID NO. 4 is obtained by the addition of a stop codon in the stalk region that precedes the transmembrane region.

SEQ ID NO.: 4:
DQLNTSSAESELWEPGERLPVRLTNGSSSCSGTVEVRLEASWEPACGALW

DSRAAEAVCRALGCGGAEAASQLAPPTPELPPPPAAGNTSVAANATLAGA

PALLCSGAEWRLCEVVEHACRSDGRRARVTCAENRALRLVDGGGACAGRV

EMLEHGEWGSVCDDTWDLEDAHVVCRQLGCGWAVQALPGLHFTPGRGPIH

RDQVNCSGAEAYLWDCPGLPGQHYCGHKEDAGVVCSEHQSWRLTGGADRC

EGQVEVHFRGVWNTVCDSEWYPSEAKVLCQSLGCGTAVERPKGLPHSLSG

RMYYSCNGEELTLSNCSWRFNNSNLCSQSLAARVLCSASRSLHNLSTPEV

PASVQTVTIESSVTVKIENKESR

SEQ ID NO: 4 results from the transcription and translation of nucleotide sequences comprising SEQ ID NO.: 5.

SEQ ID NO.: 5:
gaccagctca acaccagcag tgcagagagt gagctctggg agccagggga gcggcttccg gtccgtctga caaacgggag cagcagctgc agcgggacgg tggaggtgcg gctcgaggcg tcctgggagc ccgcgtgcgg ggcgctctgg gacagccgcg ccgccgaggc cgtgtgccga gcactgggct gcggcggggc ggaggccgcc tctcagctcg ccccgccgac ccctgagctg -continued

```
ccgcccccgc ctgcagccgg gaacaccagc gtagcagcta
atgccactct ggccggggcg cccgccctcc tgtgcagcgg
cgccgagtgg cggctctgcg aggtggtgga gcacgcgtgc
cgcagcgacg ggaggcgggc ccgtgtcacc tgtgcagaga
accgcgcgct gcgcctggtg gacggtggcg gcgcctgcgc
cggccgcgtg gagatgctgg agcatggcga gtggggatca
gtgtgcgatg acacttggga cctggaggac gcccacgtgg
tgtgcaggca actgggctgc ggctgggcag tccaggccct
gcccggcttg cacttcacgc ccggccgcgg gcctatccac
cgggaccagg tgaactgctc gggggccgaa gcttacctgt
gggactgccc ggggctgcca ggacagcact actgcggcca
caaagaggac gcgggcgtgg tgtgctcaga gcaccagtcc
tggcgcctga caggggggcgc tgaccgctgc gaggggcagg
tggaggtaca cttccgaggg gtctggaaca cagtgtgtga
cagtgagtgg tacccatcgg aggccaaggt gctctgccag
tccttgggct gtggaactgc ggttgagagg cccaaggggc
tgccccactc cttgtccggc aggatgtact actcatgcaa
tggggaggag ctcaccctct ccaactgctc ctggcggttc
aacaactcca acctctgcag ccagtcgctg gcagccaggg
tcctctgctc agcttcccgg agtttgcaca atctgtccac
tcccgaagtc cctgcaagtg ttcagacagt cactatagaa
tcttctgtga cagtgaaaat agagaacaag gaatctcggt ag
```

Figure 3:
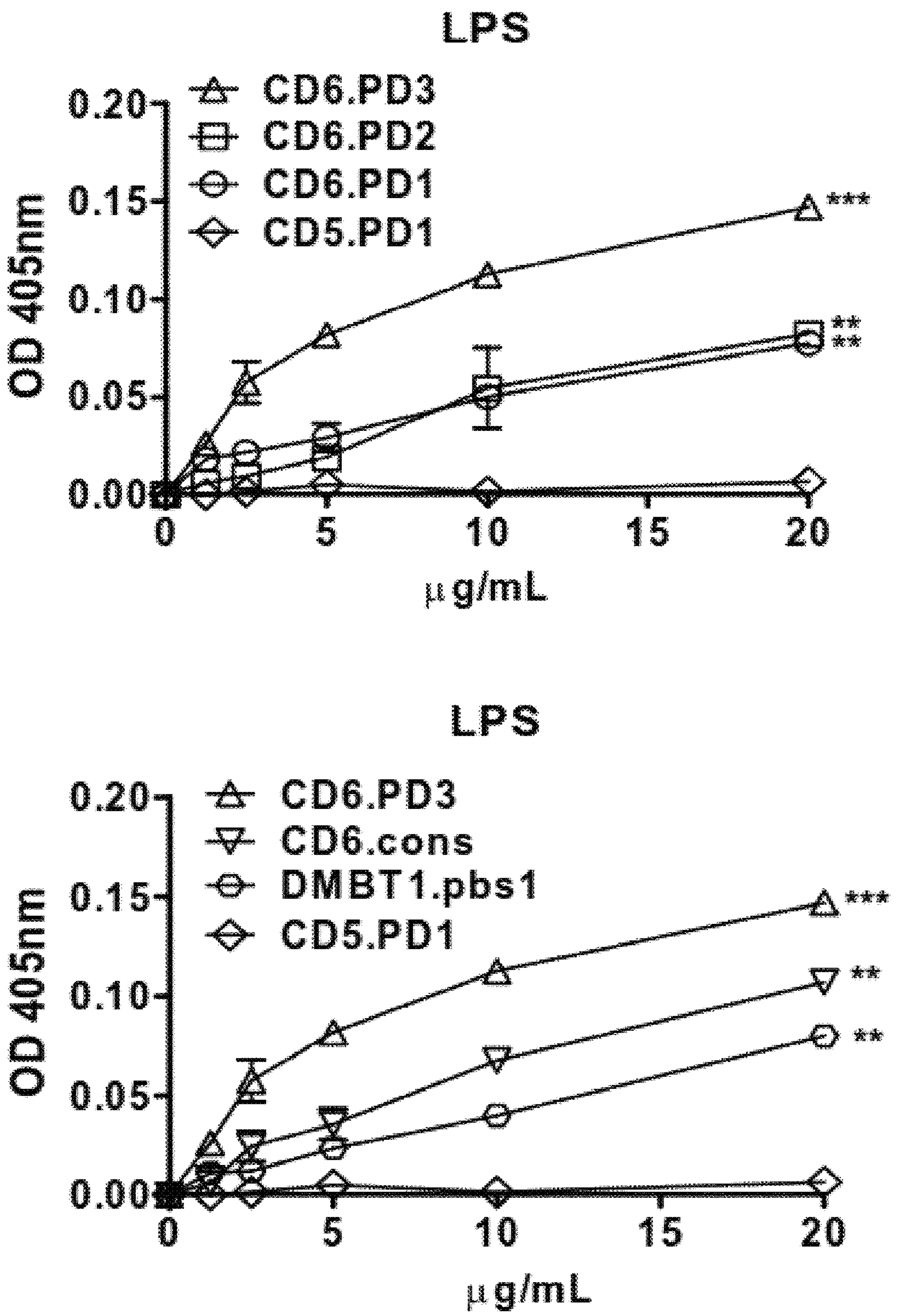
FIG. 3. Binding of biotin-labeled CD6-derived peptides to immobilized PAMPs from Gram- and Gram+ origin. Increasing concentrations (5-20 μg/mL) of biotin-labeled CD6-(PD1, PD2, PD3 and cons), DMBT1-(pbs1), and CD5-(PD1) derived peptides were added to 96-well ELISA plates sensitized with *E. coli* 0111:B4 LPS (A) or *S. aureus* LTA (B) (5 μg/mL each in PBS). Following overnight incubation at 4° C. bound peptides or proteins were developed by addition of horseradish peroxidase (HRP)-labeled streptavidin and 3,3',5,5'-tetramethylbenzidine (TMB) substrate and further readings at OD 405-620 nm. Results are expressed as mean±SD of duplicates from one representative experiment of three performed. Statistical analysis was performed by two-way ANOVA (*,P<0.05; , P<0.01; *, P<0.001).
Figure 3:
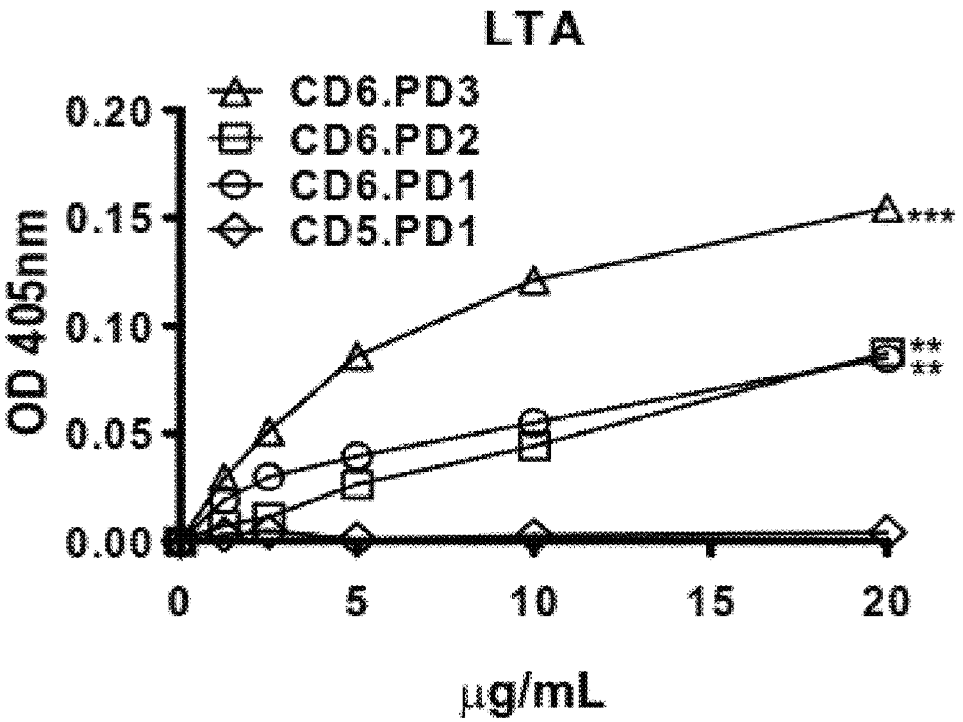
Figure 3:
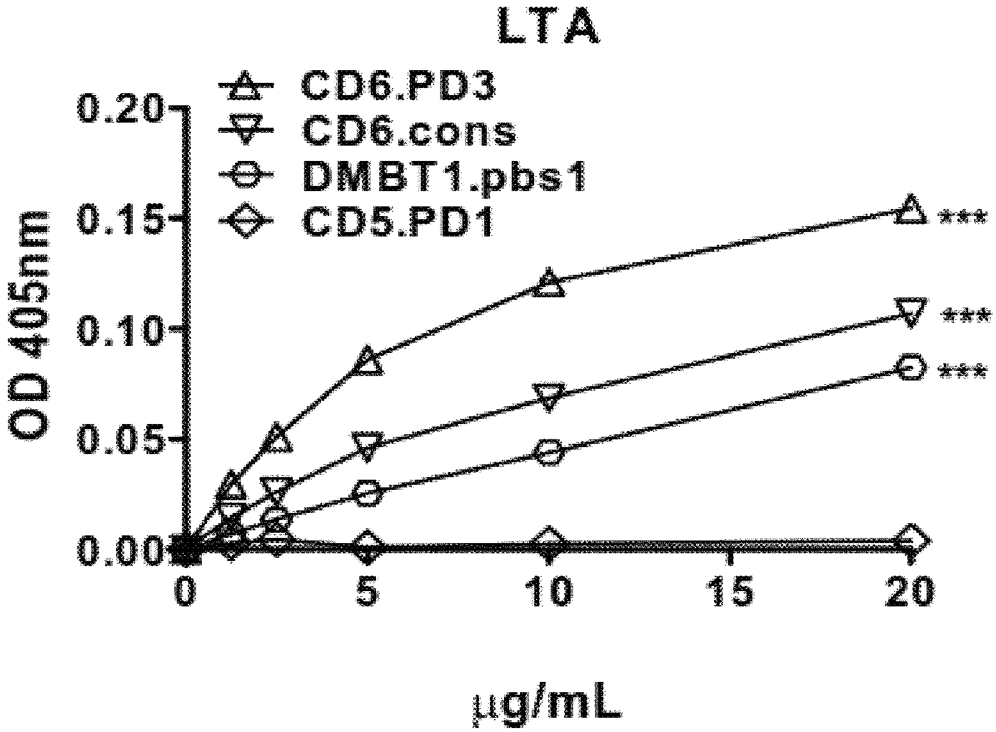
Figure 7:
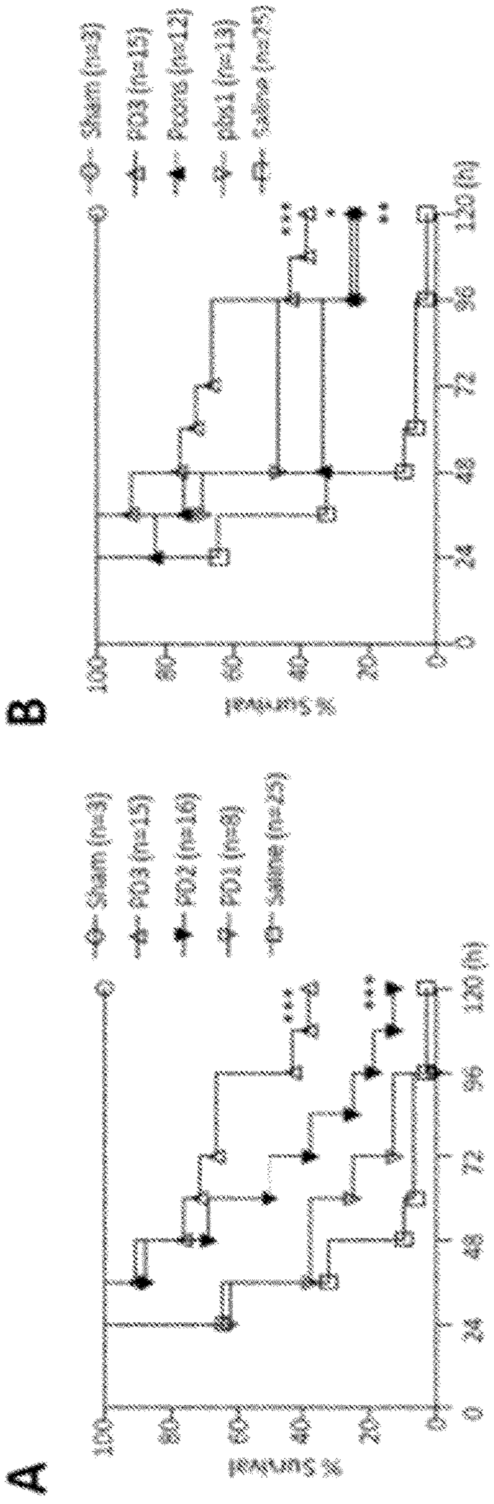
FIG. 7. Comparative therapeutic effects of i.v. infused CD6-derived peptides on mouse survival following Cecal Ligation and Puncture (CLP)-induced sepsis. (A, B) C57BL/6J mice were i.v. infused with saline (n=25) or single 6 mg/kg doses of unlabeled CD6-(PD1, n=8; PD2, n=16; PD3, n=15; Pcons, n=12) or DMBT1 (pbs1, n=13) derived peptides at +1 h post CLP induction. A sham group (n=3) was included. In all cases average percent survival was analyzed over time for each group and compared with the saline-treated group using the long-rank t-test (*, P<0.05; , P<0.01; *, P<0.001).
Figure 8:
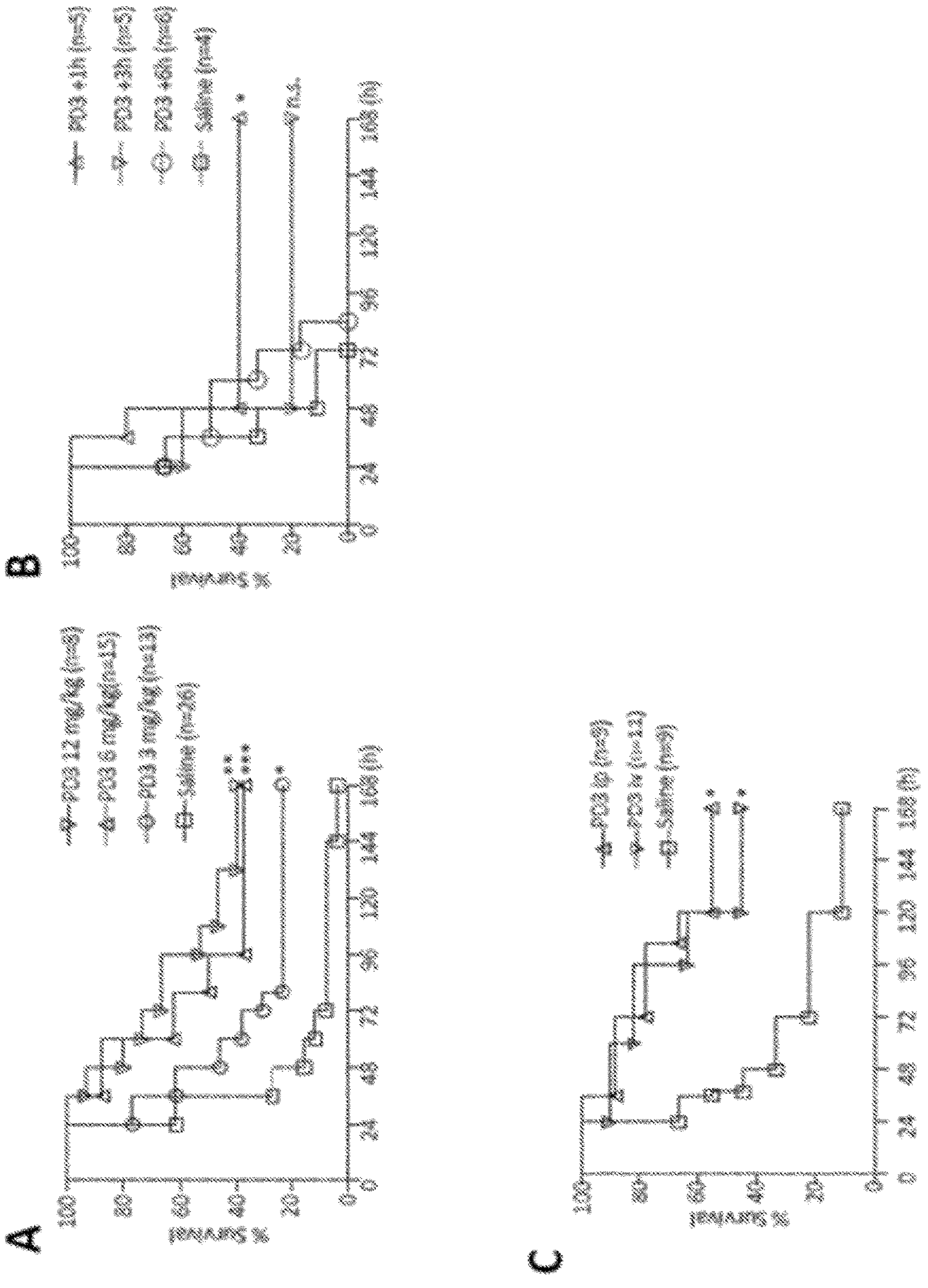
FIG. 8. Dose-, time- and via-dependent effects of CD6.PD3 infusion on mouse survival following CLP-induced sepsis. (A) C57BL/6 mice were i.v. infused at +1 h post CLP with saline (n=26) or single increasing doses (3 mg/kg, n=13; 6 mg/kg, n=15; and 12 mg/kg, n=8) of CD6.PD3 peptide. (B) C57BL/6 mice were i.v. infused with saline (n=4) or 6 mg/kg CD6.PD3 at different times post CLP (+1 h, n=5; +3 h, n=5; +6 h, n=6). (C) C57BL/6J mice were i.v. (n=11) or i.p. (n=9) infused with 6 mg/kg CD6.PD3 peptide or saline (n=9) at +1 h post CLP. In all cases, average percent of survival was analyzed over time and compared with the saline-treated group using a log-rank t-test (n.s., not significant; *, P<0.05. , P<0.01; *, P<0.001).
Figure 9:
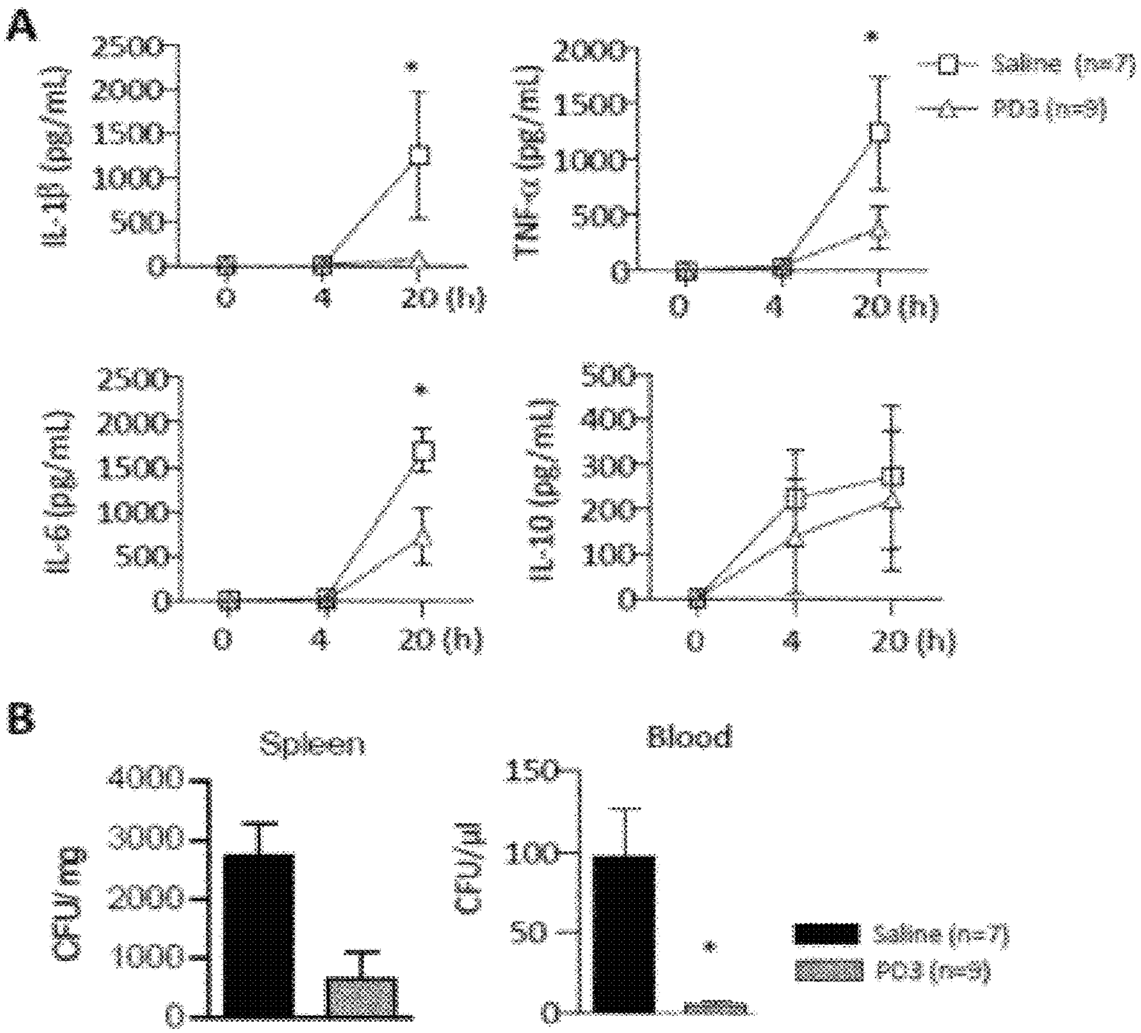
FIG. 9. Therapeutic effect of CD6.PD3 infusion on cytokine and bacterial load levels following CLP-induced sepsis. (A) C57BL/6J mice were i.v. infused at +1 h post CLP with saline (n=7) or CD6.PD3 peptide (6 mg/kg; n=9), and cytokine plasma levels were monitored by ELISA at different time points (4 h and 20 h) thereafter. Data are expressed as mean±SD. (B) Same mouse groups as in (A) were monitored for blood and spleen bacterial load at 20 h following CLP induction. Data are expressed as mean±SD of CFU/mg (spleen) or CFU/μL (blood). In all cases, statistical differences were evaluated using a 2-tailed Student t-test (*, P<0.05).

CD6.PD1 (also referred to in the present document as "PD1" or "P1"), CD6.PD2 (also referred to in the present document as "PD2" or "P2") and CD6.PD3 (also referred to in the present document as "PD3" or "P3") are able to bind PAMPs broadly distributed among Gram-negative (G−) (e.g., LPS) and Gram-positive (G+) (e.g., LTA) bacteria (see, e.g., FIG. 3). They also show high bacterial-agglutination properties. In particular, PD1 and PD2 show a very high affinity towards Re-LPS and LTA (see, e.g., FIG. 4). CD6.PD3 improves the survival of mice undergoing poly-microbial sepsis in a dose- and time-dependent manner (see FIGS. 7, 8 and 9). When combined with the antibiotic Imipenem/Cilastatin this peptide performs even better (see, e.g., FIG. 10), showing additive survival effects on septic mice.

Any method commonly used in the art can be employed to produce the amino acid sequences and peptides, or derivatives thereof, of the present invention (CD6.PD1, CD6.PD2 and CD6.PD3). For instance, they can be produced by solid-phase peptide synthesis (Albericio F and Kates S A, 2000, Solid-Phase Synthesis: A Practical Guide, CRC Press, ISBN 9780824703592).

The compounds of the invention (amino acid sequences and peptides, and derivatives thereof as described above), their stereoisomers or their pharmaceutically acceptable salts can be synthesized according to conventional methods known in the state of the art. In an embodiment of the present invention, the compounds are synthesized by means of solution or solid phase peptide synthesis methods.

The solid phase synthesis methods are described for example in [Stewart J. M. and Young J. D., 1984, "Solid Phase Peptide Synthesis, 2nd edition" Pierce Chemical Company, Rockford, Illinois; Bodanzsky M., and Bodanzsky A., 1984 "The practice of Peptide Synthesis" Springer Verlag, New Cork; Lloyd-Williams P., Albericio F. and Giralt E. (1997) "Chemical Approaches to the Synthesis of Peptides and Proteins" CRC, Boca Raton, FL, USA]. Solution synthesis methods and combinations of the solution and solid phase synthesis methods or enzymatic synthesis are described in [Kullmann W. et al., J. Biol. Chem., 1980, 255, 8234-8238].

In an embodiment of the present invention, the compounds of the invention (amino acid sequences and peptides, and derivatives thereof as described above) are prepared by means of a method comprising the steps of:

a) Solid phase peptide synthesis
b) Cleaving the peptide from the polymer support, preferably by means of acid treatment
c) Optionally, cycling the peptide in solution
d) If needed, eliminating the protecting groups, preferably with trifluoroacetic acid or alternatively
i) Solid phase peptide synthesis
ii) Optionally, solid phase peptide cycling
iii) Cleaving the peptide from the polymer support and, if needed, simultaneously eliminating the protecting groups, preferably by means of treatment with trifluoroacetic acid.

Preferably, the C-terminal end is bound to a solid support and the process is developed in solid phase and therefore comprises coupling an amino acid with the N-terminal end protected and the C-terminal end free on an amino acid with the N-terminal end free and the C-terminal end bound to a polymer support; eliminating the protecting group from the N-terminal end; and repeating this sequence as many times as needed to thus obtain the target peptide sequence, followed finally by cleaving the synthesized peptide from the original polymer support. The functional groups of the amino acid side chains are maintained suitably protected with temporary or permanent protecting groups throughout synthesis, and they can be deprotected simultaneously or orthogonally to the process of cleaving the peptide from the polymer support.

Alternatively, the solid phase synthesis can be performed by means of a convergent strategy by coupling a peptide fragment on the polymer support or on a peptide fragment previously bound to the polymer support. Convergent synthesis strategies are well known by persons skilled in the art and are described by Lloyd-Williams P. et al. in Tetrahedron 1993, 49, 11065-11133.

The process can comprise the additional steps of deprotecting the N-terminal and C-terminal ends and/or cleaving the peptide from the polymer support in an indistinct order, using standard processes and conditions known in the art, after which the functional groups of said ends can be modified. The optional modification of the N-terminal and C-terminal ends can be performed with the peptide of formula (I) anchored to the polymer support or once the peptide has been cleaved from the polymer support.

The term "protecting group" relates to a group which blocks an organic functional group and which can be removed under controlled conditions. The protecting groups, their relative reactivities and the conditions in which they remain inert are known by the person skilled in the art.

Examples of representative protecting groups for the amino group are the amides, such as amide acetate, amide benzoate, amide pivalate; carbamates, such as benzyloxycarbonyl (Cbz or Z), 2-chlorobenzyl (ClZ), para-nitrobenzyloxycarbonyl (pNZ), Cert-butyloxycarbonyl (Boc), 2,2,2-trichloroethoxycarbonyl (Troc), 2-(trimethylsilyl) ethoxycarbonyl (Teoc), 9-fluorenylmethoxycarbonyl (Fmoc) or allyloxycarbonyl (Alloc), trityl (Trt), methoxytrityl (Mtt), 2,4-dinitrophenyl (Dnp), N-[1-(4,4-dimethyl-2,6-dioxocyclohex-1-ylidene)ethyl](Dde), 1-(4,4-dimethyl-2,6-dioxo-cyclohexylidene)-3-methyl-butyl (ivDde), 1-(1-adamantyl)-1-methylethoxy-carbonyl (Adpoc), among others; preferably, Boc or Fmoc.

Examples of representative protecting groups for the carboxyl group are the esters, such as the Cert-butyl (tBu) ester, allyl (All) ester, triphenylmethyl ester (trityl ester, Trt), cyclohexyl (cHx) ester, benzyl (Bzl) ester, ortho-nitrobenzyl ester, para-nitrobenzyl ester, para-methoxybenzyl ester, trimethylsilylethyl ester, 2-phenylisopropyl ester, fluorenylmethyl (Fm) ester, 4-(N4-[1-(4,4-dimethyl-2,6-dioxocyclohexylidene)-3-methylbutyl]amino)benzyl (Dmab) ester, among others; preferred protecting groups of the invention are All, tBu, cHex, Bzl and Trt esters.

The trifunctional amino acids can be protected during the synthetic process with temporary or permanent protecting groups orthogonal to the protecting groups of the N-terminal and C-terminal ends. The amino group protecting groups described above are used to protect the amino group of the lysine side chain, the tryptophan side chain can be protected with any of the amino group protecting groups described above, or it may not be protected, the serine and threonine side chain is protected with Cert-butyl (tBu) ester, the cysteine side chain is protected with a protecting group selected from the group consisting of trityl and acetamidomethyl and the asparagine side chain can be protected with a protecting group selected from the group consisting of methoxytrityl, trityl and xanthyl or it may not be protected. Preferred trifunctional amino acid protecting groups of the invention are tBu esters in the serine and threonine side chains; Boc in the lysine side chains, Trt in the cysteine side chains and Fmoc or Boc as a temporary protecting group of the N-terminal end.

Examples of these and other additional protecting groups, their introduction and their removal, are described in the literature [Greene T. W. and Wuts P. G. M., (1999) "Protective groups in organic synthesis" John Wiley & Sons, New York; Atherton B. and Sheppard R. C. (1989) "Solid Phase Peptide Synthesis: A practical approach" IRL Oxford University Press]. The term "protecting groups" also includes the polymer supports used in the solid phase synthesis.

When the synthesis is performed partially or entirely in solid phase, the polystyrene, polyethyleneglycol grafted in polystyrene supports and the like, can be mentioned as solid supports to be used in the process of the invention such as, by way of non-limiting example, p-methylbenzhydrylamine (MBHA) resins [Matsueda G. R. et al., Peptides 1981, 2, 45-50], 2-chlorotrityl resins [Barlos K. et al. 1989 Tetrahedron Lett. 30:3943-3946; Barlos K. et al., 1989 Tetrahedron Lett. 30, 3947-3951], TentaGel® resins (Rapp Polymere GmbH), ChemMatrix® resins (Matrix Innovation, Inc) and the like, which may or may not include a labile linker, such as acid (PAL) [Albericio F. et al., 1990, J. Org. Chem. 3730-3743], the 2-[4-aminomethyl-(2,4-dimethoxyphenyl)] phenoxyacetic acid (AM) [Rink H., 1987, Tetrahedron Lett. 28, 3787-3790], Wang [Wang S. S., 1973, J. Am. Chem. Soc. 95, 1328-1333] and the like, which allow cleaving the semi-protected peptide and forming the cycle in solution with a step of deprotecting in solution or solid phase cycling and subsequently deprotecting and simultaneously cleaving the peptide.

Combination

In a second aspect, the present invention provides a combination comprising one or more of the amino acidic sequences or the peptides, or derivatives thereof, of the present invention and at least one antibiotic. Preferably, the antibiotic is a beta-lactam antibiotic, more preferably Imipenem. In a preferred embodiment, the combination further comprises an enzyme inhibitor such as a dehydropeptidase inhibitor or a beta-lactamase inhibitor, more preferably Cilastatin. Even more preferably, the combination comprises Imipenem and Cilastatin.

Other antibiotics can be used in the combination of the present invention. Examples of other beta-lactam antibiotics are carbapenems such as meropenem, ertapenem, doripenem, penicillins such amoxicillin, ampicillin, propicillin, oxacillin, dicloxacillin, flucloxacillin, mezlocillin, piperacillin, etc. Examples of other classes of antibiotics include aminoglycosides such as streptomycin, gentamycin, tobramycin, netilmicin, amikacin, etc.; tetracyclines such as tetracycline, doxycycline, minocycline, chlortetracycline, oxytetracycline, demeclocycline, lymecycline, meclocycline, methacycline, minocycline, rolitetracycline, etc., and quinolones such as flumequine (Flubactin), oxolinic acid (Uroxin), rosoxacin (Eradacil), ciprofloxacin (Zoxan, Ciprobay, Cipro, Ciproxin), fleroxacin (Megalone, Roquinol), lomefloxacin (Maxaquin), nadifloxacin (Acuatim, Nadoxin, Nadixa), norfloxacin (Lexinor, Noroxin, Quinabic, Janacin), ofloxacin (Floxin, Oxaldin, Tarivid), pefloxacin (Peflacine), rufloxacin (Uroflox), balofloxacin (Baloxin), grepafloxacin (Raxar), levofloxacin (Cravit, Levaquin), pazufloxacin (Pasil, Pazucross), sparfloxacin (Zagam), temafloxacin (Omniflox), clinafloxacin, gatifloxacin (Zigat, Tequin) (Zymaropth), moxifloxacin (Avelox,Vigamox), sitafloxacin (Gracevit), prulifloxacin (Quisnon) and besifloxacin (Besivance), preferably fluoroquinolones. Glycopeptide antibiotics such as vancomycin, teicoplanin or telavancin, or macrolide antibiotics such as erythromycin, spiramycin, roxithromycin, clarithromycin or azithromycin, among others, are also contemplated.

The combination can also comprise other beta-lactamase inhibitors, such as clavulanic acid, sulbactam, tebipenem, 6-Methylidene Penem2, tazobactam, avibactam or relebactam.

Common combinations of beta-lactam antibiotics and beta-lactamase inhibitors are, for instance, ampicillin/sulbactam, amoxicillin/clavulanate or piperacillin/tazobactam.

In a preferred embodiment, the combination of the present invention comprises an amino acidic sequence comprising or, alternatively, consisting of CD6.PD3 (GQVEVHFRGVW, SEQ ID NO.: 3), or a derivative thereof, and at least one antibiotic, preferably Imipenem, preferably also comprising an enzyme inhibitor such as a dehydropeptidase inhibitor or a beta-lactamase inhibitor, more preferably Cilastatin.

In another embodiment, the combination of the present invention comprises an amino acidic sequence comprising or, alternatively, consisting of CD6.PD1 (GTVEVRLEASW, SEQ ID NO.: 1), or a derivative thereof, and at least one antibiotic, preferably Imipenem, preferably also comprising an enzyme inhibitor such as a dehydropeptidase inhibitor or a beta-lactamase inhibitor, more preferably Cilastatin.

In further embodiment, the combination of the present invention comprises an amino acidic sequence comprising or, alternatively, consisting of CD6.PD2 (GRVEMLEHGEW, SEQ ID NO.: 2), or a derivative thereof, and at least one antibiotic, preferably Imipenem, preferably also comprising an enzyme inhibitor such as a dehydropeptidase inhibitor or a beta-lactamase inhibitor, more preferably Cilastatin.

In a further embodiment, the combination of the present invention comprises an amino acidic sequence comprising or, alternatively, consisting of CD6.PD2 (GRVEMLEHGEW, SEQ ID NO.: 2), or a derivative thereof, an amino acidic sequence comprising or, alternatively, consisting of CD6.PD1 (GTVEVRLEASW, SEQ ID NO.: 1), or a derivative thereof, and at least one antibiotic, preferably Imipenem, preferably also comprising an enzyme inhibitor such as a dehydropeptidase inhibitor or a beta-lactamase inhibitor, more preferably Cilastatin.

In a further embodiment, the combination of the present invention comprises an amino acidic sequence comprising or, alternatively, consisting of CD6.PD3 (GQVEVHFRGVW, SEQ ID NO.: 3), or a derivative thereof, an amino acidic sequence comprising or, alternatively, consisting of CD6.PD1 (GTVEVRLEASW, SEQ ID NO.: 1), or a derivative thereof, and at least one antibiotic, preferably Imipenem, preferably also comprising an enzyme inhibitor such as a dehydropeptidase inhibitor or a beta-lactamase inhibitor, more preferably Cilastatin.

In a further embodiment, the combination of the present invention comprises an amino acidic sequence comprising or, alternatively, consisting of CD6.PD3 (GQVEVHFRGVW, SEQ ID NO.: 3), or a derivative thereof, an amino acidic sequence comprising or, alternatively, consisting of CD6.PD2 (GRVEMLEHGEW, SEQ ID NO.: 2), or a derivative thereof, and at least one antibiotic, preferably Imipenem, preferably also comprising an enzyme inhibitor such as a dehydropeptidase inhibitor or a beta-lactamase inhibitor, more preferably Cilastatin.

In a further embodiment, the combination of the present invention comprises an amino acidic sequence comprising or, alternatively, consisting of CD6.PD3 (GQVEVHFRGVW, SEQ ID NO.: 3), or a derivative thereof, an amino acidic sequence comprising or, alternatively, consisting of CD6.PD2 (GRVEMLEHGEW, SEQ ID NO.: 2), or a derivative thereof, an amino acidic sequence comprising or, alternatively, consisting of CD6.PD1 (GTVEVRLEASW, SEQ ID NO.: 1), or a derivative thereof, and at least one antibiotic, preferably Imipenem, preferably also comprising an enzyme inhibitor such as a dehydropeptidase inhibitor or a beta-lactamase inhibitor, more preferably Cilastatin.

Composition

In a third aspect, the present invention provides a composition, preferably a pharmaceutical composition, comprising one or more of the amino acidic sequences or the peptides of the present invention, or a derivative thereof ("the composition of the present invention"). For example, the composition, preferably a pharmaceutical composition, of the present invention may comprise the combination of the present invention.

In a preferred embodiment, the composition, preferably a pharmaceutical composition, of the present invention comprises an amino acidic sequence comprising or, alternatively, consisting of CD6.PD3 (GQVEVHFRGVW, SEQ ID NO.: 3), or a derivative thereof.

In another embodiment, the composition, preferably a pharmaceutical composition, of the present invention comprises an amino acidic sequence comprising or, alternatively, consisting of CD6.PD1 (GTVEVRLEASW, SEQ ID NO.: 1), or a derivative thereof.

In further embodiment, the composition, preferably a pharmaceutical composition, of the present invention comprises an amino acidic sequence comprising or, alternatively, consisting of CD6.PD2 (GRVEMLEHGEW, SEQ ID NO.: 2), or a derivative thereof.

In a further embodiment, the composition, preferably a pharmaceutical composition, of the present invention comprises an amino acidic sequence comprising or, alternatively, consisting of CD6.PD2 (GRVEMLEHGEW, SEQ ID NO.: 2), or a derivative thereof, and an amino acidic sequence comprising or, alternatively, consisting of CD6.PD1 (GTVEVRLEASW, SEQ ID NO.: 1), or a derivative thereof.

In a further embodiment, the composition, preferably a pharmaceutical composition, of the present invention comprises an amino acidic sequence comprising or, alternatively, consisting of CD6.PD3 (GQVEVHFRGVW, SEQ ID NO.: 3), or a derivative thereof, and an amino acidic sequence comprising or, alternatively, consisting of CD6.PD1 (GTVEVRLEASW, SEQ ID NO.: 1), or a derivative thereof.

In a further embodiment, the composition, preferably a pharmaceutical composition, of the present invention comprises an amino acidic sequence comprising or, alternatively, consisting of CD6.PD3 (GQVEVHFRGVW, SEQ ID NO.: 3), or a derivative thereof, and an amino acidic sequence comprising or, alternatively, consisting of CD6.PD2 (GRVEMLEHGEW, SEQ ID NO.: 2), or a derivative thereof.

In a further embodiment, the composition, preferably a pharmaceutical composition, of the present invention comprises an amino acidic sequence comprising or, alternatively, consisting of CD6.PD3 (GQVEVHFRGVW, SEQ ID NO.: 3), or a derivative thereof, an amino acidic sequence comprising or, alternatively, consisting of CD6.PD2 (GRVEMLEHGEW, SEQ ID NO.: 2), or a derivative thereof, and an amino acidic sequence comprising or, alternatively, consisting of CD6.PD1 (GTVEVRLEASW, SEQ ID NO.: 1), or a derivative thereof.

As stated above, in a preferred embodiment, the composition of the present invention is a pharmaceutical composition. Accordingly, the present invention provides a pharmaceutical composition comprising one or more of the following isolated amino acid sequences SEQ ID No.: 3, and/or SEQ ID No.: 1, and/or SEQ ID No.: 2, or a derivative thereof.

As the skilled person knows, a pharmaceutical composition may comprise, in addition to the one or more active ingredients (e.g., the one or more amino acidic sequences or peptides of the present invention), pharmaceutically acceptable carriers, pharmaceutically acceptable salts, adjuvants and/or suitable excipients. In addition, the pharmaceutical composition of the present invention comprises the composition of the present invention together with pharmaceutically acceptable carriers, pharmaceutically acceptable salts, adjuvants and/or suitable excipients.

As used herein, the expression "pharmaceutically acceptable carrier" means a non-toxic solvent, dispersant, excipient, adjuvant, or other material that is mixed with active ingredient(s) in order to permit the formation of a pharmaceutical composition, i.e., a dosage form capable of administration to the patient. One example of such a carrier is a pharmaceutically acceptable oil typically used for parenteral administration.

The term "pharmaceutically acceptable salts" as used herein means that the salts of the compounds of the present invention can be used in medicinal preparations. Other salts may, however, be useful in the preparation of the compounds according to the invention or of their pharmaceutically acceptable salts.

The term "carrier" refers to a diluent or excipient with which the active ingredient(s) is(are) administered. Such pharmaceutical carriers can be sterile liquids, such as water and oils, including those of petroleum, animal, plant or synthetic origin, such as peanut oil, soybean oil, mineral oil, sesame oil and the like. Water or aqueous solutions of saline solution and aqueous dextrose and glycerol solutions, particularly for injectable solutions, are preferably used as carriers. Suitable pharmaceutical carriers are described in "Remington's Pharmaceutical Sciences" by E. W. Martin, 1995.

An "adjuvant" as used herein is a substance that has few or no pharmacological effects by itself, but may increase the efficacy or potency of other agents when given at (essentially) the same time and oftentimes in (essentially) the same route of administration at (essentially) the same site (e.g. injection into the same muscle) as the other agent. More particularly, when used in the context of immunizations, an adjuvant is a substance that stimulates or that may stimulate the immune system and increase the response to an immunizing agent, without having any specific antigenic effect in itself. More specifically, an immunologic adjuvant can be defined as a substance that acts to accelerate, prolong, or enhance antigen-specific immune responses when used in combination with specific antigen agent(s).

The carriers and the auxiliary substances necessary to manufacture the desired pharmaceutical dosage form of the pharmaceutical composition of the invention will depend, among other factors, on the pharmaceutical dosage form chosen. Said pharmaceutical dosage forms of the pharmaceutical composition of the invention will be manufactured according to conventional methods known by the person skilled in the art.

Examples of pharmaceutical compositions include any solid (tablets, pills, capsules, granulates, etc.) or liquid (solutions, suspensions or emulsions) compositions for oral, topical, or parenteral administration as intraperitoneal, intravenous, intramuscular or subcutaneous administration. Furthermore, the pharmaceutical composition can contain, as appropriate, stabilizers, suspensions, preservatives, surfactants and the like.

The skilled in the art will adapt the composition depending on the particular mode of administration. The composition of the present invention may further comprise other therapeutic agents against the infectious diseases or the inflammatory conditions related thereto, or combinations thereof.

Kit-of-Parts

In a third aspect, the present invention provides a kit-of-parts comprising, or alternatively, consisting of one or more of the amino acid sequences or peptides of the present invention (or derivatives thereof) and at least one antibiotic. Preferably, the antibiotic is a beta-lactam antibiotic, more preferably Imipenem ("the kit-of-parts of the present invention"). In a preferred embodiment, the combination further comprises an enzyme inhibitor such as a dehydropeptidase inhibitor or a beta-lactamase inhibitor, more preferably Cilastatin. Even more preferably, the kit-of-parts comprises imipenem and Cilastatin.

Other antibiotics can be used in the kit-of-parts of the present invention. Examples of other beta-lactam antibiotics are carbapenems such as meropenem, ertapenem, doripenem, penicillins such amoxicillin, ampicillin, propicillin, oxacillin, dicloxacillin, flucloxacillin, mezlocillin, piperacillin, etc. Examples of other classes of antibiotics include aminoglycosides such as streptomycin, gentamycin, tobramycin, netilmicin, amikacin, etc.; tetracyclines such as tetracycline, doxycycline, minocycline, chlortetracycline, oxytetracycline, demeclocycline, lymecycline, meclocycline, methacycline, minocycline, rolitetracycline, etc., and quinolones such as flumequine (Flubactin), oxolinic acid (Uroxin), rosoxacin (Eradacil), ciprofloxacin (Zoxan, Ciprobay, Cipro, Ciproxin), fleroxacin (Megalone, Roquinol), lomefloxacin (Maxaquin), nadifloxacin (Acuatim, Nadoxin, Nadixa), norfloxacin (Lexinor, Noroxin, Quinabic, Janacin), ofloxacin (Floxin, Oxaldin, Tarivid), pefloxacin (Peflacine), rufloxacin (Uroflox), balofloxacin (Baloxin), grepafloxacin (Raxar), levofloxacin (Cravit, Levaquin), pazufloxacin (Pasil, Pazucross), sparfloxacin (Zagam), temafloxacin (Omniflox), clinafloxacin, gatifloxacin (Zigat, Tequin) (Zymaropth), moxifloxacin (Avelox,Vigamox), sitafloxacin (Gracevit), prulifloxacin (Quisnon) and besifloxacin (Besivance), preferably fluoroquinolones. Glycopeptide antibiotics such as vancomycin, teicoplanin or telavancin, or macrolide antibiotics such as erythromycin, spiramycin, roxithromycin, clarithromycin or azithromycin, among others, are also contemplated.

The kit-of-parts can also comprise other beta-lactamase inhibitors, such as clavulanic acid, sulbactam, tebipenem, 6-Methylidene Penem2, tazobactam, avibactam or relebactam.

Common combinations of beta-lactam antibiotics and beta-lactamase inhibitors are, for instance, ampicillin/sulbactam, amoxicillin/clavulanate or piperacillin/tazobactam.

The kit-of-parts may also be referred to in the present description as "combination product" and/or "pharmaceutical product", and is defined in the context of the present application as a product or multicomponent system comprising two or more components, which are not necessarily present as a union, e.g., in composition, but which are available for simultaneous, separate or sequential application or administration. Accordingly, the components of the kit-of-parts may be physically separated, in different containers, as it will be described in detail below.

The multicomponent system can be used to store the one or more amino acidic sequences or peptides of the present invention in one container and the antibiotic (preferably Imipenem), preferably also comprising an enzyme inhibitor such as a dehydropeptidase inhibitor or a beta-lactamase inhibitor (preferably Cilastatin) in the other container. At the appropriate time, the components can be mixed. Alternatively, the components may be used separately or sequentially, namely without being mixed before administration to a subject in need thereof.

In particular, such a kit of parts may comprise or, alternatively, consists of, (a) a first container comprising the one or more amino acidic sequences or peptides of the present invention and (b) a second container comprising an antibiotic, preferably Imipenem, as described above, preferably also comprising an enzyme inhibitor such as a dehydropeptidase inhibitor or a beta-lactamase inhibitor, preferably Cilastatin, as described above.

The kit-of-parts of the present invention may comprise, or, alternatively, consist of the one or more amino acidic sequences or peptides of the present invention and an antibiotic, preferably Imipenem, as described above, preferably also comprising an enzyme inhibitor such as a dehydropeptidase inhibitor or a beta-lactamase inhibitor, preferably Cilastatin, as described above, as separate entities (e.g., comprised in separate containers), which may be administered to the subject (a mammal, preferably a human) simultaneously, sequentially or separately. In a preferred embodiment, the kit-of-parts of the present invention comprises or, alternatively, consists of the one or more amino acidic sequences or peptides of the present invention and an antibiotic, preferably Imipenem, as described above, preferably also comprising an enzyme inhibitor such as a dehydropeptidase inhibitor or a beta-lactamase inhibitor, preferably Cilastatin, as described above as separate entities (e.g., comprised in separate containers), which may be administered to the subject (a mammal, preferably a human, or a non-mammal) simultaneously, sequentially or separately. In another embodiment, the containers are combined into a single article of manufacture having a barrier between the containers. This barrier can either be removed or destroyed allowing mixing of the components at the appropriate time.

Accordingly, the present invention provides a kit-of-parts of the present invention for its simultaneous, separate or sequential use as a medicament, in particular in a therapeutic and/or preventive method of treatment, in a mammal including a human, and/or in a non-mammal, of an infectious disease, or of an inflammatory condition related to an infectious disease, or of an inflammatory disease related to the presence of a product derived from an infectious agent, as defined below.

For instance, the mammal may be a rodent (such as a mouse or a rat), a primate (such as an ape, monkey or lemur), a dog, a cat, a rabbit, and an ungulate such as cattle, horses or pigs. In a preferred embodiment, the mammal is a human.

For instance, the non-mammal may be a chicken, a duck, a goose, an ostrich, a pigeon, a turkey, etc.).

The kit-of-parts of the present invention may comprise, or, alternatively, consist of:

a) a pharmaceutical composition comprising the one or more amino acidic sequences or peptides of the present invention, or a derivative thereof, or a, and pharmaceutically acceptable carriers, pharmaceutically acceptable salts, adjuvants and/or suitable excipients; and b) a pharmaceutical composition comprising an antibiotic, preferably Imipenem, as described above, preferably also comprising an enzyme inhibitor such as a dehydropeptidase inhibitor or a beta-lactamase inhibitor, preferably Cilastatin, as described above and pharmaceutically acceptable carriers, pharmaceutically acceptable salts, adjuvants and/or suitable excipients. More preferably, the pharmaceutical composition comprises Imipenem, even more preferably, together with Cilastatin.

Both pharmaceutical compositions (a) and (b) are preferably comprised in the kit-of-parts of the present invention as separate entities (e.g., as separate liquid or solid compositions, in separate containers, as described above), which may be administered to the subject (a mammal, preferably a human, or a non-mammal) simultaneously, sequentially or separately.

As it has been mentioned above, and will be further described below, the combination, composition, pharmaceutical composition and/or the kit-of-parts of the present invention may further preferably comprise an enzyme inhibitor such as a dehydropeptidase inhibitor or a beta-lactamase inhibitor, preferably Cilastatin. An enzyme inhibitor such as a dehydropeptidase inhibitor or a beta-lactamase inhibitor, preferably Cilastatin may be comprised in the kit-of-parts of the present invention as a (third) separate entity, in a third separate container, preferably in the form of a pharmaceutical composition comprising an enzyme inhibitor such as a dehydropeptidase inhibitor or a beta-lactamase inhibitor, preferably Cilastatin and pharmaceutically acceptable carriers, pharmaceutically acceptable salts, adjuvants and/or suitable excipients. Preferably, an enzyme inhibitor such as a dehydropeptidase inhibitor or a beta-lactamase inhibitor, preferably Cilastatin is comprised in the same entity (same container) as an antibiotic, preferably Imipenem, as described above (e.g., a composition or pharmaceutical composition comprising Imipenem and Cilastatin).

For instance, the one or more amino acidic sequences or peptides of the present invention, or a derivative thereof (or the pharmaceutical composition comprising the one or more amino acidic sequences or peptides of the present invention, or a derivative thereof, and pharmaceutically acceptable carriers, pharmaceutically acceptable salts, adjuvants and/or suitable excipients) and an antibiotic, preferably Imipenem, as described above, preferably together with an enzyme inhibitor such as a dehydropeptidase inhibitor or a beta-lactamase inhibitor, preferably Cilastatin, as described above (or the pharmaceutical composition comprising an antibiotic, preferably Imipenem, as described above, preferably together with an enzyme inhibitor such as a dehydropeptidase inhibitor or a beta-lactamase inhibitor, preferably Cilastatin, as described above, and pharmaceutically acceptable carriers, pharmaceutically acceptable salts, adjuvants and/or suitable excipients) comprised in the kit-of-parts of the present invention, preferably as separate entities, may be administered simultaneously (at the same time) to the subject (a mammal, preferably a human).

Alternatively, the one or more amino acidic sequences or peptides of the present invention, or a derivative thereof (or the pharmaceutical composition comprising the one or more amino acidic sequences or peptides of the present invention, or a derivative thereof, and pharmaceutically acceptable carriers, pharmaceutically acceptable salts, adjuvants and/or suitable excipients) and an antibiotic, preferably Imipenem, as described above, preferably together with an enzyme inhibitor such as a dehydropeptidase inhibitor or a beta-lactamase inhibitor, preferably Cilastatin, as described above (or the pharmaceutical composition comprising an antibiotic, preferably Imipenem, as described above, preferably together with an enzyme inhibitor such as a dehydropeptidase inhibitor or a beta-lactamase inhibitor, preferably Cilastatin, as described above, and pharmaceutically acceptable carriers, pharmaceutically acceptable salts, adjuvants and/or suitable excipients) comprised in the kit-of-parts of the present invention, preferably as separate entities, may be administered sequentially to the subject (a mammal, preferably a human); for instance, the one or more amino acidic sequences or peptides of the present invention, or a derivative thereof (or the pharmaceutical composition comprising the one or more amino acidic sequences or peptides of the present invention, or a derivative thereof, and pharmaceutically acceptable carriers, pharmaceutically acceptable salts, adjuvants and/or suitable excipients) may be administered in first place and, afterwards, an antibiotic, preferably Imipenem, as described above, preferably together with an enzyme inhibitor such as a dehydropeptidase inhibitor or a beta-lactamase inhibitor, preferably Cilastatin, as described above (or the pharmaceutical composition comprising an antibiotic, preferably Imipenem, as described above, preferably together with an enzyme inhibitor such as a dehydropeptidase inhibitor or a beta-lactamase inhibitor, preferably Cilastatin, as described above, and pharmaceutically acceptable carriers, pharmaceutically acceptable salts, adjuvants and/or suitable excipients) is administered to the subject (a mammal, preferably a human).

Preferably, an antibiotic, preferably Imipenem, as described above, preferably together with an enzyme inhibitor such as a dehydropeptidase inhibitor or a beta-lactamase inhibitor, preferably Cilastatin, as described above (or the pharmaceutical composition comprising an antibiotic, preferably Imipenem, as described above, preferably together with an enzyme inhibitor such as a dehydropeptidase inhibitor or a beta-lactamase inhibitor, preferably Cilastatin, as described above, and pharmaceutically acceptable carriers, pharmaceutically acceptable salts, adjuvants and/or suitable excipients) is first administered to the subject (a mammal, preferably a human) and, afterwards, the one or more amino acidic sequences or peptides of the present invention, or a derivative thereof (or the pharmaceutical composition comprising the one or more amino acidic sequences or peptides of the present invention, or a derivative thereof, and pharmaceutically acceptable carriers, pharmaceutically acceptable salts, adjuvants and/or suitable excipients) is administered to the subject.

Alternatively, the one or more amino acidic sequences or peptides of the present invention, or a derivative thereof (or the pharmaceutical composition comprising the one or more amino acidic sequences or peptides of the present invention, or a derivative thereof, and pharmaceutically acceptable carriers, pharmaceutically acceptable salts, adjuvants and/or suitable excipients) and an antibiotic, preferably Imipenem, as described above, preferably together with an enzyme inhibitor such as a dehydropeptidase inhibitor or a beta-lactamase inhibitor, preferably Cilastatin, as described above (or the pharmaceutical composition comprising an antibiotic, preferably Imipenem, as described above, preferably together with an enzyme inhibitor such as a dehydropeptidase inhibitor or a beta-lactamase inhibitor, preferably Cilastatin, as described above, and pharmaceutically acceptable carriers, pharmaceutically acceptable salts, adjuvants and/or suitable excipients) comprised in the kit-of-parts of the present invention, preferably as separate entities, may be administered separately to the subject (a mammal, preferably a human). For example, the subject (a mammal, preferably a human) is already taking an antibiotic, preferably Imipenem, as described above, preferably together with an enzyme inhibitor such as a dehydropeptidase inhibitor or a beta-lactamase inhibitor, preferably Cilastatin, as described above, (or the pharmaceutical composition comprising an antibiotic, preferably Imipenem, as described above, preferably together with an enzyme inhibitor such as a dehydropeptidase inhibitor or a beta-lactamase inhibitor, preferably Cilastatin, as described above, and pharmaceutically acceptable carriers, pharmaceutically acceptable salts, adjuvants and/or suitable excipients) and the one or more amino acidic sequences or peptides of the present invention, or a derivative thereof (or the pharmaceutical composition comprising the one or more amino acidic sequences or peptides of the present invention, or a derivative thereof, and pharmaceutically acceptable carriers, pharmaceutically acceptable salts, adjuvants and/or suitable excipients) is administered, preferably in a single dose.

Accordingly, the components of the kit-of-parts of the present invention may be simultaneously, sequentially or separately administered to a subject (a mammal including a human), in a therapeutic and/or preventive method of treatment, preferably, of an infectious disease, or of an inflammatory condition related to an infectious disease, or of an inflammatory disease related to the presence of a product derived from an infectious agent, as it will be described below.

Imipenem

Imipenem is a β-lactam antibiotic belonging to the carbapenem class of antibiotics. Carbapenems are highly resistant to the β-lactamase enzymes produced by many multiple drug-resistant G− bacteria. Imipenem acts as an antimicrobial through inhibiting cell wall synthesis of various G+ and G− bacteria, thus reducing the amount of PAMPs released during bacteriolysis. It remains very stable in the presence of β-lactamase (both penicillinase and cephalosporinase) produced by some bacteria, and is a strong inhibitor of β-lactamases from some G− bacteria that are resistant to most β-lactam antibiotics. The systematic IUPAC name for Imipenem is (5R,6S)-6-[(1R)-1-hydroxyethyl]-3-({2-[(iminomethyl)amino]ethyl}thio)-7-oxo-1-azabicyclo[3.2.0]hept-2-ene-2-carboxylic acid, its CAS registry number is 74431-23-5 and its chemical formula is as described below in Formula 1:

Formula 1

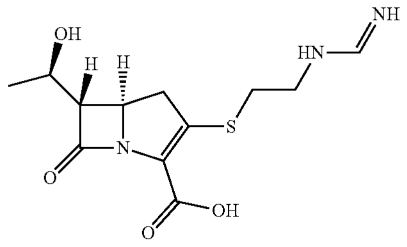

Imipenem

As it will be described in detail below, Imipenem is generally administered together with Cilastatin.

Cilastatin

Cilastatin is a compound that inhibits human dehydropeptidase, the enzyme responsible for the in vivo degradation of the antibiotic Imipenem. Accordingly, Cilastatin may be administered together with Imipenem in order to protect its degradation by dehydropeptidase, thereby prolonging the circulation time and thus its antibacterial effect in the body. Cilastatin itself does not have antibiotic activity. As the skilled person is aware of, Imipenem alone is an effective antibiotic and can be administered without Cilastatin. However, preferably, Imipenem is administered with Cilastatin, preferably in a ratio Imipenem:Cilastatin of 1:1.

Effects of the Amino Acid Sequences, Peptides (or Derivatives Thereof), Combination, Composition, Pharmaceutical Composition and Kit-of-Parts of the Invention According to the teaching of the present invention, the one or more amino acid sequences, peptides, or derivatives thereof, combination, composition, pharmaceutical composition and/or the components of the kit-of-parts of the present invention can be administrated to a mammalian, preferably a human. Alternatively, the one or more amino acid sequences, peptides, or derivatives thereof, combination, composition, pharmaceutical composition and/or the components of the kit-of-parts of the present invention can be administrated to a non-mammal, preferably a chicken, a duck, a goose, an ostrich, a pigeon and/or a turkey. The purpose of the administration of the one or more amino acid sequences, peptides (or derivatives thereof), combination, composition, pharmaceutical composition and/or the components of the kit-of-parts of the present invention may be preventive (to avoid the development of these diseases) and/or therapeutic (to treat these diseases once they have been developed/installed).

It is to be understood that the one or more amino acid sequences, peptides (or derivatives thereof), combination, composition, pharmaceutical composition and/or the components of the kit-of-parts of the present invention are administered in a pharmaceutically acceptable form. Those skilled in the art may ascertain the proper dose using standard procedures. It is understood that the dose should be an effective amount of the one or more amino acid sequences or peptides (or derivatives thereof), with or without an antibiotic, preferably Imipenem, as described above (and with or without an enzyme inhibitor such as a dehydropeptidase inhibitor or a beta-lactamase inhibitor, preferably Cilastatin, as described above) in the sense that a reduced inflammatory response is seen in the treated subject.

The specific co-administration (simultaneously, sequentially or separately) of the one or more amino acid sequences or peptides of the present invention (or derivatives thereof), preferably CD6.PD3, or a derivative thereof, and an antibiotic, preferably Imipenem (preferably together with a an enzyme inhibitor such as dehydropeptidase inhibitor or a beta-lactamase inhibitor, preferably Cilastatin, as described above) provide for clear improved additive therapeutic effects, particularly in the treatment and/or prevention of an infectious disease, or of an inflammatory condition related to an infectious disease, or of an inflammatory disease related to the presence of a product derived from an infectious agent in a mammal including a human, and/or in a non-mammal, including a chicken, a duck, a goose, an ostrich, a pigeon and/or a turkey.

Methods of Treatment

In a further aspect, the one or more amino acid sequences, peptides (or derivatives thereof), combination, composition, pharmaceutical composition and/or the kit-of-parts of the present invention, in any of their variants, can be used as a medicament, preferably in a therapeutic and/or preventive method of treatment, in a mammal including a human, and/or in a non-mammal, including a chicken, a duck, a goose, an ostrich, a pigeon and/or a turkey of an infectious disease, or of an inflammatory condition related to an infectious disease, or of an inflammatory disease related to the presence of a product derived from an infectious agent. The present invention thus provides a therapeutic and/or preventive method of treatment of an infectious disease, or of an inflammatory condition related to an infectious disease, or of an inflammatory disease related to the presence of a product derived from an infectious agent comprising the administration of the one or more amino acid sequences, peptides (or derivatives thereof), combination, composition, pharmaceutical composition and/or the kit-of-parts of the present invention to a mammal and/or to a non-mammal. For instance, the mammal may be a rodent (such as a mice or a rat), a primate (such as an ape, monkey or lemur), a dog, a cat, a rabbit, and an ungulate such as cattle, horses or pigs. In a preferred embodiment, the mammal is a human. For instance, the non-mammal may be a chicken, a duck, a goose, an ostrich, a pigeon, a turkey, etc.).

Preferably, the present invention provides a therapeutic and/or preventive method of treatment of an infectious disease, or of an inflammatory condition related to an infectious disease, or of an inflammatory disease related to the presence of a product derived from an infectious agent comprising the administration to a mammal, preferably to a human, and/or to a non-mammal, as described above, of an amino acid sequence comprising or, alternatively, consisting of GQVEVHFRGVW (CD6.PD3, SEQ ID NO.: 3), or a derivative thereof, or of a combination, composition, pharmaceutical composition and/or kit of parts as defined above which comprise an amino acid sequence comprising or, alternatively, consisting of GQVEVHFRGVW (CD6.PD3, SEQ ID NO.: 3), or a derivative thereof.

For instance, the present invention provides a therapeutic and/or preventive method of treatment of an infectious disease, or of an inflammatory condition related to an infectious disease, or of an inflammatory disease related to the presence of a product derived from an infectious agent comprising the administration to a mammal, preferably to a human, and/or to a non-mammal, as described above, of an amino acid sequence comprising or, alternatively, consisting of GTVEVRLEASW (CD6.PD1, SEQ ID NO.: 1), or a derivative thereof, or of a combination, composition, pharmaceutical composition and/or kit of parts as defined above which comprise an amino acid sequence comprising or, alternatively, consisting of GTVEVRLEASW (CD6.PD1, SEQ ID NO.: 1), or a derivative thereof.

For instance, the present invention provides a therapeutic and/or preventive method of treatment of an infectious disease, or of an inflammatory condition related to an infectious disease, or of an inflammatory disease related to the presence of a product derived from an infectious agent comprising the administration to a mammal, preferably to a human, and/or to a non-mammal, as described above, of an amino acid sequence comprising or, alternatively, consisting of GRVEMLEHGEW (CD6.PD2, SEQ ID NO.: 2), or a derivative thereof, or of a combination, composition, pharmaceutical composition and/or kit of parts as defined above which comprise an amino acid sequence comprising or, alternatively, consisting of GRVEMLEHGEW (CD6.PD2, SEQ ID NO.: 2), or a derivative thereof.

For instance, the present invention provides the kit-of-parts of the present invention for simultaneous, sequential or separate use as a medicament. In particular, the present invention provides the kit-of-parts of the present invention for simultaneous, sequential or separate use in a therapeutic and/or preventive method of treatment, in a mammal including a human, and/or to a non-mammal, as described above, of an infectious disease, or of an inflammatory condition related to an infectious disease, or of an inflammatory disease related to the presence of a product derived from an infectious agent.

In a particular embodiment of the invention, the infectious disease is a microbial infection. In more particular embodiments, the microbial infection is selected from the group consisting of a bacterial infection (either G+ or G− bacteria, saprophytic or pathogenic, aerobic or anaerobic), a fungal infection, a viral infection, a parasitic infection, and combinations thereof (polymicrobial infection).

In another particular embodiment, the infectious disease is a septicemia. As used herein, the term "septicemia" refers to the presence of any microbe in blood stream. Particularly, the septicemia is selected from the group consisting of a bacteremia, a fungemia, a viremia, a parasitemia, and combinations thereof.

The presence of viable microbes is found in most cases of inflammatory conditions related to an infectious disease, whereas 20% to 30% of patients do not have microbes identified from any source but products derived from them. Thus, in another embodiment, the inflammatory condition is related to a product derived from an infectious agent. Particularly, the infectious agent is selected from the group consisting of a bacterium (either G+ or G− bacteria, saprophytic or pathogenic, aerobic or anaerobic), a fungus, a virus, a parasite, and/or combinations thereof.

Sepsis is defined as the presence or presumed presence of an infection accompanied by evidence of a systemic response called the systemic inflammatory response syndrome (SIRS). For sepsis definition, reference is made to the article "Severe sepsis and septic shock: review of the literature and emergency department management guidelines", H. B. Nguyen et al., Ann. Emergency Med. 2006, vol.

48, pp. 28-54. Sepsis is usually caused by bacterial infections (either G+ or G− bacteria) but can also be caused by other pathogens. Most often however, sepsis is caused by G+ and G− bacterial infections. However, the injury and symptoms attributable to sepsis are not only caused by the whole alive bacteria but are also caused by a component of the bacteria cell wall known as endotoxins. Endotoxins (e.g., LPS, LTA, PGN) are glycolipids that are ubiquitous in the outer membrane of G+ and G− bacteria. Endotoxins are released when the immune system destroys the invading bacteria. The released endotoxins bind to immune cells (monocytes, macrophages, granulocytes, lymphocytes, and endothelial and epithelial cells) and trigger the production of various soluble mediators of inflammation such as cytokines (e.g., TNF-α, IL-1β, and IL-6) and chemokines (e.g., IL-8), which are a major cause of severe forms of sepsis.

In a particular embodiment of the invention, the inflammatory condition is SIRS (systemic inflammatory response syndrome). In another particular embodiment, the inflammatory condition is sepsis. SIRS is defined as the presence of two or more of the following: (1) temperature greater than 38° C. or less than 36° C.; (2) pulse rate greater than 90 beats/min; (3) respiratory rate greater than 20 breaths/min (or $PCO_2$ less than 32 torr); and (4) white blood cells count greater than 12000/mm 3 or less than 4000/mm 3, or greater than 10% immature band forms.

In a particular embodiment, the sepsis is polymicrobial sepsis. Polymicrobial sepsis is defined as a complex systemic infection involving concurrence of multiple infectious agents (e.g., bacterial and fungal; saprophytic and pathogens; aerobic and anaerobic, etc.).

In another particular embodiment, the inflammatory condition is severe sepsis. Severe sepsis is defined as the sepsis which is accompanied by one or more organ dysfunctions. Organ dysfunction can be defined as acute lung injury; coagulation abnormalities; thrombocytopenia; altered mental status; renal, liver, or cardiac failure; or hypoperfusion with lactic acidosis.

In another particular embodiment, the inflammatory condition is septic shock. Septic shock is defined as the presence of sepsis and refractory hypotension, i.e., systolic blood pressure less than mmHg, mean arterial pressure less than 65 mmHg, or a decrease of 40 mmHg in systolic blood pressure compared to baseline unresponsive to a crystalloid fluid challenge of 20 to 40 ml/kg. Thus, septic shock is effectively a form of severe sepsis. Finally, the septic shock may be endotoxin-induced septic shock.

The source of the infection can be any of a number of places throughout the body. Common sites of infection that can lead to sepsis comprise the following: inflammation of the appendix (appendicitis), diverticulitis, bowel problems, infection of the abdominal cavity (peritonitis), and gallbladder or liver infections; inflammation or infections of the brain or the spinal cord (meningitis, encephalitis); lung infections such as pneumonia; skin infections through wounds or through openings made with intravenous catheters, cellulitis (inflammation of the skin's connective tissue); urinary tract infections, especially if the patient has a urinary catheter to drain urine; dental and gynecological examinations or treatments; blunt or penetrating trauma, surgery, and endocarditis.

The administration of the one or more amino acid sequences, peptides (or derivatives thereof), combination, composition, pharmaceutical composition and/or the kit-of-parts of the present invention, in any of their variants, to a mammal, including a human, and/or to a non-mammal, as described above, may be done intraperitoneally (i.p.) and/or intravenously (i.v.).

Preferably, the one or more amino acid sequences, peptides (or derivatives thereof), composition and/or pharmaceutical composition of the present invention, in any of their variants, are administered to a mammal, including a human, and/or to a non-mammal, as described above, as follows. A single dose of the one or more amino acid sequences or peptides, preferably CD6.PD3, or a derivative thereof, (or a pharmaceutical composition comprising the one or more amino acid sequences or peptides, preferably CD6.PD3, or a derivative thereof, and pharmaceutically acceptable carriers, pharmaceutically acceptable salts, adjuvants and/or suitable excipients) is administered as early as possible, preferably i.v., optionally during antibiotic (preferably Imipenem) treatment (preferably together with an enzyme inhibitor such as a dehydropeptidase inhibitor or a beta-lactamase inhibitor, preferably Cilastatin, as described above). The optimal peptide dose in mice is 3-15 mg/kg, preferably 6-12 mg/kg. As the skilled person would understand, the optimal peptide dose for other mammals, including humans (and for non-mammals), should be established in clinical assays.

In another preferred embodiment, the components of the kit-of-parts of the present invention are administered as follows. A single dose of the one or more amino acid sequences or peptides, preferably CD6.PD3, or a derivative thereof (or a pharmaceutical composition comprising one or more amino acid sequences or peptides, preferably CD6.PD3, or a derivative thereof, and pharmaceutically acceptable carriers, pharmaceutically acceptable salts, adjuvants and/or suitable excipients) is administered as early as possible, preferably i.v., and, subsequently, an antibiotic, preferably Imipenem (or a pharmaceutical composition comprising an antibiotic, preferably Imipenem and pharmaceutically acceptable carriers, pharmaceutically acceptable salts, adjuvants and/or suitable excipients) (preferably together with an enzyme inhibitor such as a dehydropeptidase inhibitor or a beta-lactamase inhibitor, preferably Cilastatin, as described above) is administered to a subject in need thereof.

In another preferred embodiment, the components of the kit-of-parts of the present invention are administered as follows. First, an antibiotic, preferably Imipenem (or a pharmaceutical composition comprising an antibiotic, preferably Imipenem and pharmaceutically acceptable carriers, pharmaceutically acceptable salts, adjuvants and/or suitable excipients) (preferably together with an enzyme inhibitor such as a dehydropeptidase inhibitor or a beta-lactamase inhibitor, preferably Cilastatin, as described above) is administered to a subject in need thereof. Subsequently, a single dose of the one or more amino acid sequences or peptides, preferably CD6.PD3, or a derivative thereof, (or a pharmaceutical composition comprising one or more amino acid sequences or peptides, preferably CD6.PD3, or a derivative thereof, and pharmaceutically acceptable carriers, pharmaceutically acceptable salts, adjuvants and/or suitable excipients) is administered, preferably i.v.

Alternatively, not only a single dose of the one or more amino acid sequences or peptides of the present invention, or derivatives thereof, as described above, is administered to a subject in need thereof, but more than one dose may be administered, such as two, three, four, five, six, seven, eight, nine, ten or more doses may be administered to a subject in need thereof. As the skilled person may understand, one two, three, four, five, six, seven, eight, nine, ten or more doses may be administered either before, during or after the administration of an antibiotic, preferably Imipenem (preferably together with an enzyme inhibitor such as a dehydropeptidase inhibitor or a beta-lactamase inhibitor, preferably Cilastatin). In addition, the one or more amino acid sequences or peptides, or derivatives thereof may not be administered in doses, but as continuous perfusion (preferably i.v.), either before, during or after the administration of the antibiotic, preferably Imipenem (preferably together with an enzyme inhibitor such as a dehydropeptidase inhibitor or a beta-lactamase inhibitor, preferably Cilastatin).

Of course, the subject in need thereof may be under the treatment of other drugs such as other antibiotics when the one or more amino acid sequences or peptides (or derivatives thereof), combination, composition, pharmaceutical composition and/or components of the kit-of-parts of the present invention, in any of its variants, are administered.

"Therapeutically effective amount" means an amount of the compound which is effective in treating the named disorder or condition.

The terms "treatment" or "therapy" encompass both prophylactic and curative methods of treating disease, since both are directed to the maintenance or restoration of health. Irrespective of the origin of the noxa, discomfort or incapacity, its relief, by the administration of an appropriate agent, is to be construed as therapy or therapeutic use in the context of the present application.

The one or more amino acid sequences or peptides (or derivatives thereof), combination, composition, pharmaceutical composition and/or kit-of-parts of the invention may thus be used in a method of therapeutic treatment (after the clinical manifestation of the disease) and/or prophylactic treatment (before the clinical manifestation of the disease).

Conjugate

In a further embodiment, the present application discloses a conjugate comprising one or more of the amino acid sequences and/or peptides of the present invention. The conjugate is preferably a conjugate wherein one or more of the amino acid sequences and/or peptides of the invention are conjugated (preferably covalently linked) to a carrier, preferably a polymer, such as a soluble polymer or, preferably, an insoluble polymer.

A "peptide-carrier conjugate" or "conjugate" is defined as a hybrid construct combining amino acid sequences and/or peptides with a carrier. The link to the carrier can be done through the NH 2 or COOH groups of the amino acid sequence and/or peptide or by any other functional groups of the amino acid side chains. The carrier may be a soluble polymer, or an insoluble polymer in which the amino acid sequence and/or peptide is immobilised in the form of a solid or hydrogel material.

In order to conjugate (or fix, or attach, or bind, or couple, or link, preferably covalently) the one or more amino acid sequences or peptides (or derivatives thereof) to the carrier, the carrier may preferably comprise one or more functional groups to this end. Representative examples of those functional groups are the following: hydroxyl group, amino group, aldehyde group, carboxyl group, thiol group, a silanol group, an amide group, epoxy group, a halogen group, succinylimide group and an acid anhydride group.

In a preferred embodiment, the conjugate of the present invention comprises an amino acidic sequence comprising or, alternatively, consisting of CD6.PD3 (GQVEVHFRGVW, SEQ ID NO.: 3), or a derivative thereof.

In another embodiment, the conjugate of the present invention comprises an amino acidic sequence comprising or, alternatively, consisting of CD6.PD1 (GTVEVRLEASW, SEQ ID NO.: 1), or a derivative thereof.

In further embodiment, the conjugate of the present invention comprises an amino acidic sequence comprising or, alternatively, consisting of CD6.PD2 (GRVEMLEHGEW, SEQ ID NO.: 2), or a derivative thereof.

In a further embodiment, the conjugate of the present invention comprises an amino acidic sequence comprising or, alternatively, consisting of CD6.PD2 (GRVEMLEHGEW, SEQ ID NO.: 2), or a derivative thereof, and an amino acidic sequence comprising or, alternatively, consisting of CD6.PD1 (GTVEVRLEASW, SEQ ID NO.: 1), or a derivative thereof.

In a further embodiment, the conjugate of the present invention comprises an amino acidic sequence comprising or, alternatively, consisting of CD6.PD3 (GQVEVHFRGVW, SEQ ID NO.: 3), or a derivative thereof, and an amino acidic sequence comprising or, alternatively, consisting of CD6.PD1 (GTVEVRLEASW, SEQ ID NO.: 1), or a derivative thereof.

In a further embodiment, the conjugate of the present invention comprises an amino acidic sequence comprising or, alternatively, consisting of CD6.PD3 (GQVEVHFRGVW, SEQ ID NO.: 3), or a derivative thereof, and an amino acidic sequence comprising or, alternatively, consisting of CD6.PD2 (GRVEMLEHGEW, SEQ ID NO.: 2), or a derivative thereof.

In a further embodiment, the conjugate of the present invention comprises an amino acidic sequence comprising or, alternatively, consisting of CD6.PD3 (GQVEVHFRGVW, SEQ ID NO.: 3), or a derivative thereof, an amino acidic sequence comprising or, alternatively, consisting of CD6.PD2 (GRVEMLEHGEW, SEQ ID NO.: 2), or a derivative thereof, and an amino acidic sequence comprising or, alternatively, consisting of CD6.PD1 (GTVEVRLEASW, SEQ ID NO.: 1), or a derivative thereof.

The conjugate of the present invention may further comprise one or more amino acid sequences comprising the peptides CD6.PD1 (SEQ ID NO.: 1), CD6.PD2 (SEQ ID NO.: 2) and/or CD6.PD3 (SEQ ID NO.: 3). The amino acid sequence can be linear or cyclic. Preferably, the amino acid sequence is comprised within the ectodomain of human CD6. In a preferred embodiment, the amino acidic sequence is comprised within SEQ ID NO.: 4. In particular embodiment, the linear or cyclic amino acidic sequence comprises between 12 and 17 adjacent amino acids comprising the peptides CD6.PD1 (SEQ ID NO.: 1), CD6.PD2 (SEQ ID NO.: 2) or CD6.PD3 (SEQ ID NO.: 3) and is preferably comprised within SEQ ID NO.: 4. Examples of preferred amino acidic sequences which may be comprised in the device of the present invention include, but are not limited to:

```
                         (SEQ ID NO.: 13)
CSGTVEVRLEASWEPAC,

                         (SEQ ID NO.: 14)
SGTVEVRLEASWEPA,

                         (SEQ ID NO.: 15)
SGTVEVRLEASWEP,

                         (SEQ ID NO.: 16)
SGTVEVRLEASWE,
```

-continued (SEQ ID NO.: 17)
SGTVEVRLEASW, (SEQ ID NO.: 18)
GTVEVRLEASWEPA, (SEQ ID NO.: 19)
GTVEVRLEASWEP, (SEQ ID NO.: 20)
GTVEVRLEASWE, (SEQ ID NO.: 21)
CAGRVEMLEHGEWGSVC, (SEQ ID NO.: 22)
AGRVEMLEHGEWGSV, (SEQ ID NO.: 23)
AGRVEMLEHGEWGS, (SEQ ID NO.: 24)
AGRVEMLEHGEWG, (SEQ ID NO.: 25)
AGRVEMLEHGEW, (SEQ ID NO.: 26)
GRVEMLEHGEWGSV, (SEQ ID NO.: 27)
GRVEMLEHGEWGS, (SEQ ID NO.: 28)
GRVEMLEHGEWG, (SEQ ID NO.: 29)
CEGQVEVHFRGVWNTVC, (SEQ ID NO.: 30)
EGQVEVHFRGVWNTV, (SEQ ID NO.: 31)
EGQVEVHFRGVWNT, (SEQ ID NO.: 32)
EGQVEVHFRGVWN, (SEQ ID NO.: 33)
EGQVEVHFRGVW, (SEQ ID NO.: 34)
GQVEVHFRGVWNTV, (SEQ ID NO.: 35)
GQVEVHFRGVWNT, (SEQ ID NO.: 36)
GQVEVHFRGVWN.

The one or more amino acid sequences and/or peptides of the present invention comprised in the conjugate may be conjugated (preferably covalently linked) to a carrier. The carrier may be an insoluble carrier. The insoluble carrier may be a solid support which may comprise insoluble inorganic carrier such as glass beads or silica gel; a synthetic polymer such as crosslinked-polyvinyl alcohol, crosslinked-polyacrylate, crosslinked-polymethacrylate, crosslinked-polyacrylamide, crosslinked-polycarbonate, crosslinked polysulfone, crosslinked polyether sulfone or crosslinked-polystyrene, or an organic carrier comprising polysaccharide such as crystalline cellulose, crosslinked-cellulose, crosslinked-agarose or crosslinked-dextran, or a composite carrier obtained from a combination of the above-mentioned compounds, such as organic-organic carrier and organic-inorganic carrier. The solid support may also be a metallic support, such as magnetic beads.

Preferably, the carrier may be a porous matrix which has a particle size between 50 and 300 μm. Preferably, the solid support is Eupergit®, which are macroporous beads with a diameter of 100-250 μm, made by copolymerization of N,N'-methylene-bis-(methacrylamide), glycidyl methacrylate, allyl glycidyl ether and methacrylamide.

In a preferred embodiment, a conjugate of peptide-coated Eupergit® beads are obtained by treatment of the polymeric beads with a solution of the peptides of the invention in a pH buffer. Preferably, the polymeric beads are incubated with the peptides of the invention at room temperature in sodium phosphate buffer.

The one or more amino acid sequences and/or peptides of the present invention comprised in the conjugate may be conjugated (preferably covalently linked) to a soluble carrier, such as albumin, or to a soluble polymer, such as, for example, PEG, dextran, polysialic acids, hyaluronic acid or hydroxyethyl-starch.

The conjugate of the invention can be used as a medicament, preferably in a therapeutic and/or preventive method of treatment, in a mammal including a human, or in a non-mammal, of an infectious disease, or of an inflammatory condition related to an infectious disease, or of an inflammatory disease related to the presence of a product derived from an infectious agent.

Device

A further aspect of the present invention relates to a device, preferably a medical device, which can be referred to also as "adsorbent", comprising one or more of the amino acid sequences or peptides of the present invention ("device of the present invention").

Accordingly, the device of the present invention comprises one or more of an amino acid sequence comprising or, alternatively, consisting of the following sequences, or a derivative thereof:

(SEQ ID NO.: 1)
CD6.PD1: GTVEVRLEASW;

(SEQ ID NO.: 2)
CD6.PD2: GRVEMLEHGEW;
and (SEQ ID NO.: 3)
CD6.PD3: GQVEVHFRGVW.

In addition, the device of the present invention may comprise one or more amino acid sequences comprising the peptides CD6.PD1 (SEQ ID NO.: 1), CD6.PD2 (SEQ ID NO.: 2) and/or CD6.PD3 (SEQ ID NO.: 3). The amino acid sequence can be linear or cyclic. Preferably, the amino acid sequence is comprised within the ectodomain of human CD6. In a preferred embodiment, the amino acidic sequence is comprised within SEQ ID NO.: 4. In particular embodiment, the linear or cyclic amino acidic sequence comprises between 12 and 17 adjacent amino acids comprising the peptides CD6.PD1 (SEQ ID NO.: 1), CD6.PD2 (SEQ ID NO.: 2) or CD6.PD3 (SEQ ID NO.: 3) and is preferably comprised within SEQ ID NO.: 4. Examples of preferred amino acidic sequences which may be comprised in the device of the present invention include, but are not limited to:

```
                          (SEQ ID NO.: 13)
CSGTVEVRLEASWEPAC,
                          (SEQ ID NO.: 14)
SGTVEVRLEASWEPA,
                          (SEQ ID NO.: 15)
SGTVEVRLEASWEP,
                          (SEQ ID NO.: 16)
SGTVEVRLEASWE,
                          (SEQ ID NO.: 17)
SGTVEVRLEASW,
                          (SEQ ID NO.: 18)
GTVEVRLEASWEPA,
                          (SEQ ID NO.: 19)
GTVEVRLEASWEP,
                          (SEQ ID NO.: 20)
GTVEVRLEASWE,
                          (SEQ ID NO.: 21)
CAGRVEMLEHGEWGSVC,
                          (SEQ ID NO.: 22)
AGRVEMLEHGEWGSV,
                          (SEQ ID NO.: 23)
AGRVEMLEHGEWGS,
                          (SEQ ID NO.: 24)
AGRVEMLEHGEWG,
                          (SEQ ID NO.: 25)
AGRVEMLEHGEW,
                          (SEQ ID NO.: 26)
GRVEMLEHGEWGSV,
                          (SEQ ID NO.: 27)
GRVEMLEHGEWGS,
                          (SEQ ID NO.: 28)
GRVEMLEHGEWG,
                          (SEQ ID NO.: 29)
CEGQVEVHFRGVWNTVC,
                          (SEQ ID NO.: 30)
EGQVEVHFRGVWNTV,
                          (SEQ ID NO.: 31)
EGQVEVHFRGVWNT,
                          (SEQ ID NO.: 32)
EGQVEVHFRGVWN,
                          (SEQ ID NO.: 33)
EGQVEVHFRGVW,
                          (SEQ ID NO.: 34)
GQVEVHFRGVWNTV,
                          (SEQ ID NO.: 35)
GQVEVHFRGVWNT,
                          (SEQ ID NO.: 36)
GQVEVHFRGVWN.
```

Preferably, the device of the present invention comprises the amino acid sequence comprising or, alternatively, consisting of GTVEVRLEASW (CD6.PD1, SEQ ID NO.: 1), or a derivative thereof.

For instance, the device of the present invention comprises the amino acid sequence comprising or, alternatively, consisting of GRVEMLEHGEW (CD6.PD2, SEQ ID NO.: 2), or a derivative thereof.

For instance, the device of the present invention comprises the amino acid sequence comprising or, alternatively, consisting of GQVEVHFRGVW (CD6.PD3, SEQ ID NO.: 3), or a derivative thereof.

In a preferred embodiment, the device of the present invention comprises the amino acid sequence comprising or, alternatively, consisting of GTVEVRLEASW (CD6.PD1, SEQ ID NO.: 1), or a derivative thereof, and the amino acid sequence comprising or, alternatively, consisting of GRVEMLEHGEW (CD6.PD2, SEQ ID NO.: 2), or a derivative thereof.

In a further embodiment, the device of the present invention comprises the amino acid sequence comprising or, alternatively, consisting of GTVEVRLEASW (CD6.PD1, SEQ ID NO.: 1), or a derivative thereof, and the amino acid sequence comprising or, alternatively, consisting of GQVEVHFRGVW (CD6.PD3, SEQ ID NO.: 3), or a derivative thereof.

In a further embodiment, the device of the present invention comprises the amino acid sequence comprising or, alternatively, consisting of GRVEMLEHGEW (CD6.PD2 SEQ ID NO.: 2), or a derivative thereof, and the amino acid sequence comprising or, alternatively, consisting of GQVEVHFRGVW (CD6.PD3, SEQ ID NO.: 3), or a derivative thereof.

In a further preferred embodiment, the device of the present invention comprises the amino acid sequence comprising or, alternatively, consisting of GRVEMLEHGEW (CD6.PD2 SEQ ID NO.: 2), or a derivative thereof, the amino acid sequence comprising or, alternatively, consisting of GTVEVRLEASW (CD6.PD1, SEQ ID NO.: 1), or a derivative thereof, and the amino acid sequence comprising or, alternatively, consisting of GQVEVHFRGVW (CD6.PD3, SEQ ID NO.: 3), or a derivative thereof.

The device of the present invention can comprise a conjugate comprising one or more of the amino acid sequences and/or peptides of the present invention. The conjugate is preferably a conjugate wherein one or more of the amino acid sequences and/or peptides of the invention are conjugated (preferably covalently linked) to a carrier, preferably a polymer, preferably an insoluble polymer.

The device is suitable for selectively binding and separating at least one component from an aqueous solution, preferably a body fluid such as blood, plasma serum or other suitable blood fractions. The aqueous solution potentially comprises at least one component which selectively binds to and is separated by the device of the invention. For instance, the at least one component potentially comprised in the aqueous solution (which is preferably a body fluid such as blood, plasma serum or other suitable blood fractions) is one or more chemical components of surface structures of Gram- and/or Gram+ bacteria, such as an endotoxin, such as LPS, LTA and/or PGN.

Important chemical components of surface structures of bacteria are the following (from Medical Microbiology, 4th edition, Baron S, editor; Galveston (TX): University of Texas Medical Branch at Galveston; 1996):

- Cell Wall Peptidoglycans (PGN): Both G+ and G− bacteria possess cell wall peptidoglycans, which confer the characteristic cell shape and provide the cell with mechanical protection. Peptidoglycans are unique to prokaryotic organisms and consist of a glycan backbone of muramic acid and glucosamine (both N-acetylated), and peptide chains highly cross-linked with bridges in G+ bacteria (e.g., *Staphylococcus aureus*) or partially cross-linked in G− bacteria (e.g., *Escherichia*

*coli*). The cross-linking transpeptidase enzymes are some of the targets for β-lactam antibiotics.

Teichoic Acids (TA): Teichoic acids are polyol phosphate polymers bearing a strong negative charge. They are covalently linked to the peptidoglycan in some G+ bacteria. They are strongly antigenic, but are generally absent in G− bacteria.

Lipoteichoic Acids (LTA): Lipoteichoic acids as membrane teichoic acids are polymers of amphiphatic glycophosphates with the lipophilic glycolipid and anchored in the cytoplasmic membrane. They are antigenic, cytotoxic and adhesins (e.g., *Streptococcus pyogenes*).

Lipopolysaccharides (LPS): One of the major components of the outer membrane of G− bacteria is lipopolysaccharide (endotoxin), a complex molecule consisting of a lipid A anchor, a polysaccharide core, and chains of carbohydrates. Sugars in the polysaccharide chains confer serologic specificity.

Wall-Less Forms: Two groups of bacteria devoid of cell wall peptidoglycans are the *Mycoplasma* species, which possess a surface membrane structure, and the L-forms that arise from either G+ or G− bacterial cells that have lost their ability to produce the peptidoglycan structures.

Preferably, the medical device of the present invention is a hemadsorption medical device, such as a medical device for extracorporeal removal of one or more chemical components of surface structures of G− and/or G+ bacteria, such as an endotoxin (e.g., LPS, LTA, and/or PGN) during hemoperfusion.

The one or more amino acid sequences or peptides, or derivatives thereof, of the present invention which are comprised in the device of the present invention, as described below, may be fixed on a solid support. The solid support may be a water insoluble inorganic carrier such as glass beads or silica gel; a synthetic polymer such as crosslinked-polyvinyl alcohol, crosslinked-polyacrylate, crosslinked-polymethacrylate, crosslinked-polyacrylamide, crosslinked-polycarbonate, crosslinked-polycarbonate, crosslinked polysulfone, crosslinked polyether sulfone or crosslinked-polystyrene, or an organic carrier comprising polysaccharide such as crystalline cellulose, crosslinked-cellulose, crosslinked-agarose or crosslinked-dextran, or a composite carrier obtained from a combination of the above-mentioned compounds, such as organic-organic carrier and organic-inorganic carrier. The solid support may also be a metallic support, such as magnetic beads.

The solid support may be a porous matrix in granular form, in the form of beads, fibers, fiber membranes, films or as a gel.

The solid support may be a porous matrix which has a particle size between 50 and 300 μm. Preferably, the solid support is Eupergit®, which are macroporous beads with a diameter of 100-250 μm, made by copolymerization of N,N'-methylene-bis-(methacrylamide), glycidyl methacrylate, allyl glycidyl ether and methacrylamide.

In order to fix (or attach, or bind, or couple) the one or more amino acid sequences or peptides (or derivatives thereof) to the solid support, the solid support may preferably comprise one or more functional groups to this end. Representative examples of those functional groups are the following: hydroxyl group, amino group, aldehyde group, carboxyl group, thiol group, a silanol group, an amide group, epoxy group, a halogen group, succinylimide group and an acid anhydride group.

The medical device of the present invention is able to efficiently bind and separate at least one component from an aqueous solution which potentially comprises said at least one component. For instance, the device of the present invention is able to capture chemical components of surface structures of bacteria (G+ and/or G−), such as endotoxins, such as LPS, LTA and/or PGN, since the toxins would bind to the one or more amino acid sequences or peptides (or derivatives thereof) of the present invention fixed on the solid support of the device. Preferably, the device of the present invention is able to capture one or more chemical components of surface structures of G− and/or G+ bacteria, such as endotoxins such as LPS, LTA and/or PGN potentially present in an aqueous solution selected from water, whole blood or a body fluid such as plasma, serum or other suitable blood fractions. This is accomplished by passing an aqueous solution such as water, blood or other body fluids through the device. When used clinically, the device can be applied preferably extracorporeally.

The present invention further provides a method for the removal, preferably extracorporeal removal, of at least one component, preferably one or more chemical components of surface structures of G− and/or G+ bacteria, such as endotoxins, such as LPS, LTA and/or PGN from an aqueous solution potentially comprising said at least one component, preferably body fluids from an animal, such a mammal and/or a non-mammal, as described above, preferably a mammal, including a human being, such as blood, plasma, serum or other suitable blood fractions, said method comprising:

providing an aqueous solution, preferably body fluids from an animal, such a mammal and/or a non-mammal, preferably a mammal, including a human being, such as blood, plasma, serum or other suitable blood fractions, which potentially comprises said at least one component, passing the aqueous solution, preferably body fluids from an animal, such a mammal and/or a non-mammal, preferably a mammal, including a human being, such as blood, plasma, serum or other suitable blood fractions through the medical device of the present invention under conditions which effect the binding of said at least one component, preferably one or more chemical components of surface structures of G− and/or G+ bacteria, such as endotoxins, such as LPS, LTA and/or PGN to the one or more amino acid sequences or peptides, or derivatives thereof, fixed on the solid support of the medical device, thus removing the at least one component from the aqueous solution.

Accordingly, the device of the present invention can be used in a method for the removal, preferably extracorporeal removal, of at least one component, preferably at least one chemical component of surface structures of G− and/or G+ bacteria, such as endotoxins, such as LPS, LTA and/or PGN from an aqueous solution, preferably body fluids from an animal, such a mammal and/or a non-mammal, preferably a mammal, including a human being, such as blood, plasma, serum or other suitable blood fractions, as described below.

For instance, the mammal may be a rodent (such as a mouse or a rat), a primate (such as an ape, monkey or lemur), a dog, a cat, a rabbit, and an ungulate such as cattle, horses or pigs. In a preferred embodiment, the mammal is a human. For instance, the non-mammal may be a chicken, a duck, a goose, an ostrich, a pigeon, a turkey, etc.).

The device of the invention can thus be used as a medicament, preferably in a therapeutic and/or preventive method of treatment, in a mammal including a human, or in a non-mammal, of an infectious disease, or of an inflammatory condition related to an infectious disease, or of an inflammatory disease related to the presence of a product derived from an infectious agent.

The present invention thus provides a therapeutic and/or preventive method of treatment of an infectious disease, or of an inflammatory condition related to an infectious disease, or of an inflammatory disease related to the presence of a product derived from an infectious agent for the extracorporeal removal of at least one component, preferably one or more chemical components of surface structures of G− and/or G+ bacteria, such as endotoxins, such as LPS, LTA and/or PGN from an aqueous solution, preferably body fluids from an animal, preferably a mammal, including a human being, or in a non-mammal, such as blood, plasma, serum or other suitable blood fractions.

The therapeutic and/or preventive method of treatment comprises passing the aqueous solution potentially comprising the at least one component, preferably body fluids from an animal, preferably a mammal, including a human being, or in a non-mammal, such as blood, plasma, serum or other suitable blood fractions through the medical device of the present invention under conditions which effect the binding of said at least one component, preferably one or more chemical components of surface structures of G− and/or G+ bacteria, such as endotoxins, such as LPS, LTA and/or PGN to the one or more amino acid sequences or peptides, or derivatives thereof, fixed on the solid support of the medical device, thus removing the at least one component from the aqueous solution.

In a particular embodiment, the infectious disease is a microbial infection. In more particular embodiments, the microbial infection is selected from the group consisting of a bacterial infection (either G+ or G− bacteria, saprophytic or pathogenic, aerobic or anaerobic), a fungal infection, a viral infection, a parasitic infection, and combinations thereof (polymicrobial infection).

In another particular embodiment, the infectious disease is a septicemia. As used herein, the term "septicemia" refers to the presence of any microbe in blood stream. Particularly, the septicemia is selected from the group consisting of a bacteremia, a fungemia, a viremia, a parasitemia, and combinations thereof. In another particular embodiment, the inflammatory condition is severe sepsis. In a particular embodiment, the sepsis is polymicrobial sepsis. In a particular embodiment of the invention, the inflammatory condition is SIRS (systemic inflammatory response syndrome). In another particular embodiment, the inflammatory condition is sepsis. In another particular embodiment, the inflammatory condition is septic shock. Finally, the septic shock may be endotoxin-induced septic shock.

The terms "treatment" or "therapy" encompass both prophylactic and curative methods of treating disease, since both are directed to the maintenance or restoration of health. Irrespective of the origin of the noxa, discomfort or incapacity, its relief, by the administration of an appropriate agent, is to be construed as therapy or therapeutic use in the context of the present application.

During the description of the claims, the word "comprising" and its variants does not intend to exclude other technical characteristics, additives, components or steps. In addition, the term "comprising" may also encompass the term "consisting of".

As used herein, the term "about" means the indicated value ±1% of its value, or the term "about" means the indicated value ±2% of its value, or the term "about" means the indicated value ±5% of its value, the term "about" means the indicated value ±10% of its value, or the term "about" means the indicated value ±20% of its value, or the term "about" means the indicated value ±30% of its value; preferably the term "about" means exactly the indicated value (±0%).

Unless otherwise defined, all technical and scientific terms used herein have the same meaning as commonly understood by one of ordinary skilled in the art to which this invention belongs. Methods and materials similar or equivalent to those described herein can be used in the practice of the present invention. Additional objects, advantages and features of the invention will become apparent to those skilled in the art upon examination of the description or may be learned by practice of the invention. The following examples and drawings are provided by way of illustration, and they are not intended to be limiting of the present invention.

EXAMPLES

Materials and Methods

Production and Purification of Recombinant Proteins and Peptides rshCD6 and rshCD5 proteins were purified following reported methods (Sarrias M R, et al., 2004, *Biochemical characterization of recombinant and circulating human Sp alpha. Tissue Antigens* 63:335-44; Sarrias M R, et al., 2007, *CD6 binds to pathogen-associated molecular patterns and protects from LPS-induced septic shock. Proc Natl Acad Sci USA* 104:11724-9) using SURE CHO-M Cell Line™ clones (Selexis SUREtechnology Platform™, Geneva, Switzerland) and size-exclusion chromatography protocols developed at PX" Therapeutics (Grenoble, France). Human and bovine seroalbumin (HAS and BSA, respectively) were purchased from Sigma-Aldrich (St. Louis, MO).

Peptides (CD6.PD1, GTVEVRLEASW (SEQ ID NO.: 1); CD6.PD2, GRVEMLEHGEW (SEQ ID NO.: 2) and CD6.PD3, GQVEVHFRGVW (SEQ ID NO.: 3); CD5.PD1, GQLEVYLKDGW (SEQ ID NO: 6); CD5.PD2, GVVEFYSGSLG (SEQ ID NO: 7); DMBT-1.pbs1, GRVEVLYRGSW (SEQ ID NO.: 8); and Peptide CD6 Pcons (also referred to as "Pcon", "CD6 con", "CD6.con", "CD6 cons", "PCons" or "CD6.cons", GRVEVLFRGSW (SEQ ID NO.: 9) (>80% purity) were manufactured by Solid Phase Peptide Synthesis by ProteoGenix (Shiltigheim, France), and stocked at 5 mg/mL with diluted (1:3) acetonitrile.

Bacterial Agglutination Assays $5\times10^8$ colony-forming units (CFU)/mL diluted in TTC buffer (50 mM Tris pH 7.5 plus 150 mM NaCl, % Tween 20, and 1 mM Ca 2+) were mixed (1:1) with different peptide concentrations (0-200 μg/mL) in 96 U-bottomed well microtiter plates (Biofil) (Bikker F J, et al., 2002, *Identification of the bacteria-binding peptide domain on salivary agglutinin (gp-340/DMBT1), a member of the scavenger receptor cysteine-rich superfamily, J Biol Chem* 277:32109-15). After overnight incubation at 37° C., bacterial agglutination was examined by light microscopy and scored from − (absent) to +++(maximal) by two independent observers.

Bacterial Strains

Multidrug resistant *Acinetobacter baumanii* clinical isolate, *Enterobacer cloacae* ATCC 23355, *Escherichia coli* ATCC 25922, *Klebsiella pneumoniae* ATCC 13883, *Listeria monocytogenes* ATCC 19111, *Pseudomonas aeruginosa* ATCC 27853, *Staphylococcus aureus* ATCC 25923, and Methicillin-resistant *Staphylococcus aureus* (MRSA) clinical isolate were provided by Dr. Jordi Vila (Microbiology Department, Hospital Clinic of Barcelona) and grown in Luria Bertoni or agar with 5% sheep blood (Becton Dikinson) at 37° C., except for *L. monocytogenes* that was cultured in Brain Heart infusion broth (Pronadisa).

Binding Assays

Intrinsic fluorescence experiments. To explore the ability of different peptides/proteins to bind LTA (Mr=14,000, from *S. aureus*) and rough LPS (Re-LPS, Mr=2500, from *Salmonella minnesota* serotype Re 595), binding studies were carried out in an AB2 spectrofluorimeter with a thermostated cuvette holder (±0.1° C.), using 5×5 mm path-length quartz cuvettes as described (Coya J M, et al., 2015, *Natural Anti-Infective Pulmonary Proteins: In Vivo Cooperative Action of Surfactant Protein SP-A and the Lung Antimicrobial Peptide SP-BN, J Immunol* 195:1628-36). Re-LPS concentration was assessed by quantification of 2-keto-3-deoxyoctulosonic acid (Garcia-Verdugo I, et al., 2003, *Effect of hydroxylation and N187-linked glycosylation on molecular and functional properties of recombinant human surfactant protein A, Biochemistry* 42:9532-42). Peptide/protein samples (10 μg/mL) were titrated with different amounts of a stock solution of either LTA or Re-LPS in phosphate buffered saline (PBS) pH 7.2, and the Trp fluorescence emission spectra recorded with excitation at 295 nm. The fluorescence intensity readings were corrected for the dilution caused by peptide/protein addition. Background intensities in peptide/protein-free samples due to LTA or Re-PS were subtracted from each recording. The apparent dissociation constant ($K_d$) of peptide/protein-ligand complexes were obtained by nonlinear least-squares fitting to the Hill equation of the change in peptide fluorescence at 353 nm with the amount of added LTA or Re-LPS (Garcia-Verdugo I, et al., 2003, *Effect of hydroxylation and N187-linked glycosylation on molecular and functional properties of recombinant human surfactant protein A, Biochemistry* 42:9532-42): $\Delta F/\Delta F_{max}=[L]^n/([L]^n+K_d)$, where ΔF is the change in fluorescence intensity at 353 nm relative to the intensity of free peptide; $\Delta F_{max}$ is the change in fluorescence intensity at saturating LTA or Re-LPS concentrations; [L] is the molar concentration of free ligand; and n is the Hill coefficient.

Solid Phase Binding Assays. 96-well microtiter plates (Nunc, Roskilde, Denmark) were coated overnight at 4° C. with 5 μg/mL of purified LPS (*E. coli* 0111:B4, Sigma L2630) or LTA (*S. aureus*, Sigma L2515) in PBS, and then incubated for 2 h at room temperature in blocking solution (20 mM Tris-HCl pH 7.4 plus 0.05% Tween 20 and 1% BSA). Biotin-labeled peptides/proteins (2.5-20 μg/mL) were added and incubated overnight at 4° C. in blocking solution. After extensive washing, bound peptides/proteins were detected by the addition of horseradish peroxidase (HRP)-labeled streptavidin (1:5,000 dilution; DAKO) for 1 h at room temperature. Color was developed by adding 3,3',5,5'-tetramethylbenzidine (TMB) liquid substrate (Sigma), and optical density read at 405-620 nm.

Dynamic Light Scattering (DLS)

The hydrodynamic diameters of peptides (10 μg/mL in PBS) were measured at 25° C. in a Zetasizer Nano S from Malvern Instruments (Worcestershire, UK) equipped with a 633 nm HeNe laser, as described (Saenz A, et al., 2010, *Fluidizing effects of C-reactive protein on lung surfactant membranes: protective role of surfactant protein A, FASEB J* 24:3662-73). Four scans were recorded for each sample, and samples were analyzed in triplicate.

In Vitro Cell Cultures

Spleens from 6-8 week old C57BL/6 mice (Charles River) were disaggregated by filtering through a cell strainer and, after erythrocyte lysis, cells were resuspended in RPMI 1640 with L-glutamine (Lonza) plus 10% fetal calf serum (BioWest), 100 U/mL penicillin, 100 μg/mL streptomycin and 50 μM 2-β Mercaptoethanol (Merck). Cells ($2\times10^5$) were stimulated for 48 h (at 37° C. in a humidified atmosphere with 5% $CO_2$) in U-bottomed 96-well plates (Biofil) containing LPS (0.5 μg/mL; *E. coli* O111:B4), in the presence or absence of increasing peptides (0.5-20 μg/mL). Culture supernatants were harvested and mouse cytokines measured by ELISA following manufacturer's instructions (BD Biosciences OptEIA sets).

Cecal Ligation and Puncture (CLP) Procedure

Animal procedures were approved by the Animal Experimentation Ethical Committee, University of Barcelona. High-grade mortality (0_90% mortality within the first 48-72 h) CLP-induced septic shock was induced in 8-10 week old C57BL/6J male mice (20-25 g; Charles River) as previously reported (Martinez-Florensa M, et al., 2017, *Protective Effects of Human and Mouse Soluble Scavenger-Like CD6 Lymphocyte Receptor in a Lethal Model of Polymicrobial Sepsis, Antimicrob Agents Chemother* 61:*e*01391-16).

For the assessment of bacterial load, blood and spleen samples from CLP-treated mice were collected, homogenized and diluted aseptically in sterile PBS. Serial dilutions were plated overnight on agar with 5% sheep blood (Becton Dickinson) at 37° C. Viable bacterial counts were expressed as CFU/mL (blood) or per mg (spleen).

Protein/Peptide Immobilization to Eupergit® Beads

Proteins or peptides (2.5 mg each) were immobilized via NH 2 groups on macroporous acrylic EUPERGIT® beads (0.2 g; Rohm-Pharma GmbH, Germany) following a previously described protocol (Zimmermann M, et al., 1999, *Endotoxin adsorbent based on immobilized human serum albumin. Clin Chem Lab Med* 37:373-379). Peptide or protein-coated Eupergit® beads are obtained by incubation with stirring of the polymeric beads at room temperature with a solution of the peptides of the invention in sodium phosphate buffer 100 mM pH 8 for 24 hours. After incubation, the beads were washed 3 times with 3 M sodium chloride pH 7.0, 30 mM sodium phosphate buffer pH 4.0 and 30 mM sodium phosphate buffer pH 8.0. Finally, 154 mM sodium chloride solution pH 7.0 was added to the peptide or protein-coated beads.

Endotoxin Assay

LPS detection was performed by using the turbidimetric-kinetic Limulus Amebocyte Lysate (LAL) kit-QCL (50-650U, Lonza) following manufacturer's instructions. Protein/peptide-coated EUPERGIT® beads were incubated 1:1 (v:v) with the provided endotoxin solution (50 UI/mL) for different periods of time (0-150 min) at room temperature following manufacturer's instructions.

Statistical Analysis

Survival assays were analyzed by a Log-Rank $\chi^2$ test using GraphPad Prism software. The significance of differences between experimental groups was determined by 2-tailed paired T test with 95% of confidence intervals (CI). P values were considered significant when $P<0.05$. Statistical analysis (mean±SEM) was performed using a 2-tailed Mann-Whitney test, with 95% of CI.

Results

Example 1. In Vitro and In Vivo Evidence Supporting the Broad Spectrum Bacterial Binding Properties of CD6-Derived Peptides Induction of Bacterial Agglutination by CD6-Derived Peptides The sequence and physicochemical properties of the studied CD6-derived peptides mapping at SRCR domains 1 to 3 (CD6.PD1, CD6.PD2 and CD6.PD3, respectively), as well as of the other peptides (CD6.cons, DMBT1.pbs1, CD5.PD1, and CD5.PD2) and proteins (rshCD6 (DQLNTS-SAESELWEPGERLPVRLTNGSSSCSGTVEVRLEAS-WEPACGALWDSRAAEAVCRALGCGGAEAASQL APPTPELPPPPAAGNTSVAANATLAGAPALLCS-GAEWRLCEVVEHACRSDGRRARVTCAEN-RALRLVDGGGAC AGRVEM-LEHGEWGSVCDDTWDLEDAHVVCRQLGCGWAVQA LPGLHFTPGRGPIHRDQVNCSGAEAYLWD CPGLPGQHYCGHKEDAGAVCSEHQSWRLTGGA-DRCEGOVEVHFRGVWNTVCD-SEWYPSEAKVLCQSLGCGT AVERPKGLPHSLS-GRMYYSCNGEELTLSNCSWRFNNSNLCSQSLAARVL CSASRSLHNLSTPEVPASVQTVTIESS VTVKIENK-ESR, SEQ ID NO.: 10) and rshCD5 (RL-TRSNSKCQGQLEVYLKDGWHMVCSQSWGRSSKQW EDPSQASKVCQRLNCGVPLSLGPFLVTYTPQSSIICY GQLGSFSNCSHSRNDMCHSLGLTCLEPQKTTPPT-TRPPPTTTPEPTAPPRLQLVAQSGGQH-CAGVVEFYSGSLG GTISYEAQDKTQDLEN-FLCNNLQCGSFLKHLPETEAGRAQDPGEPREHQPLPI QWKIQNSSCTSLEHCFRKIKPQ KSGRV-LALLCSGFQPKVQSRLVGGS-SICEGTVEVRQGAQWAALCDSSSARSSLRWEE-VCREQQCGSVNSYRVLD AGDPTSRGLFCPHQKLSQCHELWER-NSYCKKVFVTCQD, SEQ ID NO.: 11)) used in this study are compiled in FIG. 1A. In silico structural analyses depicted in FIG. 1B, showed that all CD6 peptides are accessible at the surface of CD6, with CD6.PD1 (and CD6.PD3) being exposed at opposing sides from that of CD6.PD2. As illustrated in FIG. 1C, the amino acid conservation of the CD6-derived peptides among different animal species is relatively high for CD6.PD2 and CD6.PD3, and lower for CD6.PD1.

Figure 2:
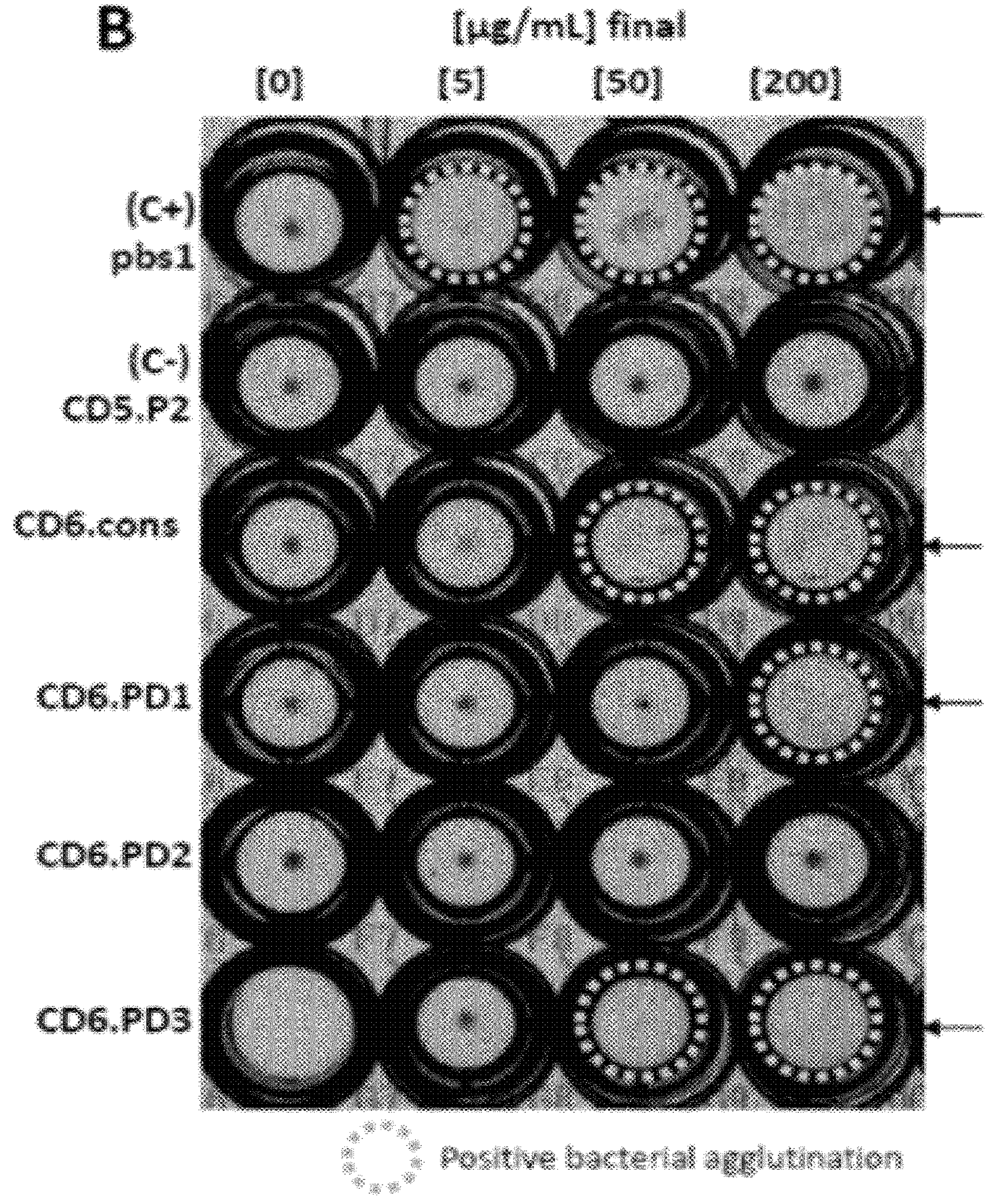
FIG. 2. Bacterial agglutination properties of CD6-derived peptides. Increasing concentrations (5, 50 and 200 μg/mL) of the indicated CD6 (PD1, PD2, and PD3), DMBT-1 (pbs1; C+) and CD5 (PD2; C−)-derived peptides were incubated for 2 h at room temperature in 96-well U-bottomed plates with alive bacterial cell suspensions (75×$10^6$ CFU/mL) in TTC buffer (50 mM Tris pH 7.5 plus 150 mM NaCl, 0.1% Tween 20, and 1 mM Ca 2+). Bacterial agglutination was scored and consensed by two independent observers as −, +/−, +, ++ or +++. (A) Summary of the agglutination results obtained with the indicated panel of Gram-negative (Multidrug resistant *Acinetobacter baumanii* clinical isolate; *Enterobacter cloacae* ATCC 23355; *Escherichia coli* ATCC 25922; *Klebsiella pneumoniae* ATCC 13883; *Listeria monocytogenes* ATCC 19111; *Pseudomonas aeruginosa* ATCC 27853) and Gram-positive (*Staphylococcus aureus* ATCC 25923; Methicillin-resistant *Staphylococcus aureus* (MRSA) clinical isolate) bacterial strains. (B) Representative agglutination results obtained for the MRSA clinical isolate.

None of the CD6-derived peptides fully matched the minimal 9-mer consensus motif (VEVLxxxxW) previously reported for the DMBT-1/SAG protein. The functionality of the CD6-derived peptides was explored in bacterial agglutination assays, in which the DMBT1.pbs1 (also referred to as DMBT-1.pbs1, or pbs1) and CD6.cons (also referred to as CD6 cons, or PCons) peptides were used as positive controls (Bikker F J, et al., 2004, *Bacteria binding by DMBT1/SAG/gp-340 is confined to the VEVLXXXXW motif in its scavenger receptor cysteine-rich domains, J Biol Chem* 279:47699-703). An analogous peptide sequence (CD5.PD2) present in the second SRCR domain of CD5-a highly homologous lymphocyte receptor for which no bacterial binding properties have been reported—was used as negative control. As illustrated by FIGS. 2A and 2B, dose-dependent agglutination of different G+ and G− bacterial suspensions (including MDR strains) was observed for CD6.PD1 and CD6.PD3, but not for CD6.PD2.

CD6-Derived Peptides Directly Interact with PAMPs Constitutive of G− and G+ Bacteria with Different Affinities Binding of biotin-labelled CD6-derived peptides to a solid-phase adsorbed with LPS or LTA was tested by ELISA. As shown by FIGS. 3A and 3B, all CD6-derived peptides showed dose-dependent binding to LPS and LTA, similar to the DMBT1.pbs1 and CD6.cons peptides used as positive controls. However, the CD6.PD3 peptide excelled in its ability to bind both immobilized LPS and LTA compared to the other tested peptides. As expected, no significant binding was observed for the CD5.PD1 peptide. These results confirm that CD6-derived peptides retain binding properties to LPS and LTA.

To further validate and measure binding, the underlying affinities for the interaction of CD6-derived peptides (CD6.PD1, CD6.PD2 and CD6.PD3) with LPS and LTA, and the corresponding $K_d$ values were determined by tryptophan fluorescence emission. The consensus sequences DMBT1.pbs1 and CD6.Pcons described by Bikker F J, et al., 2004 (*Bacteria binding by DMBT1/SAG/gp-340 is confined to the VEVLXXXXW motif in its scavenger receptor cysteine-rich domains, J Biol Chem* 279:47699-703) (also referred to as Pcons or Pcon, SEQ ID No.: 9, GRVEVLFRGSW) were also included in this experiment. As summarized in FIG. 4, all CD6-derived peptides displayed high affinities for both LPS and LTA, being higher for CD6.PD1 and/or CD6.PD2 compared to CD6.PD3 (PD1≥PD2≥PD3). $K_d$ values for CD6.PD1 and CD6.PD2 are lower than the prototypical DMBT1.pbs1 and CD6.cons peptides or the rshCD6 protein itself. Taken together, the binding results univocally support the direct and substantial interaction of CD6-derived peptides with essential cell wall components from G− and G+ bacterial strains.

Figures 4, 5:
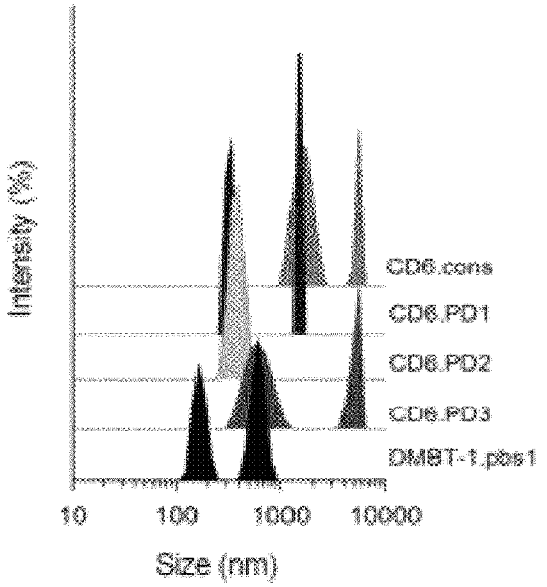
FIG. 4. $K_d$ analysis of the LPS and LTA interaction with CD6-derived peptides and protein. The apparent $K_d$ values for the binding of peptides and proteins in study to LPS and LTA determined by fluorescence emission of tryptophan residues are shown. Peptides/proteins (10 μg/mL) were titrated with or without increasing concentrations of Re-LPS or LTA in PBS. Peptide samples (with and without either Re-LPS or LTA) and blank samples (Re-LPS or LTA alone) were excited at 295 nm, and the emission spectra recorded from 300 to 400 nm. Results are expressed as the change in peptide fluorescence (ΔF) at the wavelength of the emission maxima (353 nm for the peptides and 337 nm for rshCD6 protein) in the presence and absence of either Re-LPS or LTA. Results are means±SD of 3 experiments. Peptide fluorescence changes at 353 nm were fitted to the Hill equation.
FIG. 5. Analysis of the hydrodynamic size of CD6-derived peptides in solution. The dynamic light scattering (DLS) analysis of the hydrodynamic diameter of CD6 (PD1, PD2, PD3, and Pcons) and DMBT-1/SAG (pbs1) derived peptides (10 μg/mL) in PBS is shown. The y axis represents the relative intensity of the scattered light; the x axis denotes the hydrodynamic diameter of the particles present in the solution. One representative experiment of four performed is shown (left). The numeric values obtained for each peptide are also shown (right).

To know whether self-aggregation properties of CD6-derived peptides are related to their agglutination properties, the hydrodynamic size of CD6-derived peptides in solution was analysed by DLS. Results indicate that CD6-derived peptides formed particles of different hydrodynamic sizes according to their self-aggregation properties (FIG. 5). CD6.PD3 particles exhibited two peaks, at 630±3 and 5151±7 nm, indicative of self-aggregation. A similar situation applied to CD6.PD1 (two peaks at 321±5 and 1484±8 nm), CD6.cons (two peaks of 1636±6 and 5493±7 nm), and DMBT1.pbs1 (two peaks of 169±5 and 617±4 nm). By contrast, CD6.PD2 showed a single peak centred at 379±5 nm, in line with its lower bacterial agglutination properties compared to the other CD6- and DMBT1-derived peptides.

Figure 6:
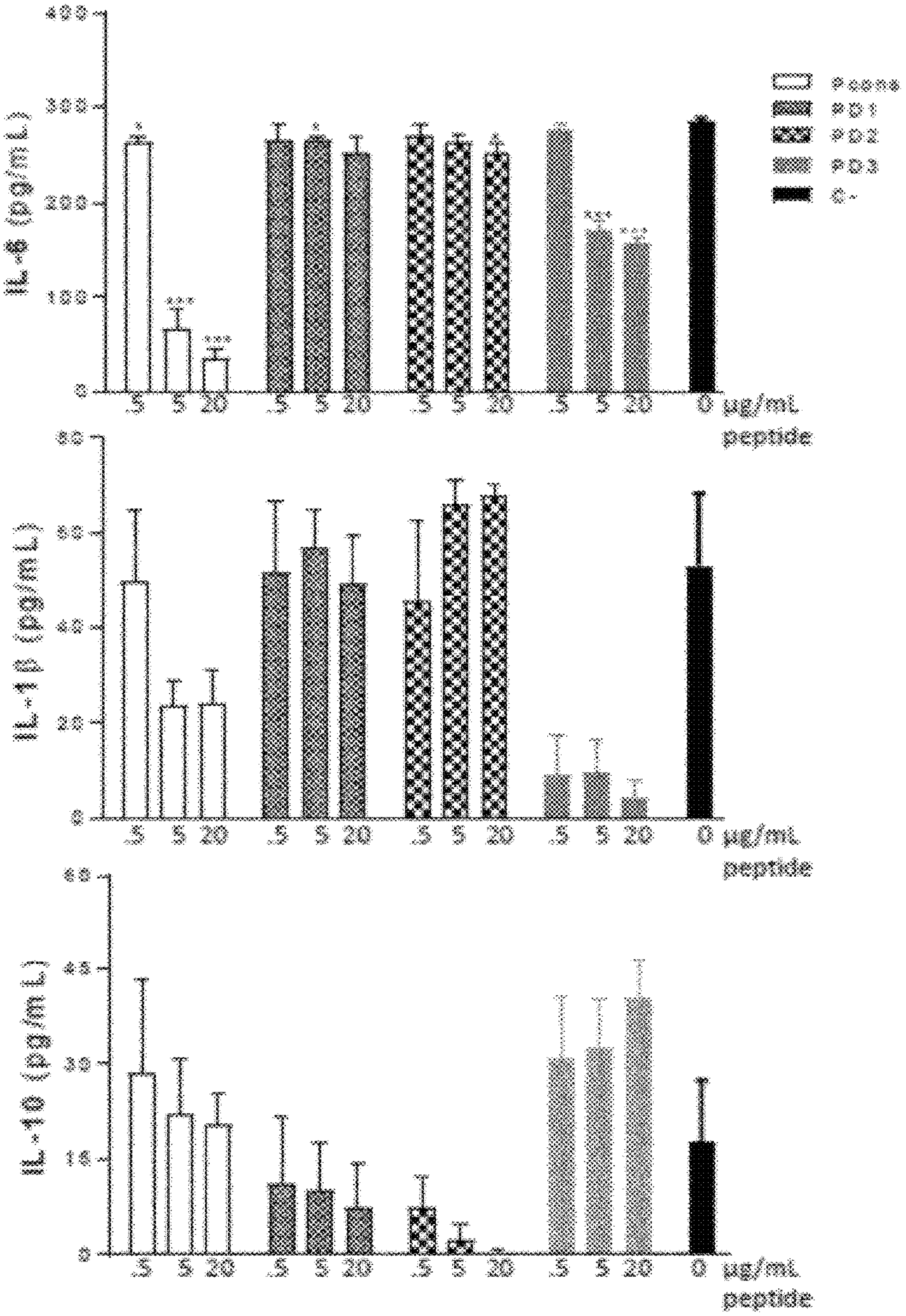
FIG. 6. Effect of CD6-derived peptides on in vitro LPS-induced cytokine release by mouse splenocytes. Total spleen cell suspensions (2×$10^5$) from C57BL/6 mice (n=7) were stimulated in triplicate for 48 h with LPS (0.5 μg/mL), in the presence or absence of increasing concentrations (0.5, 5, and 20 μg/mL) of CD6-derived peptides (PD1, PD2, PD3, and Pcons). Cytokine levels in culture supernatants were determined by ELISA and results expressed in pg/mL as mean±SD of triplicates. Viability was >75% at 48 h in all experimental conditions. Statistical analysis was performed using a 2-tailed Mann-Whitney test, with confidence intervals of 95% (*, P<0.05; , P<0.01; *, P<0.001).

Next, the functional relevance of CD6-derived peptides interaction with key pathogenic bacterial products was explored ex vivo. To this end, the modulatory effects of increasing concentrations of CD6-peptides on cytokine release by mouse splenocytes exposed to LPS were tested. As illustrated by FIG. 6, only the CD6.PD3 and CD6.cons peptides showed dose-dependent inhibitory effects on pro-inflammatory IL-6 and IL-1β cytokine release, which reached statistical significance in the former case. The same CD6.PD3 (but not CD6.cons) peptide also induced a non-statistically significant dose-dependent increased release of the anti-inflammatory cytokine IL-10.

In Vivo Efficacy of CD6-Derived Peptides in CLP-Induced Septic Shock

The effects of CD6-derived peptides in vivo were tested in mice undergoing CLP-induced septic shock (Rittirsch D, et al., 2009, *Immunodesign of experimental sepsis by cecal ligation and puncture, Nat Protoc* 4:31-6). To this end, a single intravenous (i.v.) dose (6 mg/kg) of the different peptides was infused to C57BL/6 mice 1 h post CLP-induction, and survival monitored thereafter. As shown in FIG. 7A, significant increased survival was observed among mice infused with CD6.PD2 (12.5%, P<0.0005) and CD6.PD3 (36.36%, P<0.0001) compared to the saline-treated group, a fact also observed in mice infused with the DMBT-1.pbs1 (23.07%, P<0.0025) and CD6.cons (25%, P<0.0101) peptides (FIG. 7B). No significant effects on mice survival were observed for the CD6.PD1 peptide.

Since the in vivo protective properties of CD6.PD3 against septic shock excelled CD6.PD1 and CD6.PD2, additional experiments exploring its time-, dose- and systemic via-dependent effects were performed. As shown in FIGS. 8A and 8B, maximal survival rates post CLP were obtained following CD6.PD3 infusion at 6 or 12 mg/kg doses (37.5% and 40%, respectively, vs 23.08% at 3 mg/kg), and at +1 h post CLP induction (40% vs 20% at +3 h). No significant differences between the intravenous (i.v.) or intraperitoneal (i.p.) pathways were observed when the CD6.PD3 peptide was infused at optimal conditions (6 mg/kg at +1 h post CLP) (FIG. 8C).

Figure 10:
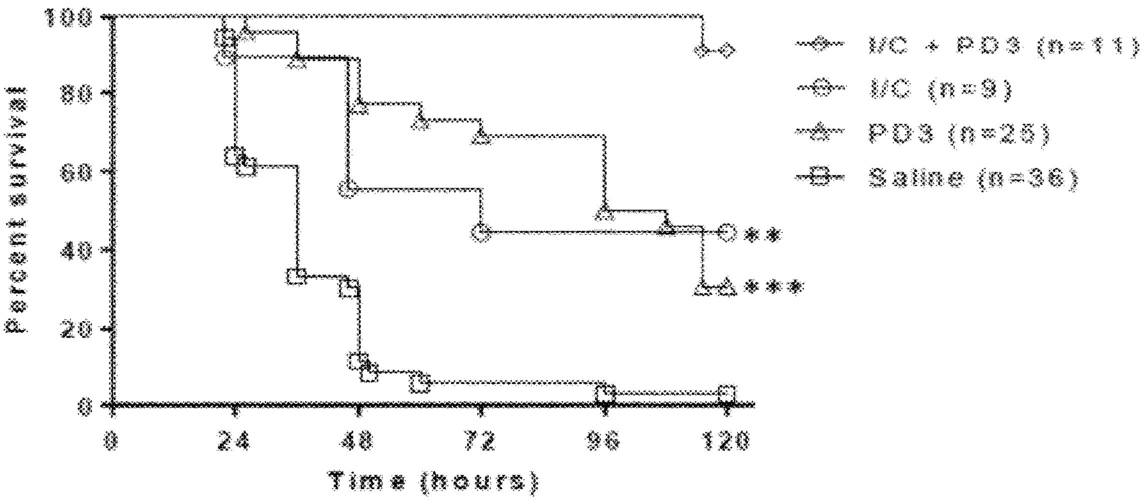
FIG. 10. Additive effects of combined administration of CD6.PD3 plus Imipenem/Cilastatin on mouse survival following CLP-induced sepsis. C57BL/6J mice were therapeutically infused at +1 h post CLP with saline (n=36), CD6.PD3 (6 mg/kg i.v.; n=25), Imipenem/Cilastatin (I/C, 50 mg/kg/12 h i.p.; n=9) or a combination of the two later (I/C+PD3, n=11). In all cases average percent survival was analyzed over time for each group and compared to the I/C plus CD6.PD3 group using the long-rank t-test (, P<0.02; *, P<0.002).

Next, the effect of the optimal CD6.PD3 peptide infusion conditions on serum cytokine levels and bacterial load post CLP were further monitored. To this end, C57BL/6 mice undergoing CLP-induced septic shock were treated with saline or CD6.PD3 peptide (single i.v. infusion of 6 mg/kg at +1 h post CLP) and thereafter bled and sacrificed at 4 h and 20 h later, respectively. As shown in FIG. 9A, CD6.PD3-treated mice exhibited significant lower levels (P<0.05) of the pro-inflammatory cytokines IL-1β, IL-6 and TNF-α at 20 h post CLP, compared with the saline-treated group. Similarly, the same CD6.PD3-treated mice also showed lower CFU isolated from blood and spleen when sacrificed at 20 h post CLP, compared with the saline control group (FIG. 9B). These results indicate that the CD6.PD3 peptide retains the therapeutic properties reported for the rshCD6 protein in experimental models of septic shock (Martinez-Florensa M, et al., 2017, *Protective Effects of Human and Mouse Soluble Scavenger-Like CD6 Lymphocyte Receptor in a Lethal Model of Polymicrobial Sepsis. Antimicrob Agents Chemother* 61:e01391-16). This also holds for septic mice simultaneously treated with CD6.PD3 and the broad-spectrum bactericidal antibiotic Imipenem/Cilastatin (I/C). As illustrated in FIG. 10, the combined administration of CD6.PD3 (6 mg/kg i.v.) and Imipenem/Cilastatin (50 mg/kg/12 h i.p.)+1 h post CLP-induced septic shock resulted in statistically significant additive/synergistic effects on mice survival (90.9%), compared to CD6.PD3 (30.8%; P=0.018) or I/C (44.4%; P=0.0015) individually.

Discussion

The present example shows that short (11-mer long) CD6-derived intradomain peptides retain in vitro and in vivo bacterial-recognition properties of the native CD6 protein. Such sequences (CD6.PD1, CD6.PD2 and CD6.PD3) map at surface-accessible sites of the three SRCR domains of CD6, and are homologous to the 11-mer consensus peptide (pbs1) identified in the DMBT-1/SAG protein (Bikker F J, et al., 2004, *Bacteria binding by DMBT1/SAG/gp*-340 *is confined to the VEVLXXXXW motif in its scavenger receptor cysteine-rich domains, J Biol Chem* 279:47699-703).

While i) similar homologous sequences from some SRCR-SF members possessing the minimal VEVLxxxxW consensus motif do not bind to bacteria (Bikker F J, et al., 2004, *Bacteria binding by DMBT*-1/*SAG/gp*-340 *is confined to the VEVLXXXXW motif in its scavenger receptor cysteine-rich domains, J Biol Chem* 279:47699-703), and ii) none of the CD6-derived peptides fully matched the above mentioned consensus motif, all the three CD6-derived peptides interact with both LPS and LTA albeit at different $K_d$, and with varied in vitro and in vivo functional properties (e.g., bacterial agglutination or prevention of CLP-induced mortality).

The CD6.PD3 peptide provided better in vivo results when assayed for therapeutically purposes in the mouse model CLP-induced septic shock compared with the other CD6-derived peptides (P=0.04 for CD6.PD2 and P=0.0005 for CD6.PD1). The CD6.PD3 also performed better than the prototypical DMBT-1.pbs1 peptide or the CD6.cons sequence, although the differences did not reach statistical significance (P=0.1). Another remarkable finding is the statistically significant additive/synergistic on mice survival effect of CD6.PD3 peptide when co-administered with Imipenem/Cilastatin, a member of the carbapenem family considered as first-choice treatment in critical care patients undergoing sepsis (Verwaest C, 2000, *Belgian Multicenter Study Group. Meropenem versus imipenem/cilastatin as empirical monotherapy for serious bacterial infections in the intensive care unit, Clin Microbiol Infect* 6:294-302). Therefore, CD6.PD3 gathers most of the anti-bacterial properties of rshCD6, thus constituting a good cost-effective alternative to the latter, as well as a good adjunctive strategy to antibiotic therapy.

In conclusion, the present findings show that short (11-mer) peptide sequences can retain the bacterial-binding properties of the whole extracellular region of CD6 open cost-effective opportunities for developing new alternatives to currently available sepsis treatments. The complex physiology of the sepsis response requires multi-disciplinary and simultaneously study of the various time dependent factors determining short and long-term sepsis outcome.

Figure 11:
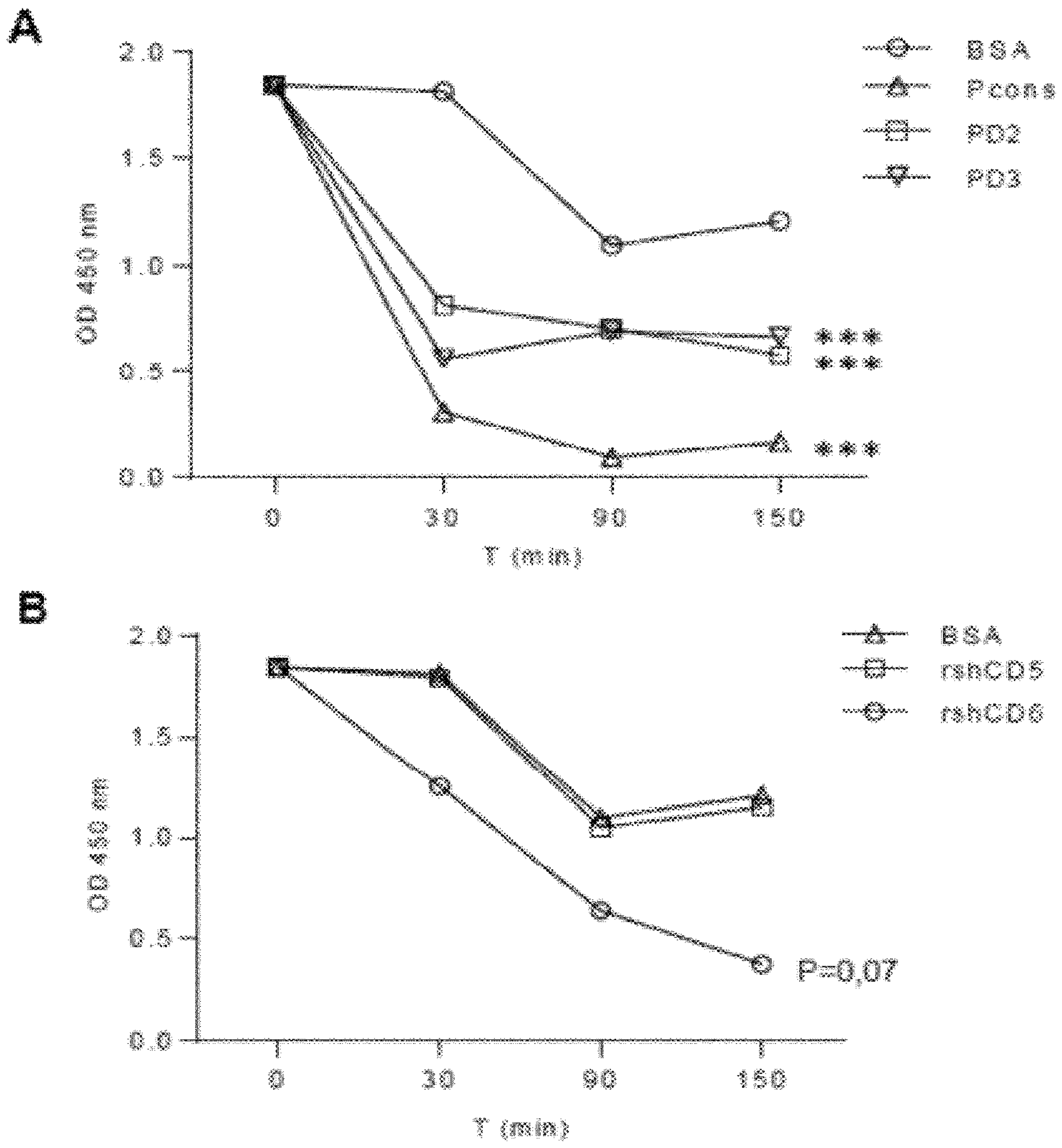
FIG. 11. Endotoxin adsorption assays on immobilized CD6-derived peptides and proteins. Eupergit® beads coated with different CD6-derived peptides (PD2, PD3, and Pcons) (A) or proteins (rshCD5 and rshCD6) (B) were incubated for different periods of time (0, 30, 90 and 150 min) with a 50 UI/mL endotoxin solution. Limulus amoebocyte lysate activating activity (LAL activity) of supernatants was then monitored along time and the OD 405-620 nm represented. Beads coated with Human Serum Albumin (HSA) were used as negative controls. Shown are triplicates of a representative experiment from two independent performed. Statistical analysis was done by using the 2-tailed paired T test with 95% confidence interval (***, P<0.001).

Example 2. Adsorption of Circulating Bacterial Toxins by CD6-Derived Peptides Covalently Coupled to a Solid-Phase Results Results obtained by incubating an endotoxin solution (50 UI/mL LPS) with Eupergit® beads coated with different CD6-derived peptides (CD6.PD2, CD6.PD3 and CD6.cons) or proteins (HSA (UniProtKB P02768, MKWVTFISLL-FLFSSAYSRGVFRRDAHKSEVAHRFKDLGEENFKA-LVLIAFAQYLQQCPFEDHVKLVNEVTEFAKT CVADE-SAENCDKSLHTLFGDKLCTVATLRETYGEMADCCAK QEPERNECFLQHKDDNPNLPRLVRPEVDVMCT AFHDNEETFLKKYLYEIARRHPYFYAPELLFFAKRY-KAAFTECCQAADKAACLLPKLDELRDEGKAS-SAKQRLKCAS LQKFGERAFKAWAVARLSQRFPKAE-FAEVSKLVTDLTKVHTECCHGDLLECADDRADLAKYI-CENQDSISSKLKEC CEKPLLEKSHCIAEVENDEMPADLPS-LAADFVESKDVCKNYAEAKDVFLGMFLYEYAR-RHPDYSVVLLLRLAKTYE TTLEKCCAAADPHECYA-KVFDEFKPLVEEPQNLIKQNCELFEQLGEYKFQNALL-VRYTKKVPQVSTPTLVEVSRNL GKVGSKCCKHPEAKRMPCAEDYLSVVLNQLCVL-HEKTPVSDRVTKCCTESLVNRRPCFSALEVDE-TYVPKEFNAE TFTFHADICTLSEKERQIK-KQTALVELVKHKPKATKEQLKAVMDDFAAFVEKCC KADDKETCFAEEGKKLVAASQ AALGL, SEQ ID NO.: 12), rshCD5, and rshCD6) for different periods of time are shown in FIG. 11. CD6.PD2-, CD6.PD3- and rshCD6-coated beads reduced endotoxin levels (as detected by LAL assays) compared to HSA- and rshCD5-coated controls. The use of CD6-derived peptides for extracorporeal hemoperfusion has advantages over existing devices such as Polymyxin B-immobilized fiber blood-purification columns (Esteban E, et al., 2013, *Immunomodulation in sepsis: the role of endotoxin removal by polymyxin B-immobilized cartridge, Mediators Inflamm* 2013:507539): i) the reported affinity of the LPS/Polymixin B interaction ($K_d$ 100-900 nM, depending on the G− strain used) (McInerney M P, et al., 2016, *Quantitation of Polymyxin-Lipopolysaccharide Interactions Using an Image-Based Fluorescent Probe, J Pharm Sci;* 105:1006-10) is lower than that of CD6.PD1 and CD6.PD2 ($K_d$ 3.5±0.3 nM and 35±2 nM, respectively), and ii) Polymixin B mainly binds to LPS, while CD6.PD1 and CD6.PD2 also bind LTA with affinities of $K_d$ nM and 0.31±0.04 nM, respectively. Accordingly, the CD6-derived peptides can also be used in case of G+ infections, which are responsible for over 50% of sepsis (Martin G S, 2012, *Sepsis, severe sepsis and septic shock: changes in incidence, pathogens and outcomes, Expert Rev Anti Infect Ther* 10:701-6).

The invention claimed is:

1. A method for the treatment of a disease or condition in a subject, wherein the disease or condition is a bacterial infection, a fungal infection, or a combination thereof, bacterial septicemia, fungal septicemia, or a combination thereof, or an inflammatory disease which is systemic inflammatory response syndrome or sepsis caused by an infectious agent selected from the group consisting of a bacterium, a fungus, and combinations thereof, wherein said method comprises administering a therapeutically effective amount of an isolated amino acid sequence consisting of SEQ ID NO: 3 and derivatives thereof, to a subject having the disease or condition, wherein said derivatives are a peptide consisting of SEQ ID NO: 3 with (i) one modification of a C-terminal end selected from C-amidation and C-esterification and/or one modification of an N-terminal end selected from N-acylation and N-alkylation, (ii) replacement of one or more L-amino acids with corresponding D-amino acids, (iii) conjugation with polyethylene glycol or albumin, or (iv) combinations of any of (i), (ii), or (iii).

2. The method according to claim 1, wherein the disease or condition is a bacterial infection, a fungal infection, or a combination thereof.

3. The method according to claim 1, wherein said method comprises simultaneously, sequentially or separately co-administering to the subject the isolated amino acid sequence SEQ ID NO: 3 or derivatives thereof, and at least one anti-infectious agent.

4. The method according to claim 3, wherein the anti-infectious agent is an antibiotic.

5. The method according to claim 4, wherein the antibiotic is Imipenem.

6. The method according to claim 4, wherein the method further comprises the administration of a dehydropeptidase inhibitor or a beta-lactamase inhibitor.

7. The method according to claim 6, wherein the dehydropeptidase inhibitor or beta-lactamase inhibitor is Cilastatin.

8. The method according to claim 6, wherein the antibiotic is Imipenem and the dehydropeptidase inhibitor or beta-lactamase inhibitor is Cilastatin.

9. The method according to claim 6, wherein the amino acid sequence is SEQ ID NO: 3, the antibiotic is Imipenem and the dehydropeptidase inhibitor or beta-lactamase inhibitor is Cilastatin.

* * * * *

SEQUENCE LISTING

```
Sequence total quantity: 69
SEQ ID NO: 1            moltype = AA  length = 11
FEATURE                 Location/Qualifiers
REGION                  1..11
                        note = CD6.PD1
source                  1..11
                        mol_type = protein
                        organism = synthetic construct
SEQUENCE: 1
GTVEVRLEAS W                                                          11

SEQ ID NO: 2            moltype = AA  length = 11
FEATURE                 Location/Qualifiers
REGION                  1..11
                        note = CD6.PD2
source                  1..11
                        mol_type = protein
                        organism = synthetic construct
SEQUENCE: 2
GRVEMLEHGE W                                                          11

SEQ ID NO: 3            moltype = AA  length = 11
FEATURE                 Location/Qualifiers
REGION                  1..11
                        note = CD6.PD3
source                  1..11
                        mol_type = protein
                        organism = synthetic construct
SEQUENCE: 3
GQVEVHFRGV W                                                          11

SEQ ID NO: 4            moltype = AA  length = 373
FEATURE                 Location/Qualifiers
REGION                  1..373
                        note = MISC_FEATURE - hCD6
source                  1..373
                        mol_type = protein
                        organism = Homo sapiens
SEQUENCE: 4
DQLNTSSAES ELWEPGERLP VRLTNGSSSC SGTVEVRLEA SWEPACGALW DSRAAEAVCR  60
ALGCGGAEAA SQLAPPTPEL PPPPAAGNTS VAANATLAGA PALLCSGAEW RLCEVVEHAC  120
RSDGRRARVT CAENRALRLV DGGGACAGRV EMLEHGEWGS VCDDTWDLED AHVVCRQLGC  180
GWAVQALPGL HFTPGRGPIH RDQVNCSGAE AYLWDCPGLP GQHYCGHKED AGVVCSEHQS  240
WRLTGGADRC EGQVEVHFRG VWNTVCDSEW YPSEAKVLCQ SLGCGTAVER PKGLPHSLSG  300
RMYYSCNGEE LTLSNCSWRF NNSNLCSQSL AARVLCSASR SLHNLSTPEV PASVQTVTIE  360
SSVTVKIENK ESR                                                     373

SEQ ID NO: 5            moltype = DNA  length = 1122
FEATURE                 Location/Qualifiers
misc_feature            1..1122
                        note = hCD6
source                  1..1122
                        mol_type = genomic DNA
                        organism = Homo sapiens
SEQUENCE: 5
gaccagctca acaccagcag tgcagagagt gagctctggg agccagggga gcggcttccg  60
gtccgtctga caaacgggag cagcagctgc agcgggacgg tggaggtgcg gctcgaggcg  120
tcctgggagc ccgcgtgcgg ggcgctctgg gacagccgcg ccgccgaggc cgtgtgccga  180
gcactgggct gcggcggggc ggaggccgcc tctcagctcg ccccgccgac ccctgagctg  240
ccgcccccgc ctgcagccgg gaacaccagc gtagcagcta atgccactct ggccggggcg  300
cccgccctcc tgtgcagcgg cgccgagtgg cggctctgcg aggtggtgga gcacgcgtgc  360
cgcagcgacg ggaggcgggc ccgtgtcacc tgtgcagaga accgcgcgct gcgcctggtg  420
gacggtggcg gcgcctgcgc cggccgcgtg gagatgctgg agcatggcga gtggggatca  480
gtgtgcgatg acacttggga cctggaggac gcccacgtgg tgtgcaggca actgggctgc  540
ggctgggcag tccaggccct gcccggcttg cacttcacgc ccggccgcgg gcctatccac  600
cgggaccagg tgaactgctc gggggccgaa gcttacctgt gggactgccc ggggctgcca  660
ggacagcact actgcggcca caaagaggac gcgggcgtgg tgtgctcaga gcaccagtcc  720
tggcgcctga caggggggcgc tgaccgctgc gaggggcagg tggaggtaca cttccgaggg  780
```

```
gtctggaaca cagtgtgtga cagtgagtgg tacccatcgg aggccaaggt gctctgccag  840
tccttgggct gtggaactgc ggttgagagg cccaaggggc tgccccactc cttgtccggc  900
aggatgtact actcatgcaa tggggaggag ctcaccctct ccaactgctc ctggcggttc  960
aacaactcca acctctgcag ccagtcgctg gcagccaggg tcctctgctc agcttcccgg  1020
agtttgcaca atctgtccac tcccgaagtc cctgcaagtg ttcagacagt cactatagaa  1080
tcttctgtga cagtgaaaat agagaacaag gaatctcggt ag                     1122

SEQ ID NO: 6           moltype = AA  length = 11
FEATURE                Location/Qualifiers
REGION                 1..11
                       note = CD5.PD1
source                 1..11
                       mol_type = protein
                       organism = synthetic construct
SEQUENCE: 6
GQLEVYLKDG W                                                       11

SEQ ID NO: 7           moltype = AA  length = 11
FEATURE                Location/Qualifiers
REGION                 1..11
                       note = CD5.PD2
source                 1..11
                       mol_type = protein
                       organism = synthetic construct
SEQUENCE: 7
GVVEFYSGSL G                                                       11

SEQ ID NO: 8           moltype = AA  length = 11
FEATURE                Location/Qualifiers
REGION                 1..11
                       note = DMBT-1.pbs1
source                 1..11
                       mol_type = protein
                       organism = synthetic construct
SEQUENCE: 8
GRVEVLYRGS W                                                       11

SEQ ID NO: 9           moltype = AA  length = 11
FEATURE                Location/Qualifiers
REGION                 1..11
                       note = CD6 Pcon
source                 1..11
                       mol_type = protein
                       organism = synthetic construct
SEQUENCE: 9
GRVEVLFRGS W                                                       11

SEQ ID NO: 10          moltype = AA  length = 373
FEATURE                Location/Qualifiers
REGION                 1..373
                       note = rshCD6
source                 1..373
                       mol_type = protein
                       organism = synthetic construct
SEQUENCE: 10
DQLNTSSAES ELWEPGERLP VRLTNGSSSC SGTVEVRLEA SWEPACGALW DSRAAEAVCR  60
ALGCGGAEAA SQLAPPTPEL PPPPAAGNTS VAANATLAGA PALLCSGAEW RLCEVVEHAC  120
RSDGRRARVT CAENRALRLV DGGGACAGRV EMLEHGEWGS VCDDTWDLED AHVVCRQLGC  180
GWAVQALPGL HFTPGRGPIH RDQVNCSGAE AYLWDCPGLP GQHYCGHKED AGAVCSEHQS  240
WRLTGGADRC EGQVEVHFRG VWNTVCDSEW YPSEAKVLCQ SLGCGTAVER PKGLPHSLSG  300
RMYYSCNGEE LTLSNCSWRF NNSNLCSQSL AARVLCSASR SLHNLSTPEV PASVQTVTIE  360
SSVTVKIENK ESR                                                     373

SEQ ID NO: 11          moltype = AA  length = 334
FEATURE                Location/Qualifiers
REGION                 1..334
                       note = rshCD5
source                 1..334
                       mol_type = protein
                       organism = synthetic construct
SEQUENCE: 11
RLTRSNSKCQ GQLEVYLKDG WHMVCSQSWG RSSKQWEDPS QASKVCQRLN CGVPLSLGPF  60
LVTYTPQSSI ICYGQLGSFS NCSHSRNDMC HSLGLTCLEP QKTTPPTTRP PPTTTPEPTA  120
PPRLQLVAQS GGQHCAGVVE FYSGSLGGTI SYEAQDKTQD LENFLCNNLQ CGSFLKHLPE  180
TEAGRAQDPG EPREHQPLPI QWKIQNSSCT SLEHCFRKIK PQKSGRVLAL LCSGFQPKVQ  240
SRLVGGSSIC EGTVEVRQGA QWAALCDSSS ARSSLRWEEV CREQQCGSVN SYRVLDAGDP  300
TSRGLFCPHQ KLSQCHELWE RNSYCKKVFV TCQD                              334

SEQ ID NO: 12          moltype = AA  length = 609
```

-continued

```
FEATURE               Location/Qualifiers
REGION                1..609
                      note = MISC_FEATURE - HSA
source                1..609
                      mol_type = protein
                      organism = Homo sapiens
SEQUENCE: 12
MKWVTFISLL FLFSSAYSRG VFRRDAHKSE VAHRFKDLGE ENFKALVLIA FAQYLQQCPF  60
EDHVKLVNEV TEFAKTCVAD ESAENCDKSL HTLFGDKLCT VATLRETYGE MADCCAKQEP  120
ERNECFLQHK DDNPNLPRLV RPEVDVMCTA FHDNEETFLK KYLYEIARRH PYFYAPELLF  180
FAKRYKAAFT ECCQAADKAA CLLPKLDELR DEGKASSAKQ RLKCASLQKF GERAFKAWAV  240
ARLSQRFPKA EFAEVSKLVT DLTKVHTECC HGDLLECADD RADLAKYICE NQDSISSKLK  300
ECCEKPLLEK SHCIAEVEND EMPADLPSLA ADFVESKDVC KNYAEAKDVF LGMFLYEYAR  360
RHPDYSVVLL LRLAKTYETT LEKCCAAADP HECYAKVFDE FKPLVEEPQN LIKQNCELFE  420
QLGEYKFQNA LLVRYTKKVP QVSTPTLVEV SRNLGKVGSK CCKHPEAKRM PCAEDYLSVV  480
LNQLCVLHEK TPVSDRVTKC CTESLVNRRP CFSALEVDET YVPKEFNAET FTFHADICTL  540
SEKERQIKKQ TALVELVKHK PKATKEQLKA VMDDFAAFVE KCCKADDKET CFAEEGKKLV  600
AASQAALGL                                                        609

SEQ ID NO: 13         moltype = AA  length = 17
FEATURE               Location/Qualifiers
REGION                1..17
                      note = Peptide
source                1..17
                      mol_type = protein
                      organism = synthetic construct
SEQUENCE: 13
CSGTVEVRLE ASWEPAC                                              17

SEQ ID NO: 14         moltype = AA  length = 15
FEATURE               Location/Qualifiers
REGION                1..15
                      note = Peptide
source                1..15
                      mol_type = protein
                      organism = synthetic construct
SEQUENCE: 14
SGTVEVRLEA SWEPA                                                15

SEQ ID NO: 15         moltype = AA  length = 14
FEATURE               Location/Qualifiers
REGION                1..14
                      note = Peptide
source                1..14
                      mol_type = protein
                      organism = synthetic construct
SEQUENCE: 15
SGTVEVRLEA SWEP                                                 14

SEQ ID NO: 16         moltype = AA  length = 13
FEATURE               Location/Qualifiers
REGION                1..13
                      note = Peptide
source                1..13
                      mol_type = protein
                      organism = synthetic construct
SEQUENCE: 16
SGTVEVRLEA SWE                                                  13

SEQ ID NO: 17         moltype = AA  length = 12
FEATURE               Location/Qualifiers
REGION                1..12
                      note = Peptide
source                1..12
                      mol_type = protein
                      organism = synthetic construct
SEQUENCE: 17
SGTVEVRLEA SW                                                   12

SEQ ID NO: 18         moltype = AA  length = 14
FEATURE               Location/Qualifiers
REGION                1..14
                      note = Peptide
source                1..14
                      mol_type = protein
                      organism = synthetic construct
SEQUENCE: 18
GTVEVRLEAS WEPA                                                 14
```

-continued

```
SEQ ID NO: 19           moltype = AA  length = 13
FEATURE                 Location/Qualifiers
REGION                  1..13
                        note = Peptide
source                  1..13
                        mol_type = protein
                        organism = synthetic construct
SEQUENCE: 19
GTVEVRLEAS WEP                                                    13

SEQ ID NO: 20           moltype = AA  length = 12
FEATURE                 Location/Qualifiers
REGION                  1..12
                        note = Peptide
source                  1..12
                        mol_type = protein
                        organism = synthetic construct
SEQUENCE: 20
GTVEVRLEAS WE                                                     12

SEQ ID NO: 21           moltype = AA  length = 17
FEATURE                 Location/Qualifiers
REGION                  1..17
                        note = Peptide
source                  1..17
                        mol_type = protein
                        organism = synthetic construct
SEQUENCE: 21
CAGRVEMLEH GEWGSVC                                                17

SEQ ID NO: 22           moltype = AA  length = 15
FEATURE                 Location/Qualifiers
REGION                  1..15
                        note = Peptide
source                  1..15
                        mol_type = protein
                        organism = synthetic construct
SEQUENCE: 22
AGRVEMLEHG EWGSV                                                  15

SEQ ID NO: 23           moltype = AA  length = 14
FEATURE                 Location/Qualifiers
REGION                  1..14
                        note = Peptide
source                  1..14
                        mol_type = protein
                        organism = synthetic construct
SEQUENCE: 23
AGRVEMLEHG EWGS                                                   14

SEQ ID NO: 24           moltype = AA  length = 13
FEATURE                 Location/Qualifiers
REGION                  1..13
                        note = Peptide
source                  1..13
                        mol_type = protein
                        organism = synthetic construct
SEQUENCE: 24
AGRVEMLEHG EWG                                                    13

SEQ ID NO: 25           moltype = AA  length = 12
FEATURE                 Location/Qualifiers
REGION                  1..12
                        note = Peptide
source                  1..12
                        mol_type = protein
                        organism = synthetic construct
SEQUENCE: 25
AGRVEMLEHG EW                                                     12

SEQ ID NO: 26           moltype = AA  length = 14
FEATURE                 Location/Qualifiers
REGION                  1..14
                        note = Peptide
source                  1..14
                        mol_type = protein
                        organism = synthetic construct
SEQUENCE: 26
GRVEMLEHGE WGSV                                                   14
```

```
SEQ ID NO: 27          moltype = AA  length = 13
FEATURE                Location/Qualifiers
REGION                 1..13
                       note = Peptide
source                 1..13
                       mol_type = protein
                       organism = synthetic construct
SEQUENCE: 27
GRVEMLEHGE WGS                                                     13

SEQ ID NO: 28          moltype = AA  length = 12
FEATURE                Location/Qualifiers
REGION                 1..12
                       note = Peptide
source                 1..12
                       mol_type = protein
                       organism = synthetic construct
SEQUENCE: 28
GRVEMLEHGE WG                                                      12

SEQ ID NO: 29          moltype = AA  length = 17
FEATURE                Location/Qualifiers
REGION                 1..17
                       note = Peptide
source                 1..17
                       mol_type = protein
                       organism = synthetic construct
SEQUENCE: 29
CEGQVEVHFR GVWNTVC                                                 17

SEQ ID NO: 30          moltype = AA  length = 15
FEATURE                Location/Qualifiers
REGION                 1..15
                       note = Peptide
source                 1..15
                       mol_type = protein
                       organism = synthetic construct
SEQUENCE: 30
EGQVEVHFRG VWNTV                                                   15

SEQ ID NO: 31          moltype = AA  length = 14
FEATURE                Location/Qualifiers
REGION                 1..14
                       note = Peptide
source                 1..14
                       mol_type = protein
                       organism = synthetic construct
SEQUENCE: 31
EGQVEVHFRG VWNT                                                    14

SEQ ID NO: 32          moltype = AA  length = 13
FEATURE                Location/Qualifiers
REGION                 1..13
                       note = Peptide
source                 1..13
                       mol_type = protein
                       organism = synthetic construct
SEQUENCE: 32
EGQVEVHFRG VWN                                                     13

SEQ ID NO: 33          moltype = AA  length = 12
FEATURE                Location/Qualifiers
REGION                 1..12
                       note = Peptide
source                 1..12
                       mol_type = protein
                       organism = synthetic construct
SEQUENCE: 33
EGQVEVHFRG VW                                                      12

SEQ ID NO: 34          moltype = AA  length = 14
FEATURE                Location/Qualifiers
REGION                 1..14
                       note = Peptide
source                 1..14
                       mol_type = protein
                       organism = synthetic construct
SEQUENCE: 34
```

-continued

```
GQVEVHFRGV WNTV                                                    14

SEQ ID NO: 35           moltype = AA  length = 13
FEATURE                 Location/Qualifiers
REGION                  1..13
                        note = Peptide
source                  1..13
                        mol_type = protein
                        organism = synthetic construct
SEQUENCE: 35
GQVEVHFRGV WNT                                                     13

SEQ ID NO: 36           moltype = AA  length = 12
FEATURE                 Location/Qualifiers
REGION                  1..12
                        note = Peptide
source                  1..12
                        mol_type = protein
                        organism = synthetic construct
SEQUENCE: 36
GQVEVHFRGV WN                                                      12

SEQ ID NO: 37           moltype = AA  length = 17
FEATURE                 Location/Qualifiers
REGION                  1..17
                        note = 13c
DISULFID                1..17
                        note = join(1,17)
source                  1..17
                        mol_type = protein
                        organism = synthetic construct
SEQUENCE: 37
CSGTVEVRLE ASWEPAC                                                 17

SEQ ID NO: 38           moltype = AA  length = 17
FEATURE                 Location/Qualifiers
REGION                  1..17
                        note = 21c
DISULFID                1..17
                        note = join(1,17)
source                  1..17
                        mol_type = protein
                        organism = synthetic construct
SEQUENCE: 38
CAGRVEMLEH GEWGSVC                                                 17

SEQ ID NO: 39           moltype = AA  length = 17
FEATURE                 Location/Qualifiers
REGION                  1..17
                        note = 29c
DISULFID                1..17
                        note = join(1,17)
source                  1..17
                        mol_type = protein
                        organism = synthetic construct
SEQUENCE: 39
CEGQVEVHFR GVWNTVC                                                 17

SEQ ID NO: 40           moltype = AA  length = 17
FEATURE                 Location/Qualifiers
REGION                  1..17
                        note = peptide
source                  1..17
                        mol_type = protein
                        organism = synthetic construct
SEQUENCE: 40
CSGTVEVRFE ASWEPAC                                                 17

SEQ ID NO: 41           moltype = AA  length = 17
FEATURE                 Location/Qualifiers
REGION                  1..17
                        note = peptide
source                  1..17
                        mol_type = protein
                        organism = synthetic construct
SEQUENCE: 41
CSGTVEVRLR ASWEPAC                                                 17

SEQ ID NO: 42           moltype = AA  length = 13
```

```
FEATURE                 Location/Qualifiers
REGION                  1..13
                        note = peptide
source                  1..13
                        mol_type = protein
                        organism = synthetic construct
SEQUENCE: 42
SGLHGGSGMG QPG                                                           13

SEQ ID NO: 43           moltype = AA  length = 16
FEATURE                 Location/Qualifiers
REGION                  1..16
                        note = peptide
source                  1..16
                        mol_type = protein
                        organism = synthetic construct
SEQUENCE: 43
CSGSVKVLLE SWEPVC                                                        16

SEQ ID NO: 44           moltype = AA  length = 16
FEATURE                 Location/Qualifiers
REGION                  1..16
                        note = peptide
source                  1..16
                        mol_type = protein
                        organism = synthetic construct
SEQUENCE: 44
CSGFVQVLLE SWEPVC                                                        16

SEQ ID NO: 45           moltype = AA  length = 17
FEATURE                 Location/Qualifiers
REGION                  1..17
                        note = peptide
source                  1..17
                        mol_type = protein
                        organism = synthetic construct
SEQUENCE: 45
CSGSVEVLLG ASWEPAH                                                       17

SEQ ID NO: 46           moltype = AA  length = 17
FEATURE                 Location/Qualifiers
REGION                  1..17
                        note = peptide
source                  1..17
                        mol_type = protein
                        organism = synthetic construct
SEQUENCE: 46
CSGTVEVWFG EAWKAAC                                                       17

SEQ ID NO: 47           moltype = AA  length = 17
FEATURE                 Location/Qualifiers
REGION                  1..17
                        note = peptide
source                  1..17
                        mol_type = protein
                        organism = synthetic construct
SEQUENCE: 47
CEGTVEVWFQ QSWQPVC                                                       17

SEQ ID NO: 48           moltype = AA  length = 17
FEATURE                 Location/Qualifiers
REGION                  1..17
                        note = peptide
source                  1..17
                        mol_type = protein
                        organism = synthetic construct
SEQUENCE: 48
CNGTVEVRLG LSWKPAC                                                       17

SEQ ID NO: 49           moltype = AA  length = 17
FEATURE                 Location/Qualifiers
REGION                  1..17
                        note = peptide
source                  1..17
                        mol_type = protein
                        organism = synthetic construct
SEQUENCE: 49
CSGLVEVWFR LSWGPAC                                                       17
```

```
SEQ ID NO: 50           moltype = AA  length = 17
FEATURE                 Location/Qualifiers
REGION                  1..17
                        note = peptide
source                  1..17
                        mol_type = protein
                        organism = synthetic construct
SEQUENCE: 50
CSGTVEVWIR QSWEPAC                                                 17

SEQ ID NO: 51           moltype = AA  length = 17
FEATURE                 Location/Qualifiers
REGION                  1..17
                        note = peptide
source                  1..17
                        mol_type = protein
                        organism = synthetic construct
SEQUENCE: 51
CKGTVEVHYH GMWVPAC                                                 17

SEQ ID NO: 52           moltype = AA  length = 18
FEATURE                 Location/Qualifiers
REGION                  1..18
                        note = peptide
source                  1..18
                        mol_type = protein
                        organism = synthetic construct
SEQUENCE: 52
CRWTFRLPGN RSGEAVPL                                                18

SEQ ID NO: 53           moltype = AA  length = 17
FEATURE                 Location/Qualifiers
REGION                  1..17
                        note = peptide
source                  1..17
                        mol_type = protein
                        organism = synthetic construct
SEQUENCE: 53
CSGVVEVLHR GLWRPVT                                                 17

SEQ ID NO: 54           moltype = AA  length = 17
FEATURE                 Location/Qualifiers
REGION                  1..17
                        note = peptide
source                  1..17
                        mol_type = protein
                        organism = synthetic construct
SEQUENCE: 54
CAGRVEILER GQWGSVC                                                 17

SEQ ID NO: 55           moltype = AA  length = 17
FEATURE                 Location/Qualifiers
REGION                  1..17
                        note = peptide
source                  1..17
                        mol_type = protein
                        organism = synthetic construct
SEQUENCE: 55
CAGRVEMLEH GEWGTVC                                                 17

SEQ ID NO: 56           moltype = AA  length = 17
FEATURE                 Location/Qualifiers
REGION                  1..17
                        note = peptide
source                  1..17
                        mol_type = protein
                        organism = synthetic construct
SEQUENCE: 56
CAGRVEMLQH GEWGTVC                                                 17

SEQ ID NO: 57           moltype = AA  length = 17
FEATURE                 Location/Qualifiers
REGION                  1..17
                        note = peptide
source                  1..17
                        mol_type = protein
                        organism = synthetic construct
SEQUENCE: 57
CAGRVEMLEY GRWGSVC                                                 17
```

```
SEQ ID NO: 58          moltype = AA  length = 17
FEATURE                Location/Qualifiers
REGION                 1..17
                       note = peptide
source                 1..17
                       mol_type = protein
                       organism = synthetic construct
SEQUENCE: 58
CEGRVEMLEH GQWGSVC                                                  17

SEQ ID NO: 59          moltype = AA  length = 17
FEATURE                Location/Qualifiers
REGION                 1..17
                       note = peptide
source                 1..17
                       mol_type = protein
                       organism = synthetic construct
SEQUENCE: 59
CAGRVEMLEH RQWGSVC                                                  17

SEQ ID NO: 60          moltype = AA  length = 17
FEATURE                Location/Qualifiers
REGION                 1..17
                       note = peptide
source                 1..17
                       mol_type = protein
                       organism = synthetic construct
SEQUENCE: 60
CAGRVEMLER GQWGSVC                                                  17

SEQ ID NO: 61          moltype = AA  length = 17
FEATURE                Location/Qualifiers
REGION                 1..17
                       note = peptide
source                 1..17
                       mol_type = protein
                       organism = synthetic construct
SEQUENCE: 61
CEGRVEVSEA DVWGTVC                                                  17

SEQ ID NO: 62          moltype = AA  length = 17
FEATURE                Location/Qualifiers
REGION                 1..17
                       note = peptide
source                 1..17
                       mol_type = protein
                       organism = synthetic construct
SEQUENCE: 62
CAGRVEVWKD GTWGTVC                                                  17

SEQ ID NO: 63          moltype = AA  length = 17
FEATURE                Location/Qualifiers
REGION                 1..17
                       note = peptide
source                 1..17
                       mol_type = protein
                       organism = synthetic construct
SEQUENCE: 63
CEGRVELWRE EKWGTVC                                                  17

SEQ ID NO: 64          moltype = AA  length = 17
FEATURE                Location/Qualifiers
REGION                 1..17
                       note = peptide
source                 1..17
                       mol_type = protein
                       organism = synthetic construct
SEQUENCE: 64
CEGQVEVHFR GVWSTVC                                                  17

SEQ ID NO: 65          moltype = AA  length = 17
FEATURE                Location/Qualifiers
REGION                 1..17
                       note = peptide
source                 1..17
                       mol_type = protein
                       organism = synthetic construct
SEQUENCE: 65
```

-continued

```
CEGQVEVYFR GVWSTVC                                          17

SEQ ID NO: 66          moltype = AA  length = 17
FEATURE                Location/Qualifiers
REGION                 1..17
                       note = peptide
source                 1..17
                       mol_type = protein
                       organism = synthetic construct
SEQUENCE: 66
CEGQVEVHYQ GVWSTVC                                          17

SEQ ID NO: 67          moltype = AA  length = 17
FEATURE                Location/Qualifiers
REGION                 1..17
                       note = peptide
source                 1..17
                       mol_type = protein
                       organism = synthetic construct
SEQUENCE: 67
CEGQVEVYFR GVWNTVC                                          17

SEQ ID NO: 68          moltype = AA  length = 17
FEATURE                Location/Qualifiers
REGION                 1..17
                       note = peptide
source                 1..17
                       mol_type = protein
                       organism = synthetic construct
SEQUENCE: 68
CEGQVEVYYR GVWNTVC                                          17

SEQ ID NO: 69          moltype = AA  length = 17
FEATURE                Location/Qualifiers
REGION                 1..17
                       note = peptide
source                 1..17
                       mol_type = protein
                       organism = synthetic construct
SEQUENCE: 69
CAGQVEVYYK GSWNTVC                                          17
```